(12) United States Patent
Schaetzer et al.

(10) Patent No.: US 8,574,607 B2
(45) Date of Patent: Nov. 5, 2013

(54) SPIROHETEROCYCLIC THIOFURAN DIONE DERIVATIVES

(75) Inventors: Jürgen Harry Schaetzer, Stein (CH); Thomas Pitterna, Stein (CH); Long Lu, Shanghai (CN); Yaming Wu, Shanghai (CN); Peter Renold, Stein (CH); Francesca Perruccio, Stein (CH); Jérome Yves Cassayre, Stein (CH); Michel Mueglebach, Stein (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 13/322,831

(22) PCT Filed: May 21, 2010

(86) PCT No.: PCT/CN2010/000728
§ 371 (c)(1),
(2), (4) Date: Nov. 28, 2011

(87) PCT Pub. No.: WO2010/135914
PCT Pub. Date: Dec. 2, 2010

(65) Prior Publication Data
US 2012/0071319 A1 Mar. 22, 2012

(30) Foreign Application Priority Data

May 26, 2009 (GB) .................................. 0909041.6
Nov. 19, 2009 (GB) .................................. 0920330.8
Nov. 27, 2009 (GB) .................................. 0920895.0

(51) Int. Cl.
*A01N 25/00* (2006.01)
*A01N 43/40* (2006.01)
*A01N 43/42* (2006.01)
*A61K 31/44* (2006.01)
*C07D 215/00* (2006.01)
*C07D 333/64* (2006.01)
*C07D 313/16* (2006.01)
*C07D 311/96* (2006.01)
*C07D 317/72* (2006.01)
*C07C 69/76* (2006.01)
*C07C 229/00* (2006.01)
*C07C 323/00* (2006.01)

(52) U.S. Cl.
USPC ........... 424/405; 504/129; 504/130; 504/209; 504/244; 504/246; 504/248; 504/251; 504/289; 504/299; 514/278; 514/301; 514/302; 514/315; 514/321; 546/16; 549/29; 549/50; 549/54; 549/55; 549/56; 549/330; 549/331; 549/341; 549/343; 549/345; 560/3; 560/9; 560/18; 560/19; 560/45; 560/51

(58) Field of Classification Search
USPC ................ 514/278, 301, 302, 315, 317, 321; 546/16; 549/29, 50, 54, 55, 56, 330, 549/331, 341, 343, 345; 560/3, 9, 18, 19, 560/45, 51; 504/129, 130, 209, 244, 246, 504/248, 251, 289, 299; 424/405
See application file for complete search history.

(56) References Cited

U.S. PATENT DOCUMENTS 6,555,567 B1 * 4/2003 Fischer et al. ................ 514/409
8,318,956 B2 * 11/2012 Bretschneider et al. ...... 549/319

FOREIGN PATENT DOCUMENTS

CN 1175257 3/1998
WO 2008022725 2/2008

* cited by examiner

*Primary Examiner* — Jane C Oswecki
(74) *Attorney, Agent, or Firm* — Brian D. McAlhaney

(57) ABSTRACT

Compounds of the formula (I) useful as pesticides are disclosed, wherein the substituents are as defined in claim 1.

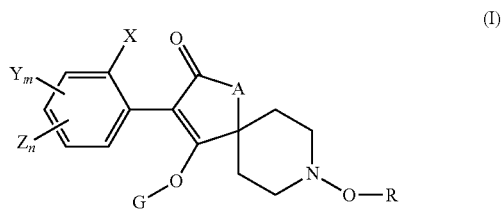

10 Claims, No Drawings

SPIROHETEROCYCLIC THIOFURAN DIONE DERIVATIVES

This application is a 371 of International Application No. PCT/CN2010/000728 filed May 21, 2010, which claims priority to GB 0909041.6 filed May 26, 2009, and GB 0920330.8 filed Nov. 19, 2009, and GB 0920895.0 filed Nov. 27, 2009, the contents of which are incorporated herein by reference.

The present invention relates to new spiroheterocyclic furan and thiofuran dione derivatives, to processes for preparing them, to pesticidal, in particular insecticidal, acaricidal, molluscicidal and nematicidal compositions comprising them and to methods of using them to combat and control pests such as insect, acarine, mollusc and nematode pests.

Spiroheterocyclic pyrrolidine dione derivatives are disclosed for example in WO 09/049,851.

It has now surprisingly been found that certain new spiroheterocyclic furan and thiofuran dione derivatives with nitrogen interrupting the spirocycle, especially those ones being N-oxy substituted, have good insecticidal properties.

The present invention therefore provides compounds of formula I

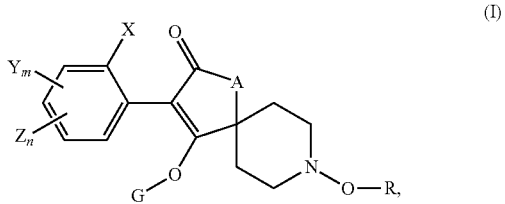

wherein
X, Y and Z independently of each other are $C_{1-4}$alkyl, $C_{3-6}$cycloalkyl, $C_{1-4}$haloalkyl, $C_{1-4}$alkoxy, $C_2$-$C_6$alkenyl, $C_2$-$C_6$alkynyl, halogen, phenyl or phenyl substituted by $C_{1-4}$alkyl, $C_{1-4}$haloalkyl, halogen or cyano;
m and n, independently of each other, are 0, 1, 2 or 3 and m+n is 0, 1, 2 or 3;
G is hydrogen, a metal, ammonium, sulfonium or a latentiating group;
A is oxygen or sulfur; and
R is hydrogen, $C_{1-6}$alkyl, $C_{1-6}$haloalkyl, $C_{1-6}$cyanoalkyl, $C_2$-$C_6$alkenyl, $C_3$-$C_6$alkynyl, benzyl, $C_{1-4}$alkoxy($C_{1-4}$)alkyl or $C_{1-4}$alkoxy($C_{1-4}$)alkoxy($C_{1-4}$)alkyl; or an agrochemically acceptable salt or an N-oxide thereof.

In the compounds of the formula I, each alkyl moiety either alone or as part of a larger group is a straight or branched chain and is, for example, methyl, ethyl, n-propyl, n-butyl, iso-propyl, sec-butyl, iso-butyl, tert-butyl, n-pentyl, iso-pentyl and n-hexyl.

Alkoxy groups preferably have a preferred chain length of from 1 to 4 carbon atoms. Alkoxy is, for example, methoxy, ethoxy, propoxy, i-propoxy, n-butoxy, isobutoxy, sec-butoxy and tert-butoxy. Such groups can be part of a larger group such as alkoxyalkyl and alkoxyalkoxyalkyl. Alkoxyalkyl groups preferably have a chain length of 1 to 4 carbon atoms. Alkoxyalkyl is, for example, methoxymethyl, methoxyethyl, ethoxymethyl, ethoxyethyl, n-propoxymethyl, n-propoxyethyl or isopropoxymethyl.

Halogen is generally fluorine, chlorine, bromine or iodine. This also applies, correspondingly, to halogen in combination with other meanings, such as haloalkyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

The preferred alkenyl and alkynyl radicals having 2 to 6 carbon atoms can be straight or branched and can contain more than 1 double or triple bond. Examples are vinyl, allyl, propargyl, butenyl, butynyl, pentenyl and pentynyl.

The cycloalkyl groups preferably have from 3 to 6 ring carbon atoms, for example cyclopropyl, cyclobutyl, cyclopentyl and cyclohexyl.

Phenyl, also as part of a substituent such as benzyl, may be substituted, preferably by alkyl, haloalkyl, halogen or cyano groups. In this case, the substituents can be in ortho, meta and/or para position. The preferred substituent positions are the ortho and para positions to the ring attachment point.

The latentiating groups G are selected to allow its removal by one or a combination of biochemical, chemical or physical processes to afford compounds of formula I where G is hydrogen before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

The latentiating group G is preferably selected from the groups $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—N($R^c$)—$R^d$, —$SO_2$—$R^e$, —$P(X^e)(R^f)$—$R^g$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$halo-alkoxy, halogen, cyano or nitro, heteroaryl or heteroaryl substituted by $C_1$-$C_3$ alkyl, $C_{1-3}$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and
$R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

It is also preferred that G is hydrogen, an alkali metal or alkaline earth metal, or an ammonium or sulfonium group, where hydrogen is especially preferred.

Depending on the nature of the substituents, compounds of formula I may exist in different isomeric forms. When G is hydrogen, for example, compounds of formula I may exist in different tautomeric forms:

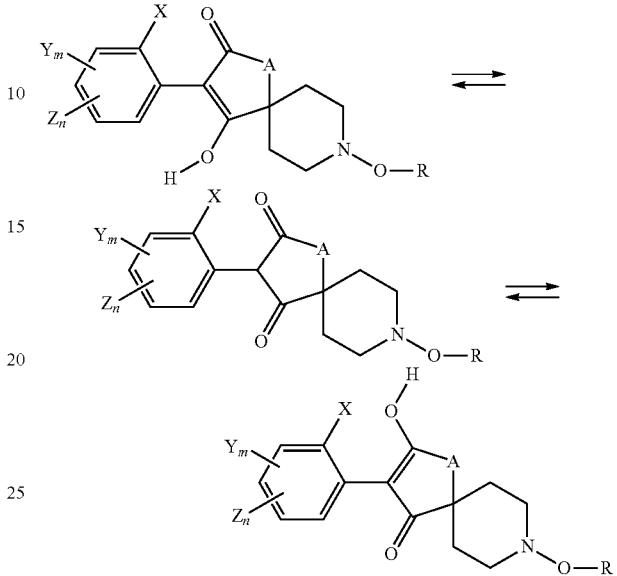

This invention covers all such isomers and tautomers and mixtures thereof in all proportions. Also, when substituents contain double bonds, cis- and trans-isomers can exist. These isomers, too, are within the scope of the claimed compounds of the formula I.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, propylamine, the four butylamine isomers, n-amylamine, i-amylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-i-propylamine, di-n-butylamine, di-n-amylamine, di-i-amylamine, dihexylamine, diheptylamine, dioctylamine, ethanolamine, n-propanolamine, i-propanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-i-opropylamine, tri-n-butylamine, tri-i-butylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, i-propylamine and di-i-propylamine.

Preferred quaternary ammonium bases suitable for salt formation correspond, for example, to the formula $[N(R_aR_bR_cR_d)]OH$, wherein $R_a$, $R_b$, $R_c$ and $R_d$ are each independently of the others hydrogen or $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula $[SR_eR_fR_g]OH$, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O=C—C=O unit.

The compounds of formula I according to the invention also include hydrates which may be formed during the salt formation.

Preferably, in the compounds of the formula (I), the substituent R is hydrogen, $C_{1-6}$alkyl, $C_{1-6}$haloalkyl, $C_{1-6}$cyanoalkyl, $C_2$-$C_6$alkenyl, $C_3$-$C_6$alkynyl, benzyl, $C_{1-4}$alkoxy($C_{1-4}$)alkyl or $C_{1-4}$alkoxy($C_{1-4}$alkoxy($C_{1-4}$)alkyl, in particular hydrogen, methyl, ethyl, propyl, isopropyl, cyanomethyl, trifluoromethyl, 2,2,2-trifluoroethyl, allyl, propargyl, benzyl, methoxymethyl, ethoxymethyl, methoxyethyl or methoxyethoxymethyl.

Preferably, X, Y and Z denote $C_1$-$C_4$alkyl, $C_3$-$C_6$cycloalkyl, $C_{1-4}$haloalkyl, $C_1$-$C_4$alkoxy, $C_2$-$C_6$alkenyl, $C_2$-$C_6$alkynyl or halogen, in particular methyl, ethyl, isopropyl, cyclopropyl, trifluoromethyl, methoxy, vinyl, ethynyl, fluoro, bromo, iodo or chloro, when m+n is 1-3, in particular, when m+n is 1-2.

Alternatively, Y and Z, independently of each other, denote $C_1$-$C_4$alkyl, $C_3$-$C_6$cycloalkyl, $C_{1-4}$haloalkyl, $C_1$-$C_4$alkoxy, $C_2$-$C_6$alkenyl, $C_2$-$C_6$alkynyl, halogen, phenyl or phenyl substituted by $C_{1-4}$alkyl, $C_{1-4}$haloalkyl or halogen, in particular methyl, ethyl, isopropyl, cyclopropyl, trifluoromethyl, methoxy, vinyl, ethynyl, fluoro, chloro, bromo, iodo, phenyl or phenyl substituted with methyl, trifluoromethyl or halogen, in particular fluoro or chloro, in particular in 4-position, when m+n is 1-3, in particular, when m+n is 1-2.

Preferably A is oxygen.

In another preferred group of compounds of the formula (I), R is hydrogen, methyl, ethyl, cyanomethyl, 2,2,2-trifluoroethyl, allyl, propargyl, benzyl, methoxymethyl, ethoxymethyl, methoxyethyl or methoxyethoxymethyl, X is methyl, ethyl, cyclopropyl, trifluoromethyl, methoxy, vinyl, ethynyl, fluoro, bromo, iodo or chloro, Y and Z, independently of each other, are methyl, ethyl, cyclopropyl, trifluoromethyl, methoxy, vinyl, ethynyl, fluoro, chloro, bromo, iodo, phenyl or phenyl substituted by halogen or $C_1$-$C_2$alkyl, G has the meanings assigned to it above, A is oxygen or sulfur and m+n is 1-3.

In a particularly preferred group of compounds of the formula (I), R is methyl, ethyl, cyanomethyl, 2,2,2-trifluoroethyl, allyl, propargyl, benzyl, methoxymethyl or methoxyethyl, X is methyl, ethyl, cyclopropyl, methoxy, vinyl, ethynyl, fluoro, bromo or chloro, Y and Z, independently of each other, are methyl, ethyl, cyclopropyl, methoxy, vinyl, ethynyl, fluoro, chloro, bromo, iodo, phenyl or phenyl substituted by halogen or $C_1$-$C_2$alkyl, G has the meanings assigned to it above, A is oxygen and m+n is 1-3; or, even more preferably, R is methyl, ethyl, cyanomethyl, 2,2,2-trifluoroethyl, allyl, propargyl, benzyl, methoxymethyl or methoxyethyl, X is methyl, ethyl, cyclopropyl, methoxy, vinyl, ethynyl, fluoro, bromo or chloro, Y and Z, independently of each other, are methyl, ethyl, cyclopropyl, methoxy, vinyl, ethynyl, fluoro, chloro, bromo, phenyl or phenyl substituted by halogen or $C_1$-$C_2$alkyl, G is hydrogen, A is oxygen and m+n is 1-3.

The invention covers also salts of the compounds of the formula I with amines, alkali metal and alkaline earth metal bases or quaternary ammonium bases.

Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_aR_bR_cR_d)]OH$ wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

The compounds of the invention may be made by a variety of methods. For example, the compounds of formula I, wherein the substituents have the meanings assigned to them above, can be prepared by means of processes known per se, e.g. by treating compounds of formula II with an alkylating, acylating, phosphorylating or sulfonylating agent G-Q in the presence of at least one equivalent of a base, where G is the alkyl, acyl, phosphoryl or sulfonyl group to be incorporated and Q is a nucleofuge:

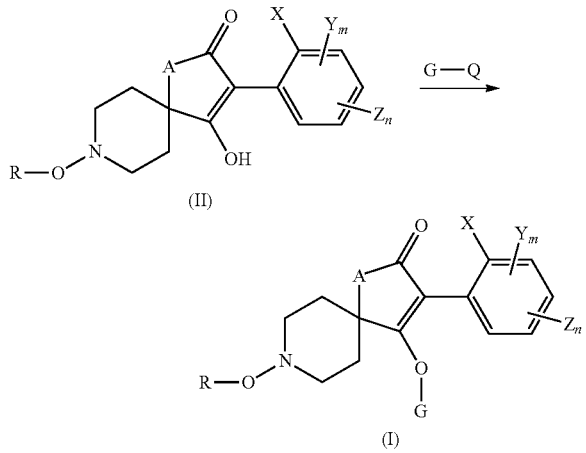

Compounds of formula I, in which X, Y, Z, m, n, A and R are as defined above and wherein G is a latentiating group of the formula —C(X$^a$)—R$^a$, C(X$^b$)—X$^c$—R$^b$ or —C(X$^d$)—NR$^c$R$^d$ may be prepared by procedures known in the art, described for example in WO 09/049,851.

Typically, compounds of formula II, in which X, Y, Z, m, n, A and R are as defined above, are treated with an acylating agent such as an acid halide (especially acid chloride), acid anhydride, haloformate (especially chloroformate), halothioformate (especially chlorothioformate), isocyanate, isothiocyanate, carbamoyl halide (especially carbamoyl chloride) or thiocarbamoyl halide (especially thiocarbamoyl chloride) in the presence of at least one equivalent of a suitable base, optionally in the presence of a suitable solvent. The base may be inorganic such as an alkali metal carbonate or hydroxide or a metal hydride, or an organic base such as a tertiary amine or metal alkoxide. Examples of suitable inorganic bases include sodium carbonate, sodium or potassium hydroxide, sodium hydride, and suitable organic bases include trialkylamines such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases, where the acylating agent is a carboxylic acid, acylation is preferably effected in the presence of a coupling agent such as 2-chloro-1-methylpyridinium iodide, N,N'-dicyclohexycarbodiimide, 1-(3-dimethylaminopropyl)-3-ethylcarbodiimide and N,N'-carbodiimidazole, and a base such as triethylamine or pyridine in a suitable solvent such as tetrahydrofuran, dichloromethane and acetonitrile.

Compounds of formula I, in which X, Y, Z, m, n, A and R are as defined above and wherein G is a latentiating group of the formula C(X$^b$)—X$^c$—R$^b$ or —C(X$^d$)—NR$^c$R$^d$, may be also be prepared by treating compounds of formula II, in which X, Y, Z, m, n, A and R are as defined above, with phosgene or a phosgene equivalent, optionally in the presence of a solvent such as toluene or ethyl acetate, and a base and reacting the resultant chloroformate, or equivalent, with an alcohol, thiol or amine under known conditions, as described, for example, in U.S. Pat. No. 6,774,133, U.S. Pat. No. 6,555,567 and U.S. Pat. No. 6,479,489.

Compounds of formula I, in which X, Y, Z, m, n, A and R are as defined above and wherein G is a latentiating group of the formula —P(X$^e$)R$^f$R$^g$, may be prepared from compounds of formula II, in which X, Y, Z, m, n, A and R are as defined above, using procedures described, for example, in U.S. Pat. No. 6,774,133, U.S. Pat. No. 6,555,567 and U.S. Pat. No. 6,479,489.

Compounds of formula I, in which X, Y, Z, m, n, A and R are as defined above and wherein G is a latentiating group of the formula —SO$_2$R$^e$, may be prepared by reaction of compounds of formula II, in which X, Y, Z, m, n, A and R are as defined above, with an alkyl or aryl sulfonyl halide, preferably in the presence of at least one equivalent of base.

Compounds of formula I, in which X, Y, Z, m, n, A and R are as defined above and wherein G is C$_1$-C$_6$alkyl, C$_2$-C$_6$alkenyl, C$_3$-C$_6$alkynyl or a latentiating group of the formula CH$_2$—X$^f$—R$^h$, may be prepared by treatment of a compound of formula II, in which X, Y, Z, m, n, A and R are as defined above, with a compound of formula G-Y wherein Y is a halogen (especially bromine or iodine), sulfonate (especially mesylate or tosylate) or a sulfate preferably in the presence of a base, under known conditions.

Compounds of formula III, in which X, Y, Z, m, n, A and G are as defined above,

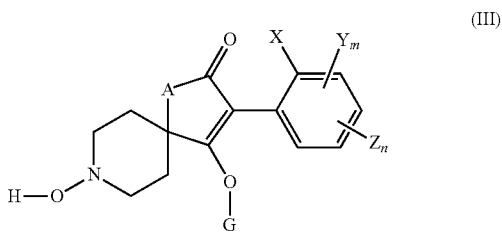

can be obtained by catalytic hydrogenation of compounds of formula I, in which X, Y, Z, m, n, A and G are as defined above and in which R is represented by a benzyl group.

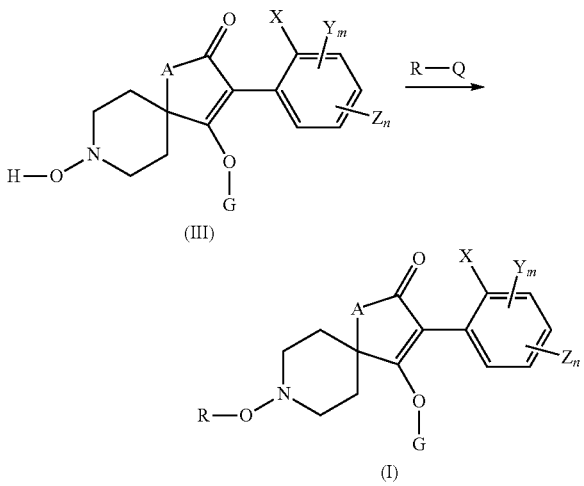

Compounds of formula I, in which X, Y, Z, m, n, R, A and G are as defined above, can be obtained by treating compounds of formula III, in which X, Y, Z, m, n, A and G are as defined above, with an alkylating agent R-Q, wherein R represents the alkyl group to be incorporated and Q represents a nucleofuge, in the presence of at least one equivalent of a base, and optionally in the presence of a suitable solvent.

Compounds of formula II may be prepared via the cyclisation of compounds of formula IV,

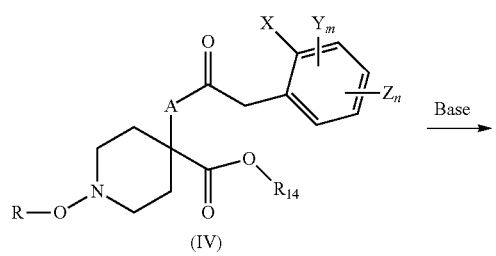

wherein $R_{14}$ is $C_{1-6}$alkyl, preferably in the presence of base, and optionally in the presence of a suitable solvent, by known methods described, for example, in WO 09/049,851. X, Y, Z, m, n, A and R are as defined above.

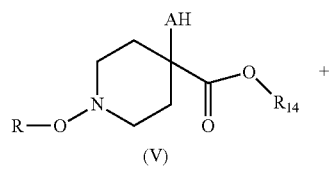

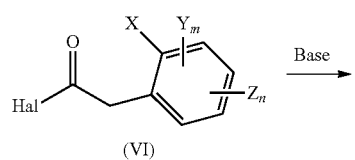

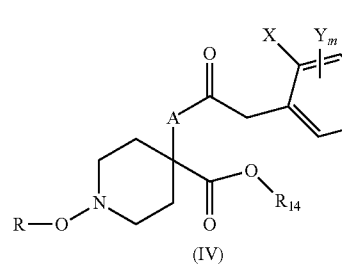

Compounds of formula IV may be prepared by reacting 4-hydroxy- (or 4-mercapto-) piperidine-4-carboxylic acid derivatives of formula V with phenylacetyl halides of formula VI, preferably in the presence of base in a suitable solvent by known methods described, for example, in WO 09/049,851.

X, Y, Z, m, n, R, A and $R_{14}$ are as defined above. The base may be inorganic such as an alkali metal carbonate or hydroxide or a metal hydride, or an organic base such as a tertiary amine or metal alkoxide. Examples of suitable inorganic bases include sodium carbonate, sodium or potassium hydroxide, sodium hydride, and suitable organic bases include trialkylamines such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent.

Phenylacetyl halides of formula VI, wherein Hal is Cl or Br and in which X, Y, Z, m, n are as defined above, are known compounds or can be prepared by known methods, described for example in WO 09/049,851.

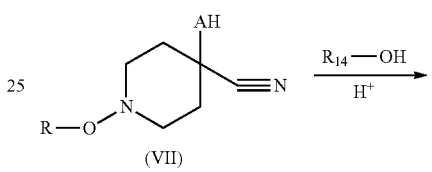

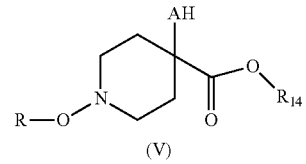

4-Hydroxy- (or 4-mercapto-) piperidine-4-carboxylic acid derivatives of the formula V, wherein $R_{14}$ is $C_1$-$C_6$alkyl, may be prepared by reacting cyanohydrins of the formula VII with an alcohol of the formula $R_{14}OH$, wherein $R_{14}$ is $C_1$-$C_6$alkyl, preferably in the presence of a strong acid (especially sulfuric acid or hydrochloric acid), under known conditions and in analogy to, for example, M. Mamaghani et al., Asian Journal of Chemistry (2002), 14(2), 907-910. For the particular situation where $R_{14}$ is methyl, a compound of the formula VII may also be treated with acetyl chloride in methanol. R and A are as defined above.

4-Hydroxy- (or 4-mercapto-) piperidine-4-carboxylic acid derivatives of the formula V, wherein $R_{14}$ is $C_1$-$C_6$alkyl, can also be prepared by known methods from hydroxy acids of formula VIII. Esterification of VIII with an alcohol of the formula $R_{14}OH$, wherein $R_{14}$ is $C_1$-$C_6$alkyl, under thionyl chloride activation is a typical example for the preparation of hydroxy esters V, as described for example in WO09/049,851, but other known esterification methods may also be applied, like for example treatment of a compound of the formula VIII with an alcohol of the formula $R_{14}OH$ under acidic conditions (typically $H_2SO_4$ or HCl). For the particular situation where $R_{14}$ is methyl, a compound of the formula VIII may also be treated with diazomethane or trimethylsilyldiazomethane, or with acetyl chloride in methanol. The compounds VIII, VII and V can be reacted and/or isolated as free amines or amine salts (eg a hydrohalide salt, more specifically a hydrochloride or hydrobromide salt, or any other equivalent salt).

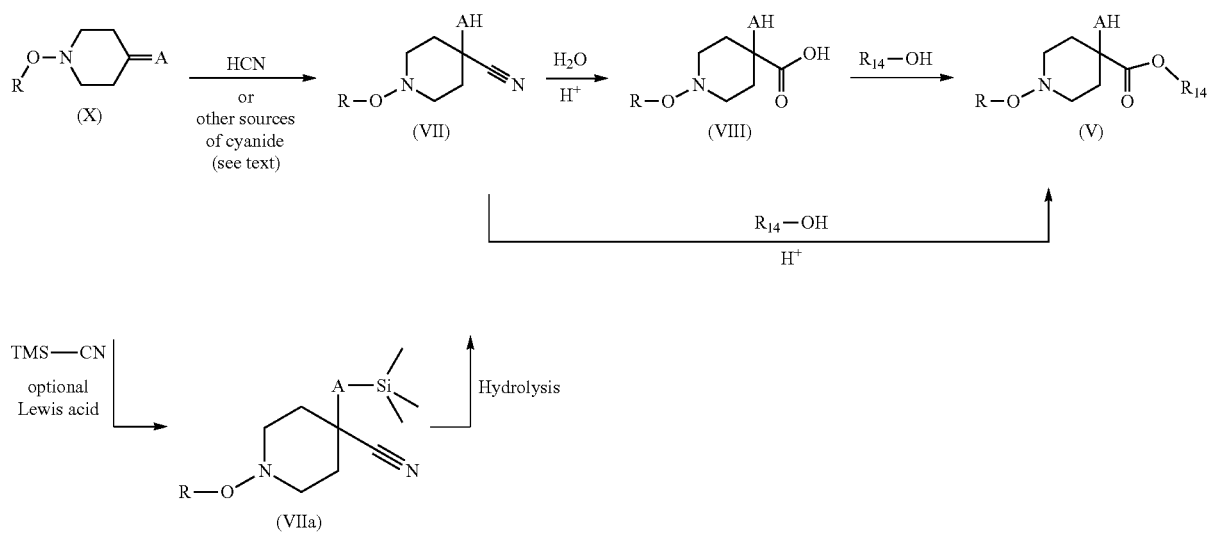

Hydroxy acids of formula VIII can be prepared from ketones of formula X by means of Strecker-type chemistry via cyanohydrins of formula VII. Hydrolysis of cyanohydrins of formula VII into hydroxy acids of formula VIII is typically performed with water under either acidic or basic conditions, preferably acidic conditions, for example in presence of hydrochloric acid or sulfuric acid. A typical example can be found, for example, in S. Liu et al., Chemistry & Biology (2007), 14(4), 409-418. Cyanohydrins of formula VII can be prepared from ketones of formula X by a number of methods, for example by treatment with hydrocyanic acid, in analogy to, for example, B. V. Unkovskii et al., Khimiya Geterotsiklicheskikh Soedinenii (1990), (10), 1359-63. Other sources of cyanide are, for example, potassium or sodium cyanide, optionally in presence of for example ammonium chloride (in analogy to, for example, I. Iriepa et al., Trends in Heterocyclic Chemistry (1999), 6, 87-95) or sodium hydrogen sulphite NaHSO$_3$ (in analogy to, for example, R. A. Y. Jones et al., J. Chem. Soc. (B), 1971, 1302-1307), or trimethylsilyl cyanide TMS-CN, acetone cyanohydrin (in analogy to, for example, A. I. Kuznetsov et al., Khimiya Geterotsiklicheskikh Soedinenii (1992), (5), 648-52) or diethylaluminum cyanide, optionally in presence of a Lewis acid, like for example, zinc chloride, zinc iodide, titanium chloride, titanium isopropoxide, ytterbium isopropoxide, magnesium bromide, boron trifluoride ethyl etherate, tetrachlorosilane or equivalents thereof. In case of treatment of ketones of formula X with trimethylsilyl cyanide TMS-CN, one may isolate the silylated cyanohydrins of the formula VIIa and subject them to hydrolysis, typically performed with water under acidic conditions, for example in presence of hydrochloric acid or sulfuric acid, in order to isolate cyanohydrins of formula VII. This path from a compound of the formula X to a derivative of the formula VII via a trimethylsilyl ether cyanohydrin intermediate VIIa can be performed in analogy to P. G. Gassman, J. J. Talley, Tetrahedron Lett. (1978), 40, 3773-3776.

For the particular situation where R$_{14}$ is methyl, a compound of the formula VIIa may also be converted directly into a compound of the formula V by treatment with acetyl chloride in methanol, in analogy to the description, for example, in M. D. Toscano et al., Chem Med Chem (2007), 2, 101-112. R and A are as defined above.

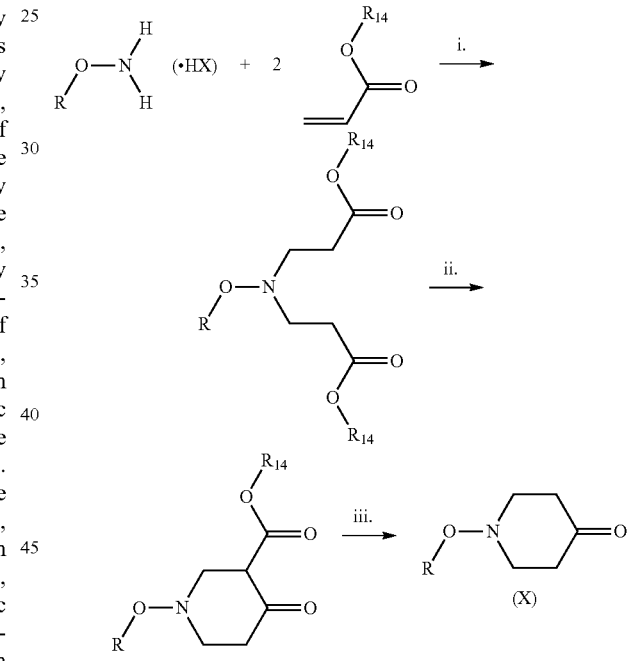

Compounds of formula X, wherein A is O and R is C$_{1-6}$alkyl, C$_{1-6}$haloalkyl, C$_2$-C$_6$alkenyl, C$_3$-C$_6$alkynyl, C$_{1-6}$cyanoalkyl, benzyl, C$_{1-4}$alkoxy(C$_{1-4}$)alkyl or C$_{1-4}$alkoxy(C$_{1-4}$)alkoxy(C$_{1-4}$)alkyl are known or can be obtained, for example, according to Major and Dursch, Journal of Organic Chemistry (1961), 26, 1867-74. The described 3 steps sequence towards compounds of the formula X involves i. reaction of an O-substituted hydroxylamine H$_2$NOR (either as free amine or amine salt, eg a hydrohalide salt HX, more specifically a hydrochloride or hydrobromide salt, or any other equivalent salt) with 2 equivalents of an acrylic ester CH$_2$=CHCOOR$_{14}$, wherein R$_{14}$ is C$_1$-C$_6$alkyl, followed by ii. a Dieckmann ester condensation and finally iii. a saponification/decarboxylation step. Preparation of appropriately O-substituted hydroxylamines of the formula H$_2$NOR (either as free amine or amine salt, eg a hydrohalide salt HX, more specifically a hydrochloride or hydrobromide salt, or any other equivalent salt) has been described in the literature, for example in B. Janza et al., Journal of Organic Chemistry (2005), 70(17), 6991-6994; or E. Bourque et al., (Genzyme Corporation, USA), PCT Int. Appl. (2008), WO 2008070758; or T. Ishikawa et al., Journal of Antibiotics (2000), 53(10), 1053-1070.

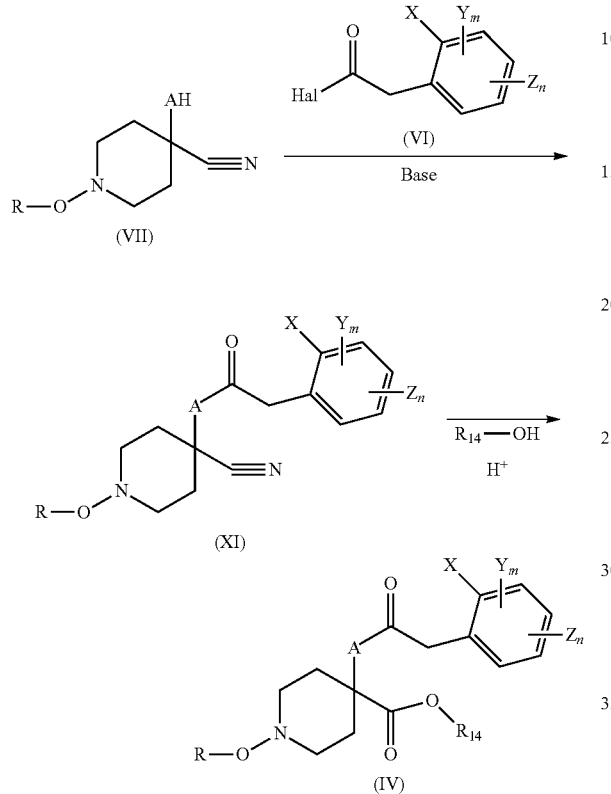

Alternatively, compounds of formula IV wherein $R_{14}$ is $C_1$-$C_6$alkyl, may be prepared by subjecting nitrile derivatives of formula XI to alcoholysis with $R_{14}$OH, preferably in acidic media (especially sulfuric acid or hydrochloric acid) by known methods described, for example, in WO 09/049,851. X, Y, Z, m, n, A and R are as defined above.

Nitrile compounds of formula XI may be themselves prepared by reacting cyanohydrins of formula VII with phenylacetyl halides of formula VI, preferably in the presence of base in a suitable solvent by known methods described, for example, in WO 09/049,851. X, Y, Z, m, n, A and R are as defined above. The base may be inorganic such as an alkali metal carbonate or hydroxide or a metal hydride, or an organic base such as a tertiary amine or metal alkoxide. Examples of suitable inorganic bases include sodium carbonate, sodium or potassium hydroxide, sodium hydride, and suitable organic bases include trialkylamines such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent.

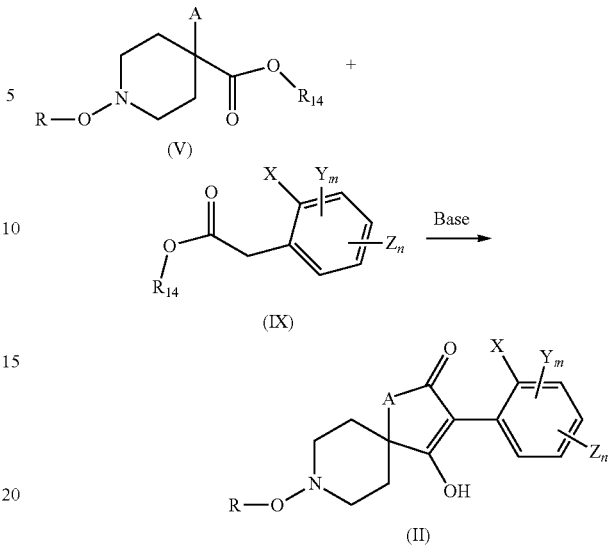

Alternatively, compounds of formula II may be prepared directly in a 'one pot' procedure by reacting 4-hydroxy- (or 4-mercapto-) piperidine-4-carboxylic acid derivatives of the formula V with substituted phenyl-acetic acid alkyl esters of the formula IX, wherein $R_{14}$ is $C_1$-$C_6$alkyl, in the presence of a base and in a suitable solvent, as described, for example, in A. Mallinger et al., J. Org. Chem. 2009, 74, 1124-1129 or in F. Bellina et al., Eur. J. Org. Chem. 2009, 4685-4690. X, Y, Z, m, n, A and R are as defined above.

Substituted phenyl-acetic acid alkyl esters of the formula IX, wherein $R_{14}$ is $C_1$-$C_6$alkyl and in which X, Y, Z, m, n are as defined above, are known compounds or can be prepared by known methods, described for example in WO 09/049, 851.

Yet in another process, compounds of the formula II may be prepared through the debenzylation/intramolecular cyclisation of compounds of the formula XII,

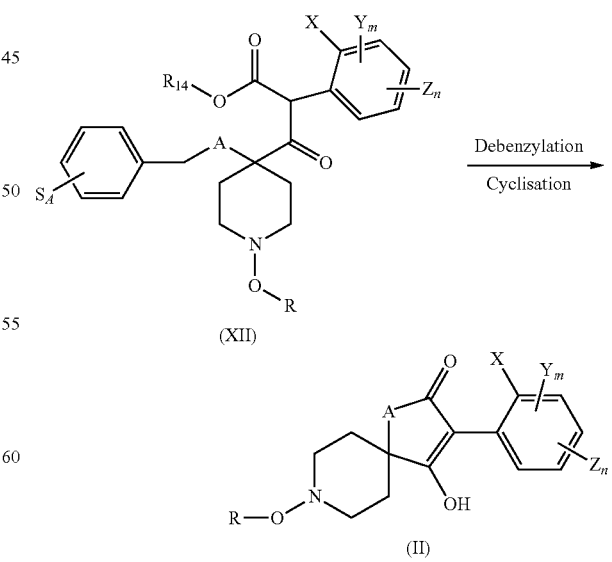

wherein $R_{14}$ is $C_1$-$C_6$alkyl and $S_A$ is hydrogen, halogen, nitro, $C_1$-$C_4$alkyl, $C_1$-$C_4$alkoxy or di($C_1$-$C_4$alkoxy), by treatment with acids or under catalytic hydrogenation conditions, optionally in the presence of a suitable solvent, and in analogy to conditions described, for example, in U.S. Pat. No. 5,945,444. Acidic treatment may typically involve, for example, sulfuric acid, hydrochloric acid, methanesulfonic acid, trifluoromethanesulfonic acid or trifluoroacetic acid. Treatment of XII with hydrogen (1-100 bars pressure) and catalytic amounts of palladium (for example palladium on carbon 1-30 wt. %) in solvents like methanol or tetrahydrofuran, optionally further containing water or acids like HCl, at 0-100° C. are typical reaction conditions for the hydrogenolytic debenzylation. X, Y, Z, m, n, A and R are as defined above.

bases, such as pyridine and triethylamine, may be employed successfully as both base and solvent. Analogous conditions have been described, for example, in U.S. Pat. No. 5,945,444. Carbonyl halides of the formula XIII, in which $R_A$ is halogen, may be prepared from the corresponding carboxylic acids XIII, wherein $R_A$ is OH, under classical and known conditions, described for example in U.S. Pat. No. 5,945,444, by reaction with halogenation agents, like phosgene, phosphorous trichloride, phosphorous pentachloride, phosphorous tribromide, phosphorous pentabromide, oxalylchloride or thionylchloride.

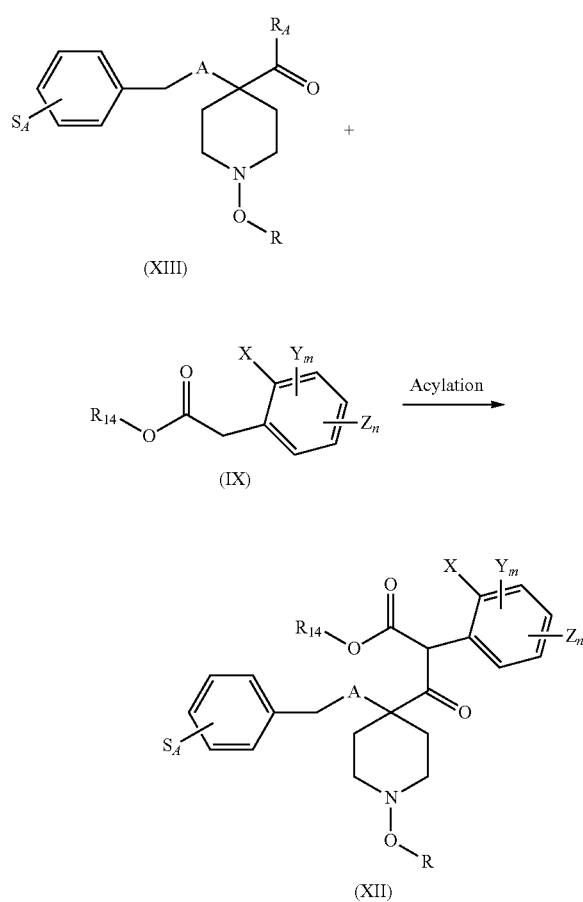

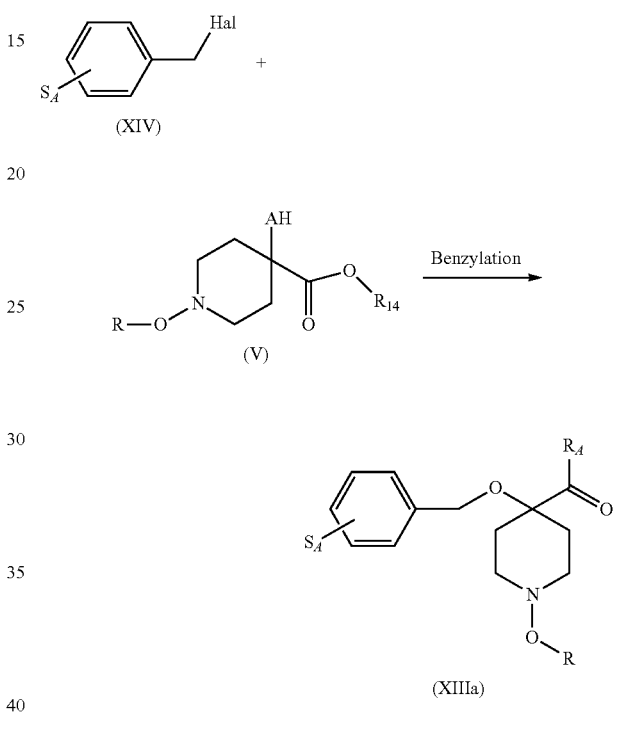

Compounds of the formula XIIIa, wherein A is O and $R_A$ is $OR_{14}$ with $R_{14}$ being $C_1$-$C_6$alkyl, may be prepared by benzylation of compounds of the formula V, wherein A is O and $R_{14}$ is $C_1$-$C_6$alkyl, with a substituted benzyl halide of the formula XIV, wherein Hal is halogen, in particular chlorine or bromine, in presence of a base in a suitable solvent, under known and standard conditions. R and $S_A$ are as defined above.

Compounds of formula XII may be prepared by acylation of a substituted phenyl-acetic acid alkyl ester of the formula IX with a carbonyl halide of the formula XIII, in which $R_A$ is halogen, in particular chlorine, preferably in the presence of base in a suitable solvent. X, Y, Z, m, n, A, R, $R_{14}$ and $S_A$ are as defined above. The base may be inorganic such as an alkali metal carbonate or hydroxide or a metal hydride, or an organic base such as a tertiary amine or metal alkoxide. Examples of suitable inorganic bases include sodium carbonate, sodium or potassium hydroxide, sodium hydride, and suitable organic bases include trialkylamines such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain Carboxylic acid compounds of the formula XIIIa, wherein A is O and $R_A$ is OH, may be prepared from the corresponding carboxylic acid esters XIIIa, wherein $R_A$ is $OR_{14}$ with $R_{14}$ being $C_1$-$C_6$alkyl, under classical and known saponification conditions, for example by treatment with base, such as NaOH, KOH or LiOH, in water or alcohols, such as methanol or ethanol, or mixtures thereof.

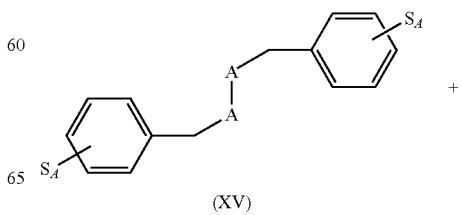

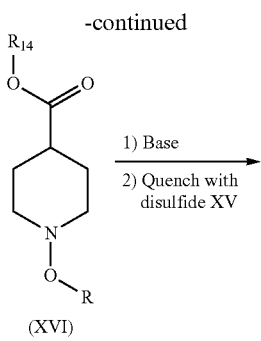

(XVI)

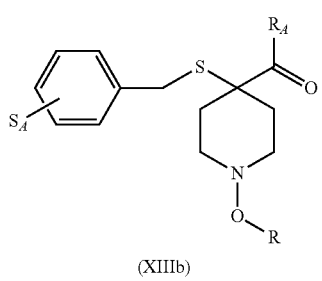

(XIIIb)

Compounds of the formula XIIIb, wherein A is S and $R_A$ is $OR_{14}$ with $R_{14}$ being $C_1$-$C_6$alkyl, may be prepared by reacting compounds of the formula XVI, wherein $R_{14}$ is $C_1$-$C_6$alkyl, first with at least one equivalent of base, such as, for example, sodium hydride, lithium diisopropylamide or potassium tert.-butoxide, in a suitable solvent, such as, for example, tetrahydrofuran, dimethoxyethane or dioxane, and then quenching the resulting anion with a disulfide of the formula XV, wherein A is S, in analogy to conditions described, for example, in U.S. Pat. No. 5,945,444. R and $S_A$ are as defined above.

Carboxylic acid compounds of the formula XIIIb, wherein A is S and $R_A$ is OH, may be prepared from the corresponding carboxylic acid esters XIIIb, wherein $R_A$ is $OR_{14}$ with $R_{14}$ being $C_1$-$C_6$alkyl, under classical and known saponification conditions, for example by treatment with base, such as NaOH, KOH or LiOH, in water or alcohols, such as methanol or ethanol, or mixtures thereof.

Esters of the formula XVI, wherein $R_{14}$ is $C_1$-$C_6$alkyl, may by prepared by reacting nitriles of the formula XVII with an alcohol of the formula $R_{14}OH$, wherein $R_{14}$ is $C_1$-$C_6$alkyl, preferably in the presence of a strong acid (especially sulfuric acid or hydrochloric acid), under known conditions. For the particular situation where $R_{14}$ is methyl, a compound of the formula XVII may also be treated with acetyl chloride in methanol. R is as defined above.

Nitriles of the formula XVII may be prepared from alcohols of the formula XX by a sequence involving alcohol activation, followed by substitution with cyanide, in suitable solvents, under known conditions. Activation of alcohol XX is, for example, performed by preparation of a mesylate, tosylate or triflate of XX by treatment with mesyl, tosyl or trifluoromethanesulfonyl halide in presence of a base, such as, for example, triethylamine or pyridine, in solvents, such as, for example, ethyl acetate, dichloromethane or ethers. Treatment of the obtained activated alcohol XX with a source of cyanide, such as, for example, sodium cyanide, potassium cyanide or tetrabutylammonium cyanide, or mixtures thereof, in solvents, such as, for example, dimethyl sulfoxide, N,N-dimethylformamide or acetonitriles, delivers the desired nitriles of the formula XVII. R is as defined above.

Alcohols of the formula XX may be prepared by treatment of the known ketones of the formula X with a reducing agent, such as, for example, sodium borohydride, lithium aluminium hydride or other metallic hydrides, in solvents, such as, for example, methanol, ethanol, isopropanol, tetrahydrofuran or ethers, under conditions known and described in the literature.

Alternatively, nitriles of the formula XVII may be prepared directly from the known ketones of the formula X upon reaction with tosylmethyl isocyanide (TosMIC) and a base, such as, for example, potassium tert-butoxide or sodium ethoxide, in nonprotic solvents, such as, for example, 1,2-dimethoxyethane (DME) or tetrahydrofuran, optionally in presence of 1 to 2 equivalents of methanol or ethanol. This one-step reductive cyanation of ketones with the use of the TosMIC reagent has been described for example in: D. and A. M. van Leusen, 'Synthetic Uses of Tosylmethyl Isocyanide (TosMIC)', Organic Reactions, Vol. 57, pp. 417-666, 2001. A typical procedure can be found on p. 479 in the above reference. R is as defined above.

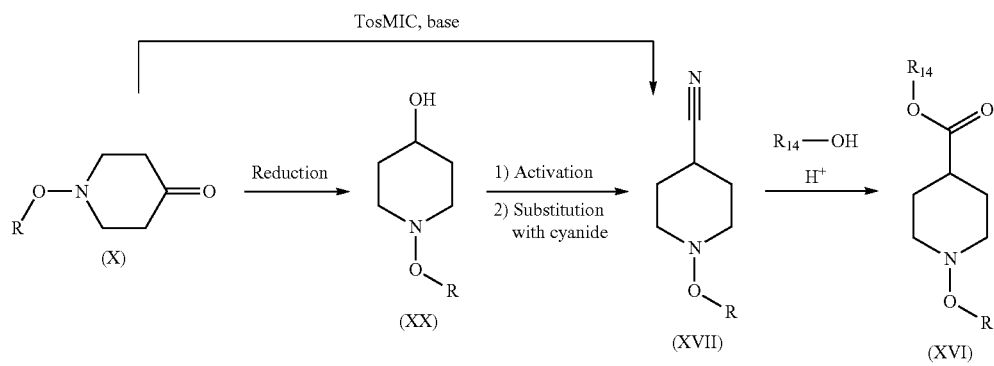

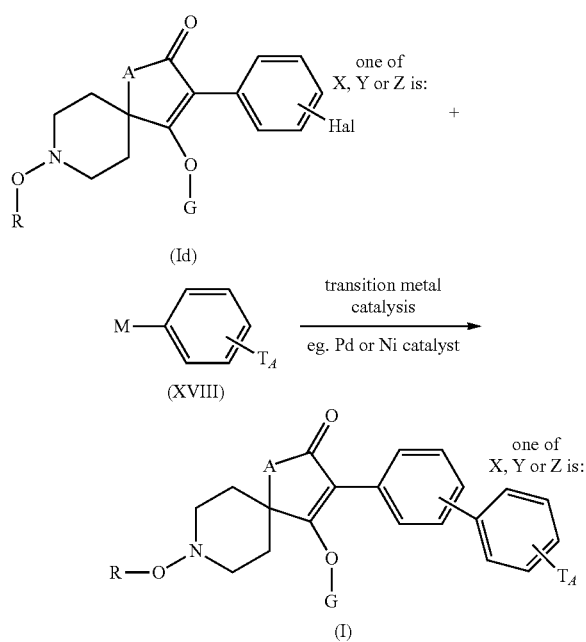

(Id)

(XVIII)

(I)

Hal is chlorine, bromine or iodine, or a pseudohalogen such as triflate
M is B, Sn, Mg, Zn, etc.. together with ligands and/or subsituents
$T_A$ is $C_{1-4}$alkyl, $C_{1-4}$haloalkyl, halogen or cyano Compounds of the formula I, wherein X, Y or Z is phenyl or phenyl substituted by $C_{1-4}$alkyl, $C_{1-4}$haloalkyl, halogen or cyano, may be prepared by reacting a corresponding halogen precursor of the formula Id, wherein Hal is chlorine, bromine, iodine or a pseudohalogen such as $C_{1-4}$haloalkylsulfonate, especially triflate, with an appropriate organometallic phenyl species of the formula XVIII, wherein $T_A$ is $C_{1-4}$alkyl, $C_{1-4}$haloalkyl, halogen or cyano and M is for example B, Sn, Si, Mg or Zn holding further ligands and/or substituents, by means of a transition metal-catalyzed reaction. The organometallic species of the formula XVIII is for example an aryl boronic acid $T_A$-Phenyl-B(OH)$_2$, or a suitable salt or ester thereof, which will react with a compound of the formula Id under palladium- or nickel-catalyzed conditions, such as for example the Suzuki-Miyaura conditions. A variety of metals, catalysts and ligands may be used in this reaction type. Reaction conditions and catalytic systems for such a transformation have been described, for example, in WO08/071,405. A, G and R are as defined above.

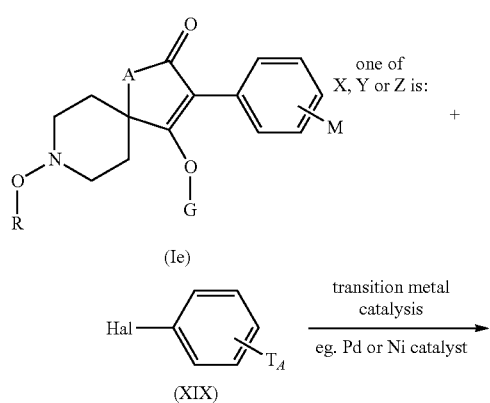

(Ie)

(XIX)

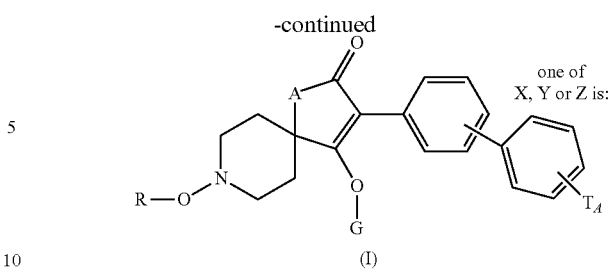

(I)

M is B, Sn, Mg, Zn, etc.. together with ligands and/or substituents
Hal is chlorine, bromine or iodine, or a pseudohalogen such as triflate
$T_A$ is $C_{1-4}$alkyl, $C_{1-4}$haloalkyl, halogen or cyano One person skilled in the art will recognize that the polarity at the two reacting centers in this cross-coupling process may be reversed. Compounds of the formula I, wherein X, Y or Z is phenyl or phenyl substituted by $C_{1-4}$alkyl, $C_{1-4}$haloalkyl, halogen or cyano, may be also prepared by reacting a corresponding organometallic species of the formula Ie, wherein M is for example B, Sn, Si, Mg or Zn holding further ligands and/or substituents, with an aryl halide of the formula XIX, wherein Hal is chlorine, bromine, iodine or a pseudohalogen such as $C_{1-4}$haloalkylsulfonate, especially triflate, by means of a transition metal-catalyzed reaction and under similar conditions as described above. A, G and R are as defined above.

Compounds of the formula IV, V, VII, VIII and XI, and salts thereof, are novel, have been specifically designed for the synthesis of the compounds of the formula I and as such form a further aspect of the invention. Thus compounds of the formula IV

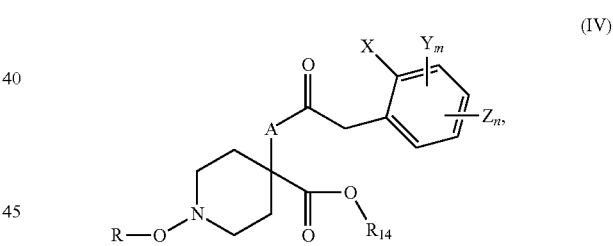

(IV)

and salts thereof, wherein X, Y, Z, m, n, A and R have the meanings assigned to them above and $R_{14}$ is $C_{1-6}$alkyl;

compounds of the formula V

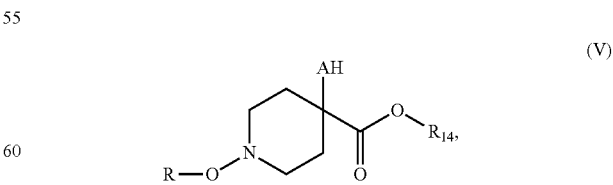

(V)

and salts thereof, wherein R and A has the meanings assigned to it above and $R_{14}$ is $C_1$-$C_6$alkyl;

compounds of the formula VIII

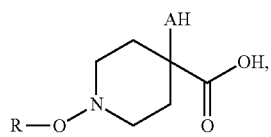

(VIII)

and salts thereof, wherein R and A has the meanings assigned to it above;
compounds of the formula XI

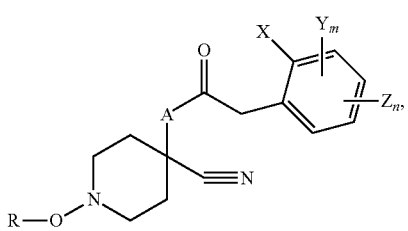

(XI)

and salts thereof, wherein X, Y, Z, m, n, A and R have the meanings assigned to them above;
compounds of the formula VII

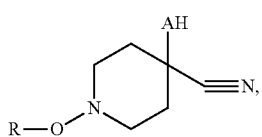

(VII)

and salts thereof, wherein R and A has the meanings assigned to it above; and
compounds of the formula XII

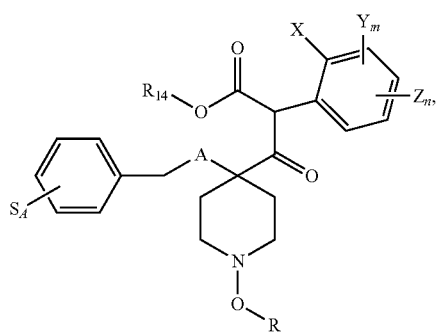

(XII)

and salts thereof, wherein X, Y, Z, m, n, A and R have the meanings assigned to them above, and wherein $R_{14}$ is $C_{1-6}$alkyl and $S_A$ is hydrogen, halogen, nitro, $C_1$-$C_4$alkyl, $C_1$-$C_4$alkoxy or di($C_1$-$C_4$alkoxy) are novel.

The remaining starting compounds and intermediates of the reaction schemes are known or can be prepared according to methods known to a person skilled in the art.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

The compounds of the formula I, wherein A is sulphur, can be prepared using methods similar to those shown above or methods generally known in the art.

A compound I can be converted in a manner known per se into another compound I by replacing one or more substituents of the starting compound I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds I can be prepared in a manner known per se. Thus, for example, acid addition salts of compounds I are obtained by treatment with a suitable acid or a suitable ion exchanger reagent and salts with bases are obtained by treatment with a suitable base or with a suitable ion exchanger reagent.

Salts of compounds I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds I can be converted in a manner known per se into other salts of compounds I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds I, which have salt-forming properties can be obtained in free form or in the form of salts.

The compounds I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 28 below can be prepared according to the methods described above. The examples which follow are intended to illustrate the invention and show preferred compounds of formula I.

Table 1: This table discloses the 145 compounds T1.001 to T1.145 of the formula Ia:

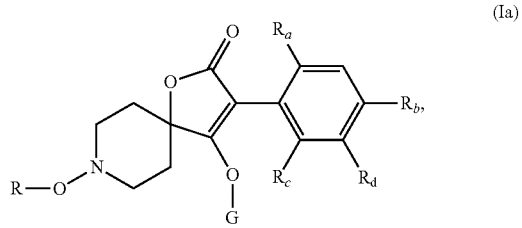

wherein R is $CH_3$, G is hydrogen and $R_a$, $R_b$, $R_c$ and $R_d$ are as defined below:

| No. | $R_a$ | $R_b$ | $R_c$ | $R_d$ |
|---|---|---|---|---|
| T1.001 | Br | H | H | H |
| T1.002 | Cl | H | H | H |
| T1.003 | $CH_3$ | H | H | H |
| T1.004 | $CH_2CH_3$ | H | H | H |
| T1.005 | $OCH_3$ | H | H | H |
| T1.006 | Br | Cl | H | H |
| T1.007 | Cl | Br | H | H |
| T1.008 | Cl | Cl | H | H |
| T1.009 | Cl | $CH_3$ | H | H |
| T1.010 | $CH_3$ | Cl | H | H |
| T1.011 | $CH_3$ | $CH_3$ | H | H |
| T1.012 | Cl | H | Cl | H |
| T1.013 | Cl | H | $CH_3$ | H |
| T1.014 | Cl | H | $CH_2CH_3$ | H |
| T1.015 | Cl | H | $OCH_3$ | H |
| T1.016 | $CH_3$ | H | $CH_3$ | H |
| T1.017 | $CH_3$ | H | $CH_2CH_3$ | H |
| T1.018 | $CH_3$ | H | $OCH_3$ | H |
| T1.019 | $CH_2CH_3$ | H | $CH_2CH_3$ | H |
| T1.020 | $CH_2CH_3$ | H | $OCH_3$ | H |
| T1.021 | $OCH_3$ | H | $OCH_3$ | H |
| T1.022 | Br | H | H | Cl |
| T1.023 | Br | H | H | $CH_3$ |
| T1.024 | Br | H | H | 4-Cl—$C_6H_4$ |
| T1.025 | Cl | H | H | Cl |
| T1.026 | Cl | H | H | $CH_3$ |
| T1.027 | Cl | H | H | 4-Cl—$C_6H_4$ |
| T1.028 | $CH_3$ | H | H | Br |
| T1.029 | $CH_3$ | H | H | Cl |
| T1.030 | $CH_3$ | H | H | $CH_3$ |
| T1.031 | $CH_3$ | H | H | $C_6H_5$ |
| T1.032 | $CH_3$ | H | H | 4-Cl—$C_6H_4$ |
| T1.033 | $CH_2CH_3$ | H | H | $CH_3$ |
| T1.034 | $CH_2CH_3$ | H | H | 4-Cl—$C_6H_4$ |
| T1.035 | $OCH_3$ | H | H | $CH_3$ |
| T1.036 | $OCH_3$ | H | H | 4-Cl—$C_6H_4$ |
| T1.037 | Cl | H | Cl | Br |
| T1.038 | $CH_3$ | H | $CH_3$ | Br |
| T1.039 | $CH_3$ | H | $CH_3$ | Cl |
| T1.040 | $CH_3$ | H | $CH_3$ | 4-Cl—$C_6H_4$ |
| T1.041 | Br | Cl | H | $CH_3$ |
| T1.042 | Br | $CH_3$ | H | $CH_3$ |
| T1.043 | Cl | Cl | H | Cl |
| T1.044 | Cl | Br | H | $CH_3$ |
| T1.045 | Cl | Cl | H | $CH_3$ |
| T1.046 | Cl | $CH_3$ | H | Cl |
| T1.047 | Cl | $CH_3$ | H | $CH_3$ |
| T1.048 | $CH_3$ | Br | H | $CH_3$ |
| T1.049 | $CH_3$ | Cl | H | $CH_3$ |
| T1.050 | $CH_3$ | $CH_3$ | H | $CH_3$ |
| T1.051 | $CH_3$ | $CH_3$ | H | 4-Cl—$C_6H_4$ |
| T1.052 | Br | Br | $CH_3$ | H |
| T1.053 | Br | Cl | $CH_3$ | H |
| T1.054 | Br | $CH_3$ | Br | H |
| T1.055 | Br | $CH_3$ | Cl | H |
| T1.056 | Cl | Br | $CH_3$ | H |
| T1.057 | Cl | Cl | Cl | H |
| T1.058 | Cl | Cl | $CH_3$ | H |
| T1.059 | Cl | $CH_3$ | Cl | H |
| T1.060 | Cl | $CH_3$ | $CH_2CH_3$ | H |

-continued

| No. | $R_a$ | $R_b$ | $R_c$ | $R_d$ |
|---|---|---|---|---|
| T1.061 | Cl | CH$_3$ | OCH$_3$ | H |
| T1.062 | Cl | 4-Cl—C$_6$H$_4$ | Cl | H |
| T1.063 | Cl | 4-Cl—C$_6$H$_4$ | CH$_3$ | H |
| T1.064 | Cl | 4-Cl—C$_6$H$_4$ | CH$_2$CH$_3$ | H |
| T1.065 | Cl | 4-Cl—C$_6$H$_4$ | OCH$_3$ | H |
| T1.066 | CH$_3$ | Br | CH$_3$ | H |
| T1.067 | CH$_3$ | Cl | CH$_3$ | H |
| T1.068 | CH$_3$ | CH$_3$ | Br | H |
| T1.069 | CH$_3$ | CH$_3$ | Cl | H |
| T1.070 | CH$_3$ | CH$_3$ | CH$_3$ | H |
| T1.071 | CH$_3$ | CH$_3$ | CH$_2$CH$_3$ | H |
| T1.072 | CH$_3$ | CH$_3$ | OCH$_3$ | H |
| T1.073 | CH$_3$ | 4-Cl—C$_6$H$_4$ | CH$_3$ | H |
| T1.074 | CH$_3$ | 4-Cl—C$_6$H$_4$ | CH$_2$CH$_3$ | H |
| T1.075 | CH$_3$ | 4-Cl—C$_6$H$_4$ | OCH$_3$ | H |
| T1.076 | CH$_2$CH$_3$ | Br | Br | H |
| T1.077 | CH$_2$CH$_3$ | Br | Cl | H |
| T1.078 | CH$_2$CH$_3$ | Br | CH$_3$ | H |
| T1.079 | CH$_2$CH$_3$ | Br | CH$_2$CH$_3$ | H |
| T1.080 | CH$_2$CH$_3$ | Br | OCH$_3$ | H |
| T1.081 | CH$_2$CH$_3$ | Cl | Br | H |
| T1.082 | CH$_2$CH$_3$ | Cl | Cl | H |
| T1.083 | CH$_2$CH$_3$ | Cl | CH$_3$ | H |
| T1.084 | CH$_2$CH$_3$ | Cl | CH$_2$CH$_3$ | H |
| T1.085 | CH$_2$CH$_3$ | Cl | OCH$_3$ | H |
| T1.086 | CH$_2$CH$_3$ | CH$_3$ | Br | H |
| T1.087 | CH$_2$CH$_3$ | CH$_3$ | Cl | H |
| T1.088 | CH$_2$CH$_3$ | CH$_3$ | CH$_2$CH$_3$ | H |
| T1.089 | CH$_2$CH$_3$ | CH$_3$ | OCH$_3$ | H |
| T1.090 | CH$_2$CH$_3$ | CH$_2$CH$_3$ | CH$_3$ | H |
| T1.091 | CH$_2$CH$_3$ | CH$_2$CH$_3$ | CH$_2$CH$_3$ | H |
| T1.092 | CH$_2$CH$_3$ | 4-Cl—C$_6$H$_4$ | Br | H |
| T1.093 | CH$_2$CH$_3$ | 4-Cl—C$_6$H$_4$ | CH$_2$CH$_3$ | H |
| T1.094 | CH$_2$CH$_3$ | 4-Cl—C$_6$H$_4$ | OCH$_3$ | H |
| T1.095 | OCH$_3$ | Br | CH$_3$ | H |
| T1.096 | OCH$_3$ | Cl | CH$_3$ | H |
| T1.097 | OCH$_3$ | CH$_3$ | Br | H |
| T1.098 | OCH$_3$ | CH$_3$ | Cl | H |
| T1.099 | OCH$_3$ | CH$_3$ | OCH$_3$ | H |
| T1.100 | OCH$_3$ | 4-Cl—C$_6$H$_4$ | OCH$_3$ | H |
| T1.101 | CH$_3$ | CH$_3$ | CH$_3$ | F |
| T1.102 | CH$_3$ | CH$_3$ | CH$_3$ | Cl |
| T1.103 | CH$_3$ | CH$_3$ | CH$_3$ | Br |
| T1.104 | CH$_3$ | CH$_3$ | CH$_3$ | CH$_3$ |
| T1.105 | CH$_3$ | CH$_3$ | CH$_3$ | 4-Cl—C$_6$H$_4$ |
| T1.106 | Cl | CH$_3$ | CH$_3$ | CH$_3$ |
| T1.107 | CH$_3$ | Cl | CH$_3$ | CH$_3$ |
| T1.108 | CH$_3$ | CH$_3$ | Cl | CH$_3$ |
| T1.109 | CH$_2$CH$_3$ | CH$_3$ | CH$_3$ | CH$_3$ |
| T1.110 | OCH$_3$ | CH$_3$ | CH$_3$ | CH$_3$ |
| T1.111 | Cyclo-C3 | CH$_3$ | CH$_3$ | CH$_3$ |
| T1.112 | CH$_3$ | CH$_3$ | Cyclo-C3 | H |
| T1.113 | CH$_3$ | F | H | Br |
| T1.114 | CH$_3$ | CH$_3$ | H | Br |
| T1.115 | CH$_2$CH$_3$ | CH$_3$ | H | CH$_3$ |
| T1.116 | OCH$_3$ | CH$_3$ | H | CH$_3$ |
| T1.117 | Cyclo-C3 | CH$_3$ | H | CH$_3$ |
| T1.118 | CH$_2$CH$_3$ | Cl | H | CH$_3$ |
| T1.119 | OCH$_3$ | Cl | H | CH$_3$ |
| T1.120 | Cyclo-C3 | Cl | H | CH$_3$ |
| T1.121 | Cl | H | CH$_3$ | CH$_3$ |
| T1.122 | CH$_3$ | H | CH$_3$ | CH$_3$ |
| T1.123 | CH$_2$CH$_3$ | H | CH$_3$ | CH$_3$ |
| T1.124 | OCH$_3$ | H | CH$_3$ | CH$_3$ |
| T1.125 | Cyclo-C3 | H | CH$_3$ | CH$_3$ |
| T1.126 | F | H | Cl | CH$_3$ |
| T1.127 | Cl | H | F | CH$_3$ |
| T1.128 | H | CH$_3$ | CH$_3$ | CH$_3$ |
| T1.129 | Br | CH$_3$ | CH$_3$ | CH$_3$ |
| T1.130 | CH$_3$ | H | Cl | CH$_3$ |
| T1.131 | CH$_3$ | H | Br | CH$_3$ |
| T1.132 | Br | H | CH$_3$ | CH$_3$ |
| T1.133 | CH$_3$ | CH=CH$_2$ | CH$_3$ | H |
| T1.134 | CH$_3$ | CH$_3$ | CH=CH$_2$ | H |
| T1.135 | CH$_3$ | C≡CH | CH$_3$ | H |
| T1.136 | CH$_3$ | CH$_3$ | C≡CH | H |
| T1.137 | CH$_3$ | I | CH$_3$ | H |
| T1.138 | CH$_3$ | CH$_3$ | I | H |
| T1.139 | CH$_3$ | CH$_3$ | H | I |
| T1.140 | CH$_3$ | CF$_3$ | CH$_3$ | H |
| T1.141 | CH$_3$ | CH$_3$ | CF$_3$ | H |
| T1.142 | CH$_3$ | CHF$_2$ | CH$_3$ | H |
| T1.143 | CH$_3$ | CH$_3$ | CHF$_2$ | H |
| T1.144 | CH$_3$ | Cyclo-C3 | CH$_3$ | H |
| T1.145 | CH=CH$_2$ | CH$_3$ | CH=CH$_2$ | H |

Cyclo-C3 means cyclopropyl.

Table 2: This table discloses the 145 compounds T2.001 to T2.145 of the formula Ia, wherein R is CH$_2$CH$_3$, G is hydrogen and R$_a$, R$_b$, R$_c$ and R$_d$ are as defined in Table 1.

Table 3: This table discloses the 145 compounds T3.001 to T3.145 of the formula Ia, wherein R is n-C$_3$H$_7$, G is hydrogen and R$_a$, R$_b$, R$_c$ and R$_d$ are as defined in Table 1.

Table 4: This table discloses the 145 compounds T4.001 to T4.145 of the formula Ia, wherein R is i-C$_3$H$_7$, G is hydrogen and R$_a$, R$_b$, R$_c$ and R$_d$ are as defined in Table 1.

Table 5: This table discloses the 145 compounds T5.001 to T5.145 of the formula Ia, wherein R is allyl, G is hydrogen and R$_a$, R$_b$, R$_c$ and R$_d$ are as defined in Table 1.

Table 6: This table discloses the 145 compounds T6.001 to T6.145 of the formula Ia, wherein R is propargyl, G is hydrogen and R$_a$, R$_b$, R$_c$ and R$_d$ are as defined in Table 1.

Table 7: This table discloses the 145 compounds T7.001 to T7.145 of the formula Ia, wherein R is benzyl, G is hydrogen and R$_a$, R$_b$, R$_c$ and R$_d$ are as defined in Table 1.

Table 8: This table discloses the 145 compounds T8.001 to T8.145 of the formula Ia, wherein R is hydrogen, G is hydrogen and R$_a$, R$_b$, R$_c$ and R$_d$ are as defined in Table 1.

Table 9: This table discloses the 145 compounds T9.001 to T9.145 of the formula Ia, wherein R is CH$_2$OCH$_3$, G is hydrogen and R$_a$, R$_b$, R$_c$ and R$_d$ are as defined in Table 1.

Table 10: This table discloses the 145 compounds T10.001 to T10.145 of the formula Ia, wherein R is CH$_2$CH$_2$OCH$_3$, G is hydrogen and R$_a$, R$_b$, R$_c$ and R$_d$ are as defined in Table 1.

Table 11: This table discloses the 145 compounds T11.001 to T11.145 of the formula Ia, wherein R is CH$_2$OCH$_2$CH$_3$, G is hydrogen and R$_a$, R$_b$, R$_c$ and R$_d$ are as defined in Table 1.

Table 12: This table discloses the 145 compounds T12.001 to T12.145 of the formula Ia, wherein R is CH$_2$OC$_2$H$_4$OCH$_3$, G is hydrogen and R$_a$, R$_b$, R$_c$ and R$_d$ are as defined in Table 1.

Table 13: This table discloses the 145 compounds T13.001 to T13.145 of the formula Ia, wherein R is CH$_2$CF$_3$, G is hydrogen and R$_a$, R$_b$, R$_c$ and R$_d$ are as defined in Table 1.

Table 14: This table discloses the 145 compounds T14.001 to T14.145 of the formula Ia, wherein R is CH$_2$CN, G is hydrogen and R$_a$, R$_b$, R$_c$ and R$_d$ are as defined in Table 1.

Table 15: This table discloses the 145 compounds T15.001 to T15.145 of the formula Ib:

(Ib)

wherein R is CH$_3$, G is hydrogen and R$_a$, R$_b$, R$_c$ and R$_d$ are as defined below:

| No. | $R_a$ | $R_b$ | $R_c$ | $R_d$ |
|---|---|---|---|---|
| T15.001 | Br | H | H | H |
| T15.002 | Cl | H | H | H |
| T15.003 | $CH_3$ | H | H | H |
| T15.004 | $CH_2CH_3$ | H | H | H |
| T15.005 | $OCH_3$ | H | H | H |
| T15.006 | Br | Cl | H | H |
| T15.007 | Cl | Br | H | H |
| T15.008 | Cl | Cl | H | H |
| T15.009 | Cl | $CH_3$ | H | H |
| T15.010 | $CH_3$ | Cl | H | H |
| T15.011 | $CH_3$ | $CH_3$ | H | H |
| T15.012 | Cl | H | Cl | H |
| T15.013 | Cl | H | $CH_3$ | H |
| T15.014 | Cl | H | $CH_2CH_3$ | H |
| T15.015 | Cl | H | $OCH_3$ | H |
| T15.016 | $CH_3$ | H | $CH_3$ | H |
| T15.017 | $CH_3$ | H | $CH_2CH_3$ | H |
| T15.018 | $CH_3$ | H | $OCH_3$ | H |
| T15.019 | $CH_2CH_3$ | H | $CH_2CH_3$ | H |
| T15.020 | $CH_2CH_3$ | H | $OCH_3$ | H |
| T15.021 | $OCH_3$ | H | $OCH_3$ | H |
| T15.022 | Br | H | H | Cl |
| T15.023 | Br | H | H | $CH_3$ |
| T15.024 | Br | H | H | 4-Cl—$C_6H_4$ |
| T15.025 | Cl | H | H | Cl |
| T15.026 | Cl | H | H | $CH_3$ |
| T15.027 | Cl | H | H | 4-Cl—$C_6H_4$ |
| T15.028 | $CH_3$ | H | H | Br |
| T15.029 | $CH_3$ | H | H | Cl |
| T15.030 | $CH_3$ | H | H | $CH_3$ |
| T15.031 | $CH_3$ | H | H | $C_6H_5$ |
| T15.032 | $CH_3$ | H | H | 4-Cl—$C_6H_4$ |
| T15.033 | $CH_2CH_3$ | H | H | $CH_3$ |
| T15.034 | $CH_2CH_3$ | H | H | 4-Cl—$C_6H_4$ |
| T15.035 | $OCH_3$ | H | H | $CH_3$ |
| T15.036 | $OCH_3$ | H | H | 4-Cl—$C_6H_4$ |
| T15.037 | Cl | H | Cl | Br |
| T15.038 | $CH_3$ | H | $CH_3$ | Br |
| T15.039 | $CH_3$ | H | $CH_3$ | Cl |
| T15.040 | $CH_3$ | H | $CH_3$ | 4-Cl—$C_6H_4$ |
| T15.041 | Br | Cl | H | $CH_3$ |
| T15.042 | Br | $CH_3$ | H | $CH_3$ |
| T15.043 | Cl | Cl | H | Cl |
| T15.044 | Cl | Br | H | $CH_3$ |
| T15.045 | Cl | Cl | H | $CH_3$ |
| T15.046 | Cl | $CH_3$ | H | Cl |
| T15.047 | Cl | $CH_3$ | H | $CH_3$ |
| T15.048 | $CH_3$ | Br | H | $CH_3$ |
| T15.049 | $CH_3$ | Cl | H | $CH_3$ |
| T15.050 | $CH_3$ | $CH_3$ | H | $CH_3$ |
| T15.051 | $CH_3$ | $CH_3$ | H | 4-Cl—$C_6H_4$ |
| T15.052 | Br | Br | $CH_3$ | H |
| T15.053 | Br | Cl | $CH_3$ | H |
| T15.054 | Br | $CH_3$ | Br | H |
| T15.055 | Br | $CH_3$ | Cl | H |
| T15.056 | Cl | Br | $CH_3$ | H |
| T15.057 | Cl | Cl | Cl | H |
| T15.058 | Cl | Cl | $CH_3$ | H |
| T15.059 | Cl | $CH_3$ | Cl | H |
| T15.060 | Cl | $CH_3$ | $CH_2CH_3$ | H |
| T15.061 | Cl | $CH_3$ | $OCH_3$ | H |
| T15.062 | Cl | 4-Cl—$C_6H_4$ | Cl | H |
| T15.063 | Cl | 4-Cl—$C_6H_4$ | $CH_3$ | H |
| T15.064 | Cl | 4-Cl—$C_6H_4$ | $CH_2CH_3$ | H |
| T15.065 | Cl | 4-Cl—$C_6H_4$ | $OCH_3$ | H |
| T15.066 | $CH_3$ | Br | $CH_3$ | H |
| T15.067 | $CH_3$ | Cl | $CH_3$ | H |
| T15.068 | $CH_3$ | $CH_3$ | Br | H |
| T15.069 | $CH_3$ | $CH_3$ | Cl | H |
| T15.070 | $CH_3$ | $CH_3$ | $CH_3$ | H |
| T15.071 | $CH_3$ | $CH_3$ | $CH_2CH_3$ | H |
| T15.072 | $CH_3$ | $CH_3$ | $OCH_3$ | H |
| T15.073 | $CH_3$ | 4-Cl—$C_6H_4$ | $CH_3$ | H |
| T15.074 | $CH_3$ | 4-Cl—$C_6H_4$ | $CH_2CH_3$ | H |
| T15.075 | $CH_3$ | 4-Cl—$C_6H_4$ | $OCH_3$ | H |
| T15.076 | $CH_2CH_3$ | Br | Br | H |
| T15.077 | $CH_2CH_3$ | Br | Cl | H |
| T15.078 | $CH_2CH_3$ | Br | $CH_3$ | H |
| T15.079 | $CH_2CH_3$ | Br | $CH_2CH_3$ | H |
| T15.080 | $CH_2CH_3$ | Br | $OCH_3$ | H |
| T15.081 | $CH_2CH_3$ | Cl | Br | H |
| T15.082 | $CH_2CH_3$ | Cl | Cl | H |
| T15.083 | $CH_2CH_3$ | Cl | $CH_3$ | H |
| T15.084 | $CH_2CH_3$ | Cl | $CH_2CH_3$ | H |
| T15.085 | $CH_2CH_3$ | Cl | $OCH_3$ | H |
| T15.086 | $CH_2CH_3$ | $CH_3$ | Br | H |
| T15.087 | $CH_2CH_3$ | $CH_3$ | Cl | H |
| T15.088 | $CH_2CH_3$ | $CH_3$ | $CH_2CH_3$ | H |
| T15.089 | $CH_2CH_3$ | $CH_3$ | $OCH_3$ | H |
| T15.090 | $CH_2CH_3$ | $CH_2CH_3$ | $CH_3$ | H |
| T15.091 | $CH_2CH_3$ | $CH_2CH_3$ | $CH_2CH_3$ | H |
| T15.092 | $CH_2CH_3$ | 4-Cl—$C_6H_4$ | Br | H |
| T15.093 | $CH_2CH_3$ | 4-Cl—$C_6H_4$ | $CH_2CH_3$ | H |
| T15.094 | $CH_2CH_3$ | 4-Cl—$C_6H_4$ | $OCH_3$ | H |
| T15.095 | $OCH_3$ | Br | $CH_3$ | H |
| T15.096 | $OCH_3$ | Cl | $CH_3$ | H |
| T15.097 | $OCH_3$ | $CH_3$ | Br | H |
| T15.098 | $OCH_3$ | $CH_3$ | Cl | H |
| T15.099 | $OCH_3$ | $CH_3$ | $OCH_3$ | H |
| T15.100 | $OCH_3$ | 4-Cl—$C_6H_4$ | $OCH_3$ | H |
| T15.101 | $CH_3$ | $CH_3$ | $CH_3$ | F |
| T15.102 | $CH_3$ | $CH_3$ | $CH_3$ | Cl |
| T15.103 | $CH_3$ | $CH_3$ | $CH_3$ | Br |
| T15.104 | $CH_3$ | $CH_3$ | $CH_3$ | $CH_3$ |
| T15.105 | $CH_3$ | $CH_3$ | $CH_3$ | 4-Cl—$C_6H_4$ |
| T15.106 | Cl | $CH_3$ | $CH_3$ | $CH_3$ |
| T15.107 | $CH_3$ | Cl | $CH_3$ | $CH_3$ |
| T15.108 | $CH_3$ | $CH_3$ | Cl | $CH_3$ |
| T15.109 | $CH_2CH_3$ | $CH_3$ | $CH_3$ | $CH_3$ |
| T15.110 | $OCH_3$ | $CH_3$ | $CH_3$ | $CH_3$ |
| T15.111 | Cyclo-C3 | $CH_3$ | $CH_3$ | $CH_3$ |
| T15.112 | $CH_3$ | $CH_3$ | Cyclo-C3 | H |
| T15.113 | $CH_3$ | F | H | Br |
| T15.114 | $CH_3$ | $CH_3$ | H | Br |
| T15.115 | $CH_2CH_3$ | $CH_3$ | H | $CH_3$ |
| T15.116 | $OCH_3$ | $CH_3$ | H | $CH_3$ |
| T15.117 | Cyclo-C3 | $CH_3$ | H | $CH_3$ |
| T15.118 | $CH_2CH_3$ | Cl | H | $CH_3$ |
| T15.119 | $OCH_3$ | Cl | H | $CH_3$ |
| T15.120 | Cyclo-C3 | Cl | H | $CH_3$ |
| T15.121 | Cl | H | $CH_3$ | $CH_3$ |
| T15.122 | $CH_3$ | H | $CH_3$ | $CH_3$ |
| T15.123 | $CH_2CH_3$ | H | $CH_3$ | $CH_3$ |
| T15.124 | $OCH_3$ | H | $CH_3$ | $CH_3$ |
| T15.125 | Cyclo-C3 | H | $CH_3$ | $CH_3$ |
| T15.126 | F | H | Cl | $CH_3$ |
| T15.127 | Cl | H | F | $CH_3$ |
| T15.128 | H | $CH_3$ | $CH_3$ | $CH_3$ |
| T15.129 | Br | $CH_3$ | $CH_3$ | $CH_3$ |
| T15.130 | $CH_3$ | H | Cl | $CH_3$ |
| T15.131 | $CH_3$ | H | Br | $CH_3$ |
| T15.132 | Br | H | $CH_3$ | $CH_3$ |
| T15.133 | $CH_3$ | $CH=CH_2$ | $CH_3$ | H |
| T15.134 | $CH_3$ | $CH_3$ | $CH=CH_2$ | H |
| T15.135 | $CH_3$ | $C\equiv CH$ | $CH_3$ | H |
| T15.136 | $CH_3$ | $CH_3$ | $C\equiv CH$ | H |
| T15.137 | $CH_3$ | I | $CH_3$ | H |
| T15.138 | $CH_3$ | $CH_3$ | I | H |
| T15.139 | $CH_3$ | $CH_3$ | H | I |
| T15.140 | $CH_3$ | $CF_3$ | $CH_3$ | H |
| T15.141 | $CH_3$ | $CH_3$ | $CF_3$ | H |
| T15.142 | $CH_3$ | $CHF_2$ | $CH_3$ | H |
| T15.143 | $CH_3$ | $CH_3$ | $CHF_2$ | H |
| T15.144 | $CH_3$ | Cyclo-C3 | $CH_3$ | H |
| T15.145 | $CH=CH_2$ | $CH_3$ | $CH=CH_2$ | H |

Cyclo-C3 means cyclopropyl.

Table 16: This table discloses the 145 compounds T16.001 to T16.145 of the formula Ia, wherein R is $CH_2CH_3$, G is hydrogen and $R_a$, $R_b$, $R_c$ and $R_d$ are as defined in Table 15.

Table 17: This table discloses the 145 compounds T17.001 to T17.145 of the formula Ia, wherein R is n-$C_3H_7$, G is hydrogen and $R_a$, $R_b$, $R_c$ and $R_d$ are as defined in Table 15.

Table 18: This table discloses the 145 compounds T18.001 to T18.145 of the formula Ia, wherein R is i-$C_3H_7$, G is hydrogen and $R_a$, $R_b$, $R_c$ and $R_d$ are as defined in Table 15.

Table 19: This table discloses the 145 compounds T19.001 to T19.145 of the formula Ia, wherein R is allyl, G is hydrogen and $R_a$, $R_b$, $R_c$ and $R_d$ are as defined in Table 15.

Table 20: This table discloses the 145 compounds T20.001 to T20.145 of the formula Ia, wherein R is propargyl, G is hydrogen and $R_a$, $R_b$, $R_c$ and $R_d$ are as defined in Table 15.

Table 21: This table discloses the 145 compounds T21.001 to T21.145 of the formula Ia, wherein R is benzyl, G is hydrogen and $R_a$, $R_b$, $R_c$ and $R_d$ are as defined in Table 15.

Table 22: This table discloses the 145 compounds T22.001 to T22.145 of the formula Ia, wherein R is hydrogen, G is hydrogen and $R_a$, $R_b$, $R_c$ and $R_d$ are as defined in Table 15.

Table 23: This table discloses the 145 compounds 123.001 to 123.145 of the formula Ia, wherein R is $CH_2OCH_3$, G is hydrogen and $R_a$, $R_b$, $R_c$ and $R_d$ are as defined in Table 15.

Table 24: This table discloses the 145 compounds T24.001 to T24.145 of the formula Ia, wherein R is $CH_2CH_2OCH_3$, G is hydrogen and $R_a$, $R_b$, $R_c$ and $R_d$ are as defined in Table 15.

Table 25: This table discloses the 145 compounds T25.001 to T25.145 of the formula Ia, wherein R is $CH_2OCH_2CH_3$, G is hydrogen and $R_a$, $R_b$, $R_c$ and $R_d$ are as defined in Table 15.

Table 26: This table discloses the 145 compounds T26.001 to T26.145 of the formula Ia, wherein R is $CH_2OC_2H_4OCH_3$, G is hydrogen and $R_a$, $R_b$, $R_c$ and $R_d$ are as defined in Table 15.

Table 27: This table discloses the 145 compounds T27.001 to T27.145 of the formula Ia, wherein R is $CH_2CF_3$, G is hydrogen and $R_a$, $R_b$, $R_c$ and $R_d$ are as defined in Table 15.

Table 28: This table discloses the 145 compounds T28.001 to T28.145 of the formula Ia, wherein R is $CH_2CN$, G is hydrogen and $R_a$, $R_b$, $R_c$ and $R_d$ are as defined in Table 15.

The compounds according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

The compounds of formula I can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula I include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. *(thrips)*, *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

Further examples of the above mentioned pests are:
from the order Acarina, for example,
*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;
from the order Anoplura, for example,
*Haematopinus* spp., *Linognathus* spp., *Pediculus* spp., *Pemphigus* spp. and *Phylloxera* spp.;
from the order Coleoptera, for example,
*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemLineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;

from the order Diptera, for example,
*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;
from the order Heteroptera, for example,
*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;
from the order Homoptera, for example,
*Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;*
from the order Hymenoptera, for example,
Acromyrmex, *Atta* spp., *Cephus* spp., *Diprion* spp., *Diprionidae, Gilpinia polytoma, Hoplocamps* spp., *Lasius* spp., *Monomorium pharaonis, Neodiprion* spp., *Solenopsis* spp. and *Vespa* spp.;
from the order Isoptera, for example,
*Reticulitermes* spp.;
from the order Lepidoptera, for example,
*Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiela, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;
from the order Mallophaga, for example,
*Damalinea* spp. and *Trichodectes* spp.;
from the order Orthoptera, for example,
*Blatta* spp., *Blattella* spp., *Gryllotalpa* spp., *Leucophaea maderae, Locusta* spp., *Periplaneta* spp. and *Schistocerca* spp.;
from the order Psocoptera, for example,
*Liposcelis* spp.;
from the order Siphonaptera, for example,
*Ceratophyllus* spp., *Ctenocephalides* spp. and *Xenopsylla cheopis;* from the order Thysanoptera, for example,
*Frankliniella* spp., *Hercinothrips* spp., *Scirtothrips aurantii, Taeniothrips* spp., *Thrips palmi* and *Thrips tabaci;* and
from the order Thysanura, for example,
*Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "crops" is also to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popliae;* or insecticidal proteins from *Bacillus thuringiensis,* such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus;* toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyltransferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard® Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/N000/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003.

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compounds and compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, the compounds and compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compounds and compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus,* and also hymenopterans such as *Sirex juvencus, Urocerus gigas, Urocerus gigas taignus* and *Urocerus augur,* and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus,* and bristletails such as *Lepisma saccharina.*

The invention therefore provides a method of combating and controlling insects, acarines, nematodes or molluscs which comprises applying an insecticidally, acaricidally, nematicidally or molluscicidally effective amount of a compound of formula I, or a composition containing a compound of formula I, to a pest, a locus of pest, or to a plant susceptible to attack by a pest, The compounds of formula I are preferably used against insects or acarines.

The term "plant" as used herein includes seedlings, bushes and trees.

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions C8 to C12 of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethyl ammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids. Further suitable phosphates are tris-esters of phosphoric acid with aliphatic or aromatic alcohols and/or bis-esters of alkyl phosphonic acids with aliphatic or aromatic alcohols, which are a high performance oil-type adjuvant. These tris-esters have been described, for example, in WO0147356, WO0056146, EP-A-0579052 or EP-A-1018299 or are commercially available under their chemical name. Preferred tris-esters of phosphoric acid for use in the new compositions are tris-(2-ethylhexyl)phosphate, tris-n-octyl phosphate and tris-butoxyethyl phosphate, where tris-(2-ethylhexyl)phosphate is most preferred. Suitable bis-ester of alkyl phosphonic acids are bis-(2-ethylhexyl)-(2-ethylhexyl)-phosphonate, bis-(2-ethylhexyl)-(n-octyl)-phosphonate, dibutyl-butyl phosphonate and bis(2-ethylhexyl)-tripropylene-phosphonate, where bis-(2-ethylhexyl)-(n-octyl)-phosphonate is particularly preferred.

The compositions according to the invention can preferably additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil such as ADIGOR® and MERO®, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Also, alkoxylated fatty acids can be used as additives in the inventive compositions as well as polymethylsiloxane based additives, which have been described in WO08/037,373.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecyl-benzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE®(Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pen-e-trate®, can also be mixed into the spray mixture as activity-enhancing agents.

As a rule, the compositions comprise 0.1 to 99%, especially 0.1 to 95%, of active ingredient of the formula I and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable Concentrates:
active ingredient: 1 to 95%, preferably 5 to 50%, more preferably 5 to 20%
surfactant: 1 to 30%, preferably 10 to 20%
solvent: 5 to 98%, preferably 70 to 85%
Dusts:
active ingredient: 0.1 to 10%, preferably 2 to 5%,
solid carrier: 99.9 to 90%, preferably 99.9 to 99%
Suspension Concentrates:
active ingredient: 5 to 75%, preferably 10 to 50%, more preferably 10 to 40%
water: 94 to 24%, preferably 88 to 30%
surfactant: 1 to 40%, preferably 2 to 30%
Oil-Based Suspension Concentrates:
active ingredient: 2 to 75%, preferably 5 to 50%, more preferably 10 to 25%
oil: 94 to 24%, preferably 88 to 30%
surfactant: 1 to 40%, preferably 2 to 30%
Wettable Powders:
active ingredient: 0.5 to 90%, preferably 1 to 80%, more preferably 25 to 75%
surfactant: 0.5 to 20%, preferably 1 to 15%
solid carrier: 5 to 99%, preferably 15 to 98%
Granulates:
active ingredient: 0.5 to 30%, preferably 3 to 25%, more preferably 3 to 15%
solid carrier: 99.5 to 70%, preferably 97 to 85%

Preferably, the term "active ingredient" refers to one of the compounds selected from Tables 1 to 28 shown above. It also refers to mixtures of the compound of formula I, in particular a compound selected from said Tables 1 to 28, with other insecticides, fungicides, herbicides, safeners, adjuvants and the like, which mixtures are specifically disclosed below.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers, in particular nitrogen containing fertilizers such as ammonium nitrates and urea as described in WO08/017,388, which can enhance the efficacy of the inventive compounds; or other active ingredients for achieving specific effects, for example ammonium or phosphonium salts, in particular halides, (hydrogen)sulphates, nitrates, (hydrogen)carbonates, citrates, tartrates, formates and acetates, as described in WO07/068,427 and WO07/068,428, which also can enhance the efficacy of the inventive compounds and which can be used in combination with penetration enhancers such as alkoxalated fatty acids; bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

Further methods of application of the compositions according to the invention comprise drip application onto the soil, dipping of parts of plants such as roots bulbs or tubers, drenching the soil, as well as soil injection. These methods are known in the art.

In order to apply a compound of formula I as an insecticide, acaricide, nematicide or molluscicide to a pest, a locus of pest, or to a plant susceptible to attack by a pest, a compound of formula I is usually formulated into a composition which includes, in addition to the compound of formula I, a suitable inert diluent or carrier and, optionally, a formulation adjuvant in form of a surface active agent (SFA) as described herein or, for example, in EP-B-1062217. SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula I. The composition is generally used for the control of pests such that a compound of formula I is applied at a rate of from 0.1 g to 10 kg per hectare, preferably from 1 g to 6 kg per hectare, more preferably from 1 g to 1 kg per hectare.

When used in a seed dressing, a compound of formula I is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula I and a suitable carrier or diluent therefor.

In a still further aspect the invention provides a method of combating and controlling pests at a locus which comprises treating the pests or the locus of the pests with an insecticidally, acaricidally, nematicidally or molluscicidally effective amount of a composition comprising a compound of formula I.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), oil-based suspension concentrate (OD), aerosols, fogging/smoke formulations, capsule suspensions (CS) and seed treatment formulations. The formulation type chosen in any instance will depend upon the particular purpose en-visaged and the physical, chemical and biological properties of the compound of formula I.

Dustable powders (DP) may be prepared by mixing a compound of formula I with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula I with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula I with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula I and one or more powdered solid diluents or carriers, or from pre-formed blank granules by absorbing a compound of formula I (or a solution thereof, in a suitable agent) in a porous granular material (such as pumice, attapulgite clays, fuller's earth, kieselguhr, diatomaceous earths or ground corn cobs) or by adsorbing a compound of formula I (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula I in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula I in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula I either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula I is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula I. SCs may be prepared by ball or bead milling the solid compound of formula I in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula I may be dry milled and added to water, containing agents hereinbefore described, to produce the desired end product.

Oil-based suspension concentrate (OD) may be prepared similarly by suspending finely divided insoluble solid particles of a compound of formula I in an organic fluid (for example at least one mineral oil or vegetable oil). ODs may further comprise at least one penetration promoter (for example an alcohol ethoxylate or a related compound), at least one non-ionic surfactants and/or at least one anionic surfactant, and optionally at least one additive from the group of emulsifiers, foam-inhibiting agents, preservatives, antioxidants, dyestuffs, and/or inert filler materials. An OD is intended and suitable for dilution with water before use to produce a spray solution with sufficient stability to allow spray application through appropriate equipment.

Aerosol formulations comprise a compound of formula I and a suitable propellant (for example n-butane). A compound of formula I may also be dissolved or dispersed in a suitable medium (for example water or a water miscible liquid, such as n-propanol) to provide compositions for use in non-pressurised, hand-actuated spray pumps.

A compound of formula I may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula I and, optionally, a carrier or diluent therefor. The polymeric shell may be produced by either an interfacial polycondensation reaction or by a coacervation procedure. The compositions may provide for controlled release of the compound of formula I and they may be used for seed treatment. A compound of formula I may also be formulated in a biodegradable polymeric matrix to provide a slow, controlled release of the compound.

A compound of formula I may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC, OD and DC compositions described above.

Compositions for treating seed may include an agent for assisting the adhesion of the composition to the seed (for example a mineral oil or a film-forming barrier).

A composition of the present invention may include one or more additives to improve the biological performance of the composition (for example by improving wetting, retention or distribution on surfaces; resistance to rain on treated surfaces; or uptake or mobility of a compound of formula I). Such additives include surface active agents (SFAs), spray additives based on oils, for example certain mineral oils, vegetable oils or natural plant oils (such as soy bean and rape seed oil), and blends of these with other bio-enhancing adjuvants (ingredients which may aid or modify the action of a compound of formula I). Increasing the effect of a compound of formula I may for example be achieved by adding ammonium and/or phosphonium salts, and/or optionally at least one penetration promotor such as fatty alcohol alkoxylates (for example rape oil methyl ester) or vegetable oil esters.

Wetting agents, dispersing agents and emulsifying agents may be surface active agents (SFAs) of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium diisopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula I may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula I may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ODs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula I (for example 0.0001 to 10%, by weight) depending upon the purpose for which they are to be used.

A compound of formula I may be used in mixtures with fertilisers (for example nitrogen-, potassium- or phosphorus-containing fertilisers, and more particularly ammonium nitrate and/or urea fertilizers). Suitable formulation types include granules of fertiliser. The mixtures suitably contain up to 25% by weight of the compound of formula I.

The invention therefore also provides a fertiliser composition comprising a fertiliser and a compound of formula I.

The compositions of this invention may contain other compounds having biological activity, for example micronutrients or compounds having fungicidal activity or which possess plant growth regulating, herbicidal, safening, insecticidal, nematicidal or acaricidal activity.

The compound of formula I may be the sole active ingredient of the composition or it may be admixed with one or more additional active ingredients such as a pesticide (insect, acarine, mollusc and nematode pesticide), fungicide, synergist, herbicide, safener or plant growth regulator where appropriate. The activity of the compositions according to the invention may thereby be broadened considerably and may have surprising advantages which can also be described, in a wider sense, as synergistic activity. An additional active ingredient may: provide a composition having a broader spectrum of activity or increased persistence at a locus; provide a composition demonstrating better plant/crop tolerance by reducing phytotoxicity; provide a composition controlling insects in their different development stages; synergise the activity or complement the activity (for example by increasing the speed of effect or overcoming repellency) of the compound of formula I; or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example etofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, or spinosad, spinetoram or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds such as imidacloprid, thiacloprid, acetamiprid, clothianidin, nitenpyram, dinotefuran or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine or pyrifluquinazon;

r) Spirotetramat, spirodiclofen or spiromesifen;

s) Flubendiamide, chloranthraliniprole, or cyanthraniliprole;

t) Cyenopyrafen or cyflumetofen; or u) Sulfoxaflor.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

The following mixtures of the compounds of formula I with active ingredients are preferred, wherein, preferably, the term "COMPOUND OF FORMULA I" refers to a compound selected from the Tables 1 to 28:

an adjuvant selected from the group of substances consisting of an oil of vegetable or animal origin, a mineral oil, alkyl esters of such oils or mixtures of such oils, and petroleum oils (alternative name) (628)+COMPOUND OF FORMULA I, an acaricide selected from the group of substances consisting of 1,1-bis(4-chlorophenyl)-2-ethoxyethanol (IUPAC name) (910)+COMPOUND OF FORMULA I, 2,4-dichlorophenylbenzenesulfonate (IUPAC/Chemical Abstracts name) (1059)+COMPOUND OF FORMULA I, 2-fluoro-N-methyl-N-1-naphthylacetamide (IUPAC name) (1295)+COMPOUND OF FORMULA I, 4-chlorophenyl phenyl sulfone (IUPAC name) (981)+COMPOUND OF FORMULA I, abamectin (1)+COMPOUND OF FORMULA I, acequinocyl (3)+COMPOUND OF FORMULA I, acetoprole [CCN]+COMPOUND OF FORMULA I, acrinathrin (9)+COMPOUND OF FORMULA I, aldicarb (16)+COMPOUND OF FORMULA I, aldoxycarb (863)+COMPOUND OF FORMULA I, alpha-cypermethrin (202)+COMPOUND OF FORMULA I, amidithion (870)+COMPOUND OF FORMULA I, amidoflumet [CCN]+COMPOUND OF FORMULA I, amidothioate (872)+COMPOUND OF FORMULA I, amiton (875)+COMPOUND OF FORMULA I, amiton hydrogen oxalate (875)+COMPOUND OF FORMULA I, amitraz (24)+COMPOUND OF FORMULA I, aramite (881)+COMPOUND OF FORMULA I, arsenous oxide (882)+COMPOUND OF FORMULA I, AVI 382 (compound code)+COMPOUND OF FORMULA I, AZ 60541 (compound code)+COMPOUND OF FORMULA I, azinphos-ethyl (44)+COMPOUND OF FORMULA I, azinphos-methyl (45)+COMPOUND OF FORMULA I, azobenzene (IUPAC name) (888)+COMPOUND OF FORMULA I, azocyclotin (46)+COMPOUND OF FORMULA I, azothoate (889)+COMPOUND OF FORMULA I, benomyl (62)+COMPOUND OF FORMULA I, benoxafos (alternative name) [CCN]+COMPOUND OF FORMULA I, benzoximate (71)+COMPOUND OF FORMULA I, benzyl benzoate (IUPAC name) [CCN]+COMPOUND OF FORMULA I, bifenazate (74)+COMPOUND OF FORMULA I, bifenthrin (76)+COMPOUND OF FORMULA I, binapacryl (907)+COMPOUND OF FORMULA I, brofenvalerate (alternative name)+COMPOUND OF FORMULA I, bromocyclen (918)+COMPOUND OF FORMULA I, bromophos (920)+COMPOUND OF FORMULA I, bromophos-ethyl (921)+COMPOUND OF FORMULA I, bromopropylate (94)+COMPOUND OF FORMULA I, buprofezin (99)+COMPOUND OF FORMULA I, butocarboxim (103)+COMPOUND OF FORMULA I, butoxycarboxim (104)+COMPOUND OF FORMULA I, butylpyridaben (alternative name)+COMPOUND OF FORMULA I, calcium polysulfide (IUPAC name) (111)+COMPOUND OF FORMULA I, camphechlor (941)+COMPOUND OF FORMULA I, carbanolate (943)+COMPOUND OF FORMULA I, carbaryl (115)+COMPOUND OF FORMULA I, carbofuran (118)+COMPOUND OF FORMULA I, carbophenothion (947)+COMPOUND OF FORMULA I, CGA 50'439 (development code) (125)+COMPOUND OF FORMULA I, chinomethionat (126)+COMPOUND OF FORMULA I, chlorbenside (959)+COMPOUND OF FORMULA I, chlordimeform (964)+COMPOUND OF FORMULA I, chlordimeform hydrochloride (964)+COMPOUND OF FORMULA I, chlorfenapyr (130)+COMPOUND OF FORMULA I, chlorfenethol (968)+COMPOUND OF FORMULA I, chlorfenson (970)+COMPOUND OF FORMULA I, chlorfensulphide (971)+COMPOUND OF FORMULA I, chlorfenvinphos (131)+COMPOUND OF FORMULA I, chlorobenzilate (975)+COMPOUND OF FORMULA I, chloromebuform (977)+COMPOUND OF FORMULA I, chloromethiuron (978)+COMPOUND OF FORMULA I, chloropropylate (983)+COMPOUND OF FORMULA I, chlorpyrifos (145)+COMPOUND OF FORMULA I, chlorpyrifos-methyl (146)+COMPOUND OF FORMULA I, chlorthiophos (994)+COMPOUND OF FORMULA I, cinerin I (696)+COMPOUND OF FORMULA I, cinerin II (696)+COMPOUND OF FORMULA I, cinerins (696)+COMPOUND OF FORMULA I, clofentezine (158)+COMPOUND OF FORMULA I, closantel (alternative name) [CCN]+COMPOUND OF FORMULA I, coumaphos (174)+COMPOUND OF FORMULA I, crotamiton (alternative name) [CCN]+COMPOUND OF FORMULA I, crotoxyphos (1010)+COMPOUND OF FORMULA I, cufraneb (1013)+COMPOUND OF FORMULA I, cyanthoate (1020)+COMPOUND OF FORMULA I, cyenopyrafen [CCN]+COMPOUND OF FORMULA I, cyflumetofen (CAS Reg. No.: 400882-07-7)+COMPOUND OF FORMULA I, cyhalothrin (196)+COMPOUND OF FORMULA I, cyhexatin (199)+COMPOUND OF FORMULA I, cypermethrin (201)+COMPOUND OF FORMULA I, DCPM (1032)+COMPOUND OF FORMULA I, DDT (219)+COMPOUND OF FORMULA I, demephion (1037)+COMPOUND OF FORMULA I, demephion-O (1037)+COMPOUND OF FORMULA I, demephion-S (1037)+COMPOUND OF FORMULA I, demeton (1038)+COMPOUND OF FORMULA I, demeton-methyl (224)+COMPOUND OF FORMULA I, demeton-O (1038)+COMPOUND OF FORMULA I, demeton-O-methyl (224)+COMPOUND OF FORMULA I, demeton-S (1038)+COMPOUND OF FORMULA I, demeton-S-methyl (224)+COMPOUND OF FORMULA I, demeton-S-methylsulphon (1039)+COMPOUND OF FORMULA I, diafenthiuron (226)+COMPOUND OF FORMULA I, dialifos (1042)+COMPOUND OF FORMULA I, diazinon (227)+COMPOUND OF FORMULA I, dichlofluanid (230)+COMPOUND OF FORMULA I, dichlorvos (236)+COMPOUND OF FORMULA I, dicliphos (alternative name)+COMPOUND OF FORMULA I, dicofol (242)+COMPOUND OF FORMULA I, dicrotophos (243)+COMPOUND OF FORMULA I, dienochlor (1071)+COMPOUND OF FORMULA I, diflovidazin [CCN]+COMPOUND OF FORMULA I, dimefox (1081)+COMPOUND OF FORMULA I, dimethoate (262)+COMPOUND OF FORMULA I, dinactin (alternative name) (653)+COMPOUND OF FORMULA I, dinex (1089)+COMPOUND OF FORMULA I, dinex-diclexine (1089)+COMPOUND OF FORMULA I, dinobuton (269)+COMPOUND OF FORMULA I, dinocap (270)+COMPOUND OF FORMULA I, dinocap-4 [CCN]+COMPOUND OF FORMULA I, dinocap-6 [CCN]+COMPOUND OF FORMULA I, dinocton (1090)+COMPOUND OF FORMULA I, dinopenton (1092)+COMPOUND OF FORMULA I, dinosulfon (1097)+COMPOUND OF FORMULA I, dinoterbon (1098)+COMPOUND OF FORMULA I, dioxathion (1102)+COMPOUND OF FORMULA I, diphenyl sulfone (IUPAC name) (1103)+COMPOUND OF FORMULA I, disulfuram (alternative name) [CCN]+COMPOUND OF FORMULA I, disulfoton (278)+COMPOUND OF FORMULA I, DNOC (282)+COMPOUND OF FORMULA I, dofenapyn (1113)+COMPOUND OF FORMULA I, doramectin (alternative name) [CCN]+COMPOUND OF FORMULA I, endosulfan (294)+COMPOUND OF FORMULA I, endothion (1121)+COMPOUND OF FORMULA I, EPN (297)+COMPOUND OF FORMULA I, eprinomectin (alternative name) [CCN]+COMPOUND OF FORMULA I, ethion (309)+COMPOUND OF FORMULA I, ethoate-methyl (1134)+COMPOUND OF FORMULA I, etoxazole (320)+COMPOUND OF FORMULA I, etrimfos (1142)+COMPOUND OF FORMULA I, fenazaflor (1147)+COMPOUND OF FORMULA I, fenazaquin (328)+COMPOUND OF FORMULA I, fenbutatin oxide (330)+COMPOUND OF FORMULA I, fenothiocarb (337)+COMPOUND OF FORMULA I, fenpropathrin (342)+COMPOUND OF FORMULA I, fenpyrad (alternative name)+COMPOUND OF FORMULA I, fenpyroximate (345)+COMPOUND OF FORMULA I, fenson (1157)+COM- POUND OF FORMULA I, fentrifanil (1161)+COMPOUND OF FORMULA I, fenvalerate (349)+COMPOUND OF FORMULA I, fipronil (354)+COMPOUND OF FORMULA I, fluacrypyrim (360)+COMPOUND OF FORMULA I, fluazuron (1166)+COMPOUND OF FORMULA I, flubenzimine (1167)+COMPOUND OF FORMULA I, flucycloxuron (366)+COMPOUND OF FORMULA I, flucythrinate (367)+COMPOUND OF FORMULA I, fluenetil (1169)+COMPOUND OF FORMULA I, flufenoxuron (370)+COMPOUND OF FORMULA I, flumethrin (372)+COMPOUND OF FORMULA I, fluorbenside (1174)+COMPOUND OF FORMULA I, fluvalinate (1184)+COMPOUND OF FORMULA I, FMC 1137 (development code) (1185)+COMPOUND OF FORMULA I, formetanate (405)+COMPOUND OF FORMULA I, formetanate hydrochloride (405)+COMPOUND OF FORMULA I, formothion (1192)+COMPOUND OF FORMULA I, formparanate (1193)+COMPOUND OF FORMULA I, gamma-HCH (430)+COMPOUND OF FORMULA I, glyodin (1205)+COMPOUND OF FORMULA I, halfenprox (424)+COMPOUND OF FORMULA I, heptenophos (432)+COMPOUND OF FORMULA I, hexadecyl cyclopropanecarboxylate (IUPAC/Chemical Abstracts name) (1216)+COMPOUND OF FORMULA I, hexythiazox (441)+COMPOUND OF FORMULA I, IKA 2002 (CAS Reg. No.: 211923-74-9)+COMPOUND OF FORMULA I, iodomethane (IUPAC name) (542)+COMPOUND OF FORMULA I, isocarbophos (alternative name) (473)+COMPOUND OF FORMULA I, isopropyl O-(methoxyaminothiophosphoryl)salicylate (IUPAC name) (473)+COMPOUND OF FORMULA I, ivermectin (alternative name) [CCN]+COMPOUND OF FORMULA I, jasmolin I (696)+COMPOUND OF FORMULA I, jasmolin II (696)+COMPOUND OF FORMULA I, jodfenphos (1248)+COMPOUND OF FORMULA I, lindane (430)+COMPOUND OF FORMULA I, lufenuron (490)+COMPOUND OF FORMULA I, malathion (492)+COMPOUND OF FORMULA I, malonoben (1254)+COMPOUND OF FORMULA I, mecarbam (502)+COMPOUND OF FORMULA I, mephosfolan (1261)+COMPOUND OF FORMULA I, mesulfen (alternative name) [CCN]+COMPOUND OF FORMULA I, methacrifos (1266)+COMPOUND OF FORMULA I, methamidophos (527)+COMPOUND OF FORMULA I, methidathion (529)+COMPOUND OF FORMULA I, methiocarb (530)+COMPOUND OF FORMULA I, methomyl (531)+COMPOUND OF FORMULA I, methyl bromide (537)+COMPOUND OF FORMULA I, metolcarb (550)+COMPOUND OF FORMULA I, mevinphos (556)+COMPOUND OF FORMULA I, mexacarbate (1290)+COMPOUND OF FORMULA I, milbemectin (557)+COMPOUND OF FORMULA I, milbemycin oxime (alternative name) [CCN]+COMPOUND OF FORMULA I, mipafox (1293)+COMPOUND OF FORMULA I, monocrotophos (561)+COMPOUND OF FORMULA I, morphothion (1300)+COMPOUND OF FORMULA I, moxidectin (alternative name) [CCN]+COMPOUND OF FORMULA I, naled (567)+COMPOUND OF FORMULA I, NC-184 (compound code)+COMPOUND OF FORMULA I, NC-512 (compound code)+COMPOUND OF FORMULA I, nifluridide (1309)+COMPOUND OF FORMULA I, nikkomycins (alternative name) [CCN]+COMPOUND OF FORMULA I, nitrilacarb (1313)+COMPOUND OF FORMULA I, nitrilacarb 1:1 zinc chloride complex (1313)+COMPOUND OF FORMULA I, NNI-0101 (compound code)+COMPOUND OF FORMULA I, NNI-0250 (compound code)+COMPOUND OF FORMULA I, omethoate (594)+COMPOUND OF FORMULA I, oxamyl (602)+COMPOUND OF FORMULA I, oxydeprofos (1324)+COMPOUND OF FORMULA I, oxydisulfoton (1325)+COMPOUND OF FORMULA I, pp'-DDT (219)+COMPOUND OF FORMULA I, parathion (615)+COMPOUND OF FORMULA I, permethrin (626)+COMPOUND OF FORMULA I, petroleum oils (alternative name) (628)+COMPOUND OF FORMULA I, phenkapton (1330)+COMPOUND OF FORMULA I, phenthoate (631)+COMPOUND OF FORMULA I, phorate (636)+COMPOUND OF FORMULA I, phosalone (637)+COMPOUND OF FORMULA I, phosfolan (1338)+COMPOUND OF FORMULA I, phosmet (638)+COMPOUND OF FORMULA I, phosphamidon (639)+COMPOUND OF FORMULA I, phoxim (642)+COMPOUND OF FORMULA I, pirimiphos-methyl (652)+COMPOUND OF FORMULA I, polychloroterpenes (traditional name) (1347)+COMPOUND OF FORMULA I, polynactins (alternative name) (653)+COMPOUND OF FORMULA I, proclonol (1350)+COMPOUND OF FORMULA I, profenofos (662)+COMPOUND OF FORMULA I, promacyl (1354)+COMPOUND OF FORMULA I, propargite (671)+COMPOUND OF FORMULA I, propetamphos (673)+COMPOUND OF FORMULA I, propoxur (678)+COMPOUND OF FORMULA I, prothidathion (1360)+COMPOUND OF FORMULA I, prothoate (1362)+COMPOUND OF FORMULA I, pyrethrin I (696)+COMPOUND OF FORMULA I, pyrethrin II (696)+COMPOUND OF FORMULA I, pyrethrins (696)+COMPOUND OF FORMULA I, pyridaben (699)+COMPOUND OF FORMULA I, pyridaphenthion (701)+COMPOUND OF FORMULA I, pyrimidifen (706)+COMPOUND OF FORMULA I, pyrimitate (1370)+COMPOUND OF FORMULA I, quinalphos (711)+COMPOUND OF FORMULA I, quintiofos (1381)+COMPOUND OF FORMULA I, R-1492 (development code) (1382)+COMPOUND OF FORMULA I, RA-17 (development code) (1383)+COMPOUND OF FORMULA I, rotenone (722)+COMPOUND OF FORMULA I, schradan (1389)+COMPOUND OF FORMULA I, sebufos (alternative name)+COMPOUND OF FORMULA I, selamectin (alternative name) [CCN]+COMPOUND OF FORMULA I, SI-0009 (compound code)+COMPOUND OF FORMULA I, sophamide (1402)+COMPOUND OF FORMULA I, spirodiclofen (738)+COMPOUND OF FORMULA I, spiromesifen (739)+COMPOUND OF FORMULA I, SSI-121 (development code) (1404)+COMPOUND OF FORMULA I, sulfuram (alternative name) [CCN]+COMPOUND OF FORMULA I, sulfluramid (750)+COMPOUND OF FORMULA I, sulfotep (753)+COMPOUND OF FORMULA I, sulfur (754)+COMPOUND OF FORMULA I, SZI-121 (development code) (757)+COMPOUND OF FORMULA I, taufluvalinate (398)+COMPOUND OF FORMULA I, tebufenpyrad (763)+COMPOUND OF FORMULA I, TEPP (1417)+COMPOUND OF FORMULA I, terbam (alternative name)+COMPOUND OF FORMULA I, tetrachlorvinphos (777)+COMPOUND OF FORMULA I, tetradifon (786)+COMPOUND OF FORMULA I, tetranactin (alternative name) (653)+COMPOUND OF FORMULA I, tetrasul (1425)+COM- POUND OF FORMULA I, thiafenox (alternative name)+COMPOUND OF FORMULA I, thiocarboxime (1431)+COMPOUND OF FORMULA I, thiofanox (800)+COMPOUND OF FORMULA I, thiometon (801)+COMPOUND OF FORMULA I, thioquinox (1436)+COMPOUND OF FORMULA I, thuringiensin (alternative name) [CCN]+COMPOUND OF FORMULA I, triamiphos (1441)+COMPOUND OF FORMULA I, triarathene (1443)+COMPOUND OF FORMULA I, triazophos (820)+COMPOUND OF FORMULA I, triazuron (alternative name)+COMPOUND OF FORMULA I, trichlorfon (824)+COMPOUND OF FORMULA I, trifenofos (1455)+COMPOUND OF FORMULA I, trinactin (alternative name) (653)+COMPOUND OF FORMULA I, vamidothion (847)+COMPOUND OF FORMULA I, vaniliprole [CCN] and YI-5302 (compound code)+COMPOUND OF FORMULA I, an algicide selected from the group of substances consisting of bethoxazin [CCN]+COMPOUND OF FORMULA I, copper dioctanoate (IUPAC name) (170)+COMPOUND OF FORMULA I, copper sulfate (172)+COMPOUND OF FORMULA I, cybutryne [CCN]+COMPOUND OF FORMULA I, dichlone (1052)+COMPOUND OF FORMULA I, dichlorophen (232)+COMPOUND OF FORMULA I, endothal (295)+COMPOUND OF FORMULA I, fentin (347)+COMPOUND OF FORMULA I, hydrated lime [CCN]+COMPOUND OF FORMULA I, nabam (566)+COMPOUND OF FORMULA I, quinoclamine (714)+COMPOUND OF FORMULA I, quinonamid (1379)+COMPOUND OF FORMULA I, simazine (730)+COMPOUND OF FORMULA I, triphenyltin acetate (IUPAC name) (347) and triphenyltin hydroxide (IUPAC name) (347)+COMPOUND OF FORMULA I, an anthelmintic selected from the group of substances consisting of abamectin (1)+COMPOUND OF FORMULA I, crufomate (1011)+COMPOUND OF FORMULA I, doramectin (alternative name) [CCN]+COMPOUND OF FORMULA I, emamectin (291)+COMPOUND OF FORMULA I, emamectin benzoate (291)+COMPOUND OF FORMULA I, eprinomectin (alternative name) [CCN]+COMPOUND OF FORMULA I, ivermectin (alternative name) [CCN]+COMPOUND OF FORMULA I, milbemycin oxime (alternative name) [CCN]+COMPOUND OF FORMULA I, moxidectin (alternative name) [CCN]+COMPOUND OF FORMULA I, piperazine [CCN]+COMPOUND OF FORMULA I, selamectin (alternative name) [CCN]+COMPOUND OF FORMULA I, spinosad (737) and thiophanate (1435)+COMPOUND OF FORMULA I, an avicide selected from the group of substances consisting of chloralose (127)+COMPOUND OF FORMULA I, endrin (1122)+COMPOUND OF FORMULA I, fenthion (346)+COMPOUND OF FORMULA I, pyridin-4-amine (IUPAC name) (23) and strychnine (745)+COMPOUND OF FORMULA I, a bactericide selected from the group of substances consisting of 1-hydroxy-1H-pyridine-2-thione (IUPAC name) (1222)+COMPOUND OF FORMULA I, 4-(quinoxalin-2-ylamino)benzenesulfonamide (IUPAC name) (748)+COMPOUND OF FORMULA I, 8-hydroxyquinoline sulfate (446)+COMPOUND OF FORMULA I, bronopol (97)+COMPOUND OF FORMULA I, copper dioctanoate (IUPAC name) (170)+COMPOUND OF FORMULA I, copper hydroxide (IUPAC name) (169)+COMPOUND OF FORMULA I, cresol [CCN]+COMPOUND OF FORMULA I, dichlorophen (232)+COMPOUND OF FORMULA I, dipyrithione (1105)+COMPOUND OF FORMULA I, dodicin (1112)+COMPOUND OF FORMULA I, fenaminosulf (1144)+COMPOUND OF FORMULA I, formaldehyde (404)+COMPOUND OF FORMULA I, hydrargaphen (alternative name) [CCN]+COMPOUND OF FORMULA I, kasugamycin (483)+COMPOUND OF FORMULA I, kasugamycin hydrochloride hydrate (483)+COMPOUND OF FORMULA I, nickel bis(dimethyldithiocarbamate) (IUPAC name) (1308)+COMPOUND OF FORMULA I, nitrapyrin (580)+COMPOUND OF FORMULA I, octhilinone (590)+COMPOUND OF FORMULA I, oxolinic acid (606)+COMPOUND OF FORMULA I, oxytetracycline (611)+COMPOUND OF FORMULA I, potassium hydroxyquinoline sulfate (446)+COMPOUND OF FORMULA I, probenazole (658)+COMPOUND OF FORMULA I, streptomycin (744)+COMPOUND OF FORMULA I, streptomycin sesquisulfate (744)+COMPOUND OF FORMULA I, tecloftalam (766)+COMPOUND OF FORMULA I, and thiomersal (alternative name) [CCN]+COMPOUND OF FORMULA I, a biological agent selected from the group of substances consisting of *Adoxophyes orana* GV (alternative name) (12)+COMPOUND OF FORMULA I, *Agrobacterium radiobacter* (alternative name) (13)+COMPOUND OF FORMULA I, *Amblyseius* spp. (alternative name) (19)+COMPOUND OF FORMULA I, *Anagrapha falcifera* NPV (alternative name) (28)+COMPOUND OF FORMULA I, *Anagrus atomus* (alternative name) (29)+COMPOUND OF FORMULA I, *Aphelinus abdominalis* (alternative name) (33)+COMPOUND OF FORMULA I, *Aphidius colemani* (alternative name) (34)+COMPOUND OF FORMULA I, *Aphidoletes aphidimyza* (alternative name) (35)+COMPOUND OF FORMULA I, *Autographa californica* NPV (alternative name) (38)+COMPOUND OF FORMULA I, *Bacillus firmus* (alternative name) (48)+COMPOUND OF FORMULA I, *Bacillus sphaericus* Neide (scientific name) (49)+COMPOUND OF FORMULA I, *Bacillus thuringiensis* Berliner (scientific name) (51)+COMPOUND OF FORMULA I, *Bacillus thuringiensis* subsp. *aizawai* (scientific name) (51)+COMPOUND OF FORMULA I, *Bacillus thuringiensis* subsp. *israelensis* (scientific name) (51)+COMPOUND OF FORMULA I, *Bacillus thuringiensis* subsp. *japonensis* (scientific name) (51)+COMPOUND OF FORMULA I, *Bacillus thuringiensis* subsp. *kurstaki* (scientific name) (51)+COMPOUND OF FORMULA I, *Bacillus thuringiensis* subsp. *tenebrionis* (scientific name) (51)+COMPOUND OF FORMULA I, *Beauveria bassiana* (alternative name) (53)+COMPOUND OF FORMULA I, *Beauveria brongniartii* (alternative name) (54)+COMPOUND OF FORMULA I, *Chrysoperla carnea* (alternative name) (151)+COMPOUND OF FORMULA I, Cryptolaemus montrouzieri (alternative name) (178)+COMPOUND OF FORMULA I, *Cydia pomonella* GV (alternative name) (191)+COMPOUND OF FORMULA I, *Dacnusa sibirica* (alternative name) (212)+COMPOUND OF FORMULA I, *Diglyphus isaea* (alternative name) (254)+COMPOUND OF FORMULA I, *Encarsia formosa* (scientific name) (293)+COMPOUND OF FORMULA I, *Eretmocerus eremicus* (alternative name) (300)+COMPOUND OF FORMULA I, *Helicoverpa zea* NPV (alternative name) (431)+COMPOUND OF FORMULA I, *Heterorhabditis bacteriophora* and *H.*

*megidis* (alternative name) (433)+COMPOUND OF FORMULA I, *Hippodamia convergens* (alternative name) (442)+COMPOUND OF FORMULA I, *Leptomastix dactylopii* (alternative name) (488)+COMPOUND OF FORMULA I, *Macrolophus caliginosus* (alternative name) (491)+COMPOUND OF FORMULA I, *Mamestra brassicae* NPV (alternative name) (494)+COMPOUND OF FORMULA I, *Metaphycus helvolus* (alternative name) (522)+COMPOUND OF FORMULA I, *Metarhizium anisopliae* var. *acridum* (scientific name) (523)+COMPOUND OF FORMULA I, *Metarhizium anisopliae* var. *anisopliae* (scientific name) (523)+COMPOUND OF FORMULA I, *Neodiprion sertifer* NPV and *N. lecontei* NPV (alternative name) (575)+COMPOUND OF FORMULA I, *Onus* spp. (alternative name) (596)+COMPOUND OF FORMULA I, *Paecilomyces fumosoroseus* (alternative name) (613)+COMPOUND OF FORMULA I, *Phytoseiulus persimilis* (alternative name) (644)+COMPOUND OF FORMULA I, *Spodoptera exigua* multicapsid nuclear polyhedrosis virus (scientific name) (741)+COMPOUND OF FORMULA I, *Steinernema bibionis* (alternative name) (742)+COMPOUND OF FORMULA I, *Steinernema carpocapsae* (alternative name) (742)+COMPOUND OF FORMULA I, *Steinernema feltiae* (alternative name) (742)+COMPOUND OF FORMULA I, *Steinernema glaseri* (alternative name) (742)+COMPOUND OF FORMULA I, *Steinernema riobrave* (alternative name) (742)+COMPOUND OF FORMULA I, *Steinernema riobravis* (alternative name) (742)+COMPOUND OF FORMULA I, *Steinernema scapterisci* (alternative name) (742)+COMPOUND OF FORMULA I, *Steinernema* spp. (alternative name) (742)+COMPOUND OF FORMULA I, *Trichogramma* spp. (alternative name) (826)+COMPOUND OF FORMULA I, *Typhlodromus occidentalis* (alternative name) (844), *Verticillium lecanii* (alternative name) (848)+COMPOUND OF FORMULA I and *Xenorhabdus nematophila* (alternative name)+COMPOUND OF FORMULA I, a soil sterilant selected from the group of substances consisting of iodomethane (IUPAC name) (542) and methyl bromide (537)+COMPOUND OF FORMULA I, a chemosterilant selected from the group of substances consisting of apholate [CCN]+COMPOUND OF FORMULA I, bisazir (alternative name) [CCN]+COMPOUND OF FORMULA I, busulfan (alternative name) [CCN]+COMPOUND OF FORMULA I, diflubenzuron (250)+COMPOUND OF FORMULA I, dimatif (alternative name) [CCN]+COMPOUND OF FORMULA I, hemel [CCN]+COMPOUND OF FORMULA I, hempa [CCN]+COMPOUND OF FORMULA I, metepa [CCN]+COMPOUND OF FORMULA I, methiotepa [CCN]+COMPOUND OF FORMULA I, methyl apholate [CCN]+COMPOUND OF FORMULA I, morzid [CCN]+COMPOUND OF FORMULA I, penfluoron (alternative name) [CCN]+COMPOUND OF FORMULA I, tepa [CCN]+COMPOUND OF FORMULA I, thiohempa (alternative name) [CCN]+COMPOUND OF FORMULA I, thiotepa (alternative name) [CCN]+COMPOUND OF FORMULA I, tretamine (alternative name) [CCN] and uredepa (alternative name) [CCN]+COMPOUND OF FORMULA I, an insect pheromone selected from the group of substances consisting of (E)-dec-5-en-1-yl acetate with (E)-dec-5-en-1-ol (IUPAC name) (222)+COMPOUND OF FORMULA I, (E)-tridec-4-en-1-yl acetate (IUPAC name) (829)+COMPOUND OF FORMULA I, (E)-6-methylhept-2-en-4-ol (IUPAC name) (541)+COMPOUND OF FORMULA I, (E,Z)-tetradeca-4,10-dien-1-yl acetate (IUPAC name) (779)+COMPOUND OF FORMULA I, (Z)-dodec-7-en-1-yl acetate (IUPAC name) (285)+COMPOUND OF FORMULA I, (Z)-hexadec-1'-enal (IUPAC name) (436)+COMPOUND OF FORMULA I, (Z)-hexadec-11-en-1-yl acetate (IUPAC name) (437)+COMPOUND OF FORMULA I, (Z)-hexadec-13-en-11-yn-1-yl acetate (IUPAC name) (438)+COMPOUND OF FORMULA I, (Z)-icos-13-en-10-one (IUPAC name) (448)+COMPOUND OF FORMULA I, (Z)-tetradec-7-en-1-al (IUPAC name) (782)+COMPOUND OF FORMULA I, (Z)-tetradec-9-en-1-ol (IUPAC name) (783)+COMPOUND OF FORMULA I, (Z)-tetradec-9-en-1-yl acetate (IUPAC name) (784)+COMPOUND OF FORMULA I, (7E,9Z)-dodeca-7,9-dien-1-yl acetate (IUPAC name) (283)+COMPOUND OF FORMULA I, (9Z,11E)-tetradeca-9,11-dien-1-yl acetate (IUPAC name) (780)+COMPOUND OF FORMULA I, (9Z,12E)-tetradeca-9,12-dien-1-yl acetate (IUPAC name) (781)+COMPOUND OF FORMULA I, 14-methyloctadec-1-ene (IUPAC name) (545)+COMPOUND OF FORMULA I, 4-methylnonan-5-ol with 4-methylnonan-5-one (IUPAC name) (544)+COMPOUND OF FORMULA I, alpha-multistriatin (alternative name) [CCN]+COMPOUND OF FORMULA I, brevicomin (alternative name) [CCN]+COMPOUND OF FORMULA I, codlelure (alternative name) [CCN]+COMPOUND OF FORMULA I, codlemone (alternative name) (167)+COMPOUND OF FORMULA I, cuelure (alternative name) (179)+COMPOUND OF FORMULA I, disparlure (277)+COMPOUND OF FORMULA I, dodec-8-en-1-yl acetate (IUPAC name) (286)+COMPOUND OF FORMULA I, dodec-9-en-1-yl acetate (IUPAC name) (287)+COMPOUND OF FORMULA I, dodeca-8+COMPOUND OF FORMULA I, 10-dien-1-yl acetate (IUPAC name) (284)+COMPOUND OF FORMULA I, dominicalure (alternative name) [CCN]+COMPOUND OF FORMULA I, ethyl 4-methyloctanoate (IUPAC name) (317)+COMPOUND OF FORMULA I, eugenol (alternative name) [CCN]+COMPOUND OF FORMULA I, frontalin (alternative name) [CCN]+COMPOUND OF FORMULA I, gossyplure (alternative name) (420)+COMPOUND OF FORMULA I, grandlure (421)+COMPOUND OF FORMULA I, grandlure I (alternative name) (421)+COMPOUND OF FORMULA I, grandlure II (alternative name) (421)+COMPOUND OF FORMULA I, grandlure III (alternative name) (421)+COMPOUND OF FORMULA I, grandlure IV (alternative name) (421)+COMPOUND OF FORMULA I, hexylure [CCN]+COMPOUND OF FORMULA I, ipsdienol (alternative name) [CCN]+COMPOUND OF FORMULA I, ipsenol (alternative name) [CCN]+COMPOUND OF FORMULA I, japonilure (alternative name) (481)+COMPOUND OF FORMULA I, lineatin (alternative name) [CCN]+COMPOUND OF FORMULA I, litlure (alternative name) [CCN]+COMPOUND OF FORMULA I, looplure (alternative name) [CCN]+COMPOUND OF FORMULA I, medlure [CCN]+COMPOUND OF FORMULA I, megatomoic acid (alternative name) [CCN]+COMPOUND OF FORMULA I, methyl eugenol (alternative name) (540)+COMPOUND OF FORMULA I, muscalure (563)+COMPOUND OF FORMULA I, octadeca-2,13-dien-1-yl acetate (IUPAC name) (588)+COMPOUND OF FORMULA I, octadeca-3,13-dien-1-yl acetate (IUPAC name) (589)+COMPOUND OF FORMULA I, orfralure (alternative name) [CCN]+COMPOUND OF FORMULA I, oryctalure (alternative name) (317)+COMPOUND OF FORMULA I, ostramone (alternative name) [CCN]+COMPOUND OF FORMULA I, siglure [CCN]+COMPOUND OF FORMULA I, sordidin (alternative name) (736)+COMPOUND OF FORMULA I, sulcatol (alternative name) [CCN]+COMPOUND OF FORMULA I, tetradec-11-en-1-yl acetate (IUPAC name) (785)+COMPOUND OF FORMULA I, trimedlure (839)+COMPOUND OF FORMULA I, trimedlure A (alternative name) (839)+COMPOUND OF FORMULA I, trimedlure $B_1$ (alternative name) (839)+COMPOUND OF FORMULA I, trimedlure $B_2$ (alternative name) (839)+COMPOUND OF FORMULA I, trimedlure C (alternative name) (839) and trunc-call (alternative name) [CCN]+COMPOUND OF FORMULA I, an insect repellent selected from the group of substances consisting of 2-(octylthio)-ethanol (IUPAC name) (591)+COMPOUND OF FORMULA I, butopyronoxyl (933)+COMPOUND OF FORMULA I, butoxy (polypropylene glycol) (936)+COMPOUND OF FORMULA I, dibutyl adipate (IUPAC name) (1046)+COMPOUND OF FORMULA I, dibutyl phthalate (1047)+COMPOUND OF FORMULA I, dibutyl succinate (IUPAC name) (1048)+COMPOUND OF FORMULA I, diethyltoluamide [CCN]+COMPOUND OF FORMULA I, dimethyl carbate [CCN]+COMPOUND OF FORMULA I, dimethyl phthalate [CCN]+COMPOUND OF FORMULA I, ethyl hexanediol (1137)+COMPOUND OF FORMULA I, hexamide [CCN]+COMPOUND OF FORMULA I, methoquin-butyl (1276)+COMPOUND OF FORMULA I, methylneodecanamide [CCN]+COMPOUND OF FORMULA I, oxamate [CCN] and picaridin [CCN]+COMPOUND OF FORMULA I, an insecticide selected from the group of substances consisting of 1-dichloro-1-nitroethane (IUPAC/Chemical Abstracts name) (1058)+COMPOUND OF FORMULA I, 1,1-dichloro-2,2-bis(4-ethylphenyl)ethane (IUPAC name) (1056), +COMPOUND OF FORMULA I, 1,2-dichloropropane (IUPAC/Chemical Abstracts name) (1062)+COMPOUND OF FORMULA I, 1,2-dichloropropane with 1,3-dichloropropene (IUPAC name) (1063)+COMPOUND OF FORMULA I, 1-bromo-2-chloroethane (IUPAC/Chemical Abstracts name) (916)+COMPOUND OF FORMULA I, 2,2,2-trichloro-1-(3,4-dichlorophenyl)ethyl acetate (IUPAC name) (1451)+COMPOUND OF FORMULA I, 2,2-dichlorovinyl 2-ethylsulfinylethyl methyl phosphate (IUPAC name) (1066)+COMPOUND OF FORMULA I, 2-(1,3-dithiolan-2-yl)phenyl dimethylcarbamate (IUPAC/Chemical Abstracts name) (1109)+COMPOUND OF FORMULA I, 2-(2-butoxyethoxy)ethyl thiocyanate (IUPAC/Chemical Abstracts name) (935)+COMPOUND OF FORMULA I, 2-(4,5-dimethyl-1,3-dioxolan-2-yl)phenyl methylcarbamate (IUPAC/Chemical Abstracts name) (1084)+COMPOUND OF FORMULA I, 2-(4-chloro-3,5-xylyloxy)ethanol (IUPAC name) (986)+COMPOUND OF FORMULA I, 2-chlorovinyl diethyl phosphate (IUPAC name) (984)+COMPOUND OF FORMULA I, 2-imidazolidone (IUPAC name) (1225)+COMPOUND OF FORMULA I, 2-isovalerylindan-1,3-dione (IUPAC name) (1246)+COMPOUND OF FORMULA I, 2-methyl(prop-2-ynyl)aminophenyl methylcarbamate (IUPAC name) (1284)+COMPOUND OF FORMULA I, 2-thiocyanatoethyl laurate (IUPAC name) (1433)+COMPOUND OF FORMULA I, 3-bromo-1-chloroprop-1-ene (IUPAC name) (917)+COMPOUND OF FORMULA I, 3-methyl-1-phenylpyrazol-5-yl dimethylcarbamate (IUPAC name) (1283)+COMPOUND OF FORMULA I, 4-methyl (prop-2-ynyl)amino-3,5-xylyl methylcarbamate (IUPAC name) (1285)+COMPOUND OF FORMULA I, 5,5-dimethyl-3-oxocyclohex-1-enyl dimethylcarbamate (IUPAC name) (1085)+COMPOUND OF FORMULA I, abamectin (1)+COMPOUND OF FORMULA I, acephate (2)+COMPOUND OF FORMULA I, acetamiprid (4)+COMPOUND OF FORMULA I, acethion (alternative name) [CCN]+COMPOUND OF FORMULA I, acetoprole [CCN]+COMPOUND OF FORMULA I, acrinathrin (9)+COMPOUND OF FORMULA I, acrylonitrile (IUPAC name) (861)+COMPOUND OF FORMULA I, alanycarb (15)+COMPOUND OF FORMULA I, aldicarb (16)+COMPOUND OF FORMULA I, aldoxycarb (863)+COMPOUND OF FORMULA I, aldrin (864)+COMPOUND OF FORMULA I, allethrin (17)+COMPOUND OF FORMULA I, allosamidin (alternative name) [CCN]+COMPOUND OF FORMULA I, allyxycarb (866)+COMPOUND OF FORMULA I, alpha-cypermethrin (202)+COMPOUND OF FORMULA I, alpha-ecdysone (alternative name) [CCN]+COMPOUND OF FORMULA I, alpha-endosulfan [CCN]+COMPOUND OF FORMULA I, aluminium phosphide (640)+COMPOUND OF FORMULA I, amidithion (870)+COMPOUND OF FORMULA I, amidothioate (872)+COMPOUND OF FORMULA I, aminocarb (873)+COMPOUND OF FORMULA I, amiton (875)+COMPOUND OF FORMULA I, amiton hydrogen oxalate (875)+COMPOUND OF FORMULA I, amitraz (24)+COMPOUND OF FORMULA I, anabasine (877)+COMPOUND OF FORMULA I, athidathion (883)+COMPOUND OF FORMULA I, AVI 382 (compound code)+COMPOUND OF FORMULA I, AZ 60541 (compound code)+COMPOUND OF FORMULA I, azadirachtin (alternative name) (41)+COMPOUND OF FORMULA I, azamethiphos (42)+COMPOUND OF FORMULA I, azinphos-ethyl (44)+COMPOUND OF FORMULA I, azinphos-methyl (45)+COMPOUND OF FORMULA I, azothoate (889)+COMPOUND OF FORMULA I, *Bacillus thuringiensis* delta endotoxins (alternative name) (52)+COMPOUND OF FORMULA I, barium hexafluorosilicate (alternative name) [CCN]+COMPOUND OF FORMULA I, barium polysulfide (IUPAC/Chemical Abstracts name) (892)+COMPOUND OF FORMULA I, barthrin [CCN]+COMPOUND OF FORMULA I, Bayer 22/190 (development code) (893)+COMPOUND OF FORMULA I, Bayer 22408 (development code) (894)+COMPOUND OF FORMULA I, bendiocarb (58)+COMPOUND OF FORMULA I, benfuracarb (60)+COMPOUND OF FORMULA I, bensultap (66)+COMPOUND OF FORMULA I, beta-cyfluthrin (194)+COMPOUND OF FORMULA I, beta-cypermethrin (203)+COMPOUND OF FORMULA I, bifenthrin (76)+COMPOUND OF FORMULA I, bioallethrin (78)+COMPOUND OF FORMULA I, bioallethrin S-cyclopentenyl isomer (alternative name) (79)+COMPOUND OF FORMULA I, bioethanomethrin [CCN]+COMPOUND OF FORMULA I, biopermethrin (908)+COMPOUND OF FORMULA I, bioresmethrin (80)+COMPOUND OF FORMULA I, bis(2- chloroethyl)ether (IUPAC name) (909)+COMPOUND OF FORMULA I, bistrifluoron (83)+COMPOUND OF FORMULA I, borax (86)+COMPOUND. OF FORMULA I, brofenvalerate (alternative name)+COMPOUND OF FORMULA I, bromfenvinfos (914)+COMPOUND OF FORMULA I, bromocyclen (918)+COMPOUND OF FORMULA I, bromo-DDT (alternative name) [CCN]+COMPOUND OF FORMULA I, bromophos (920)+COMPOUND OF FORMULA I, bromophos-ethyl (921)+COMPOUND OF FORMULA I, bufencarb (924)+COMPOUND OF FORMULA I, buprofezin (99)+COMPOUND OF FORMULA I, butacarb (926)+COMPOUND OF FORMULA I, butathiofos (927)+COMPOUND OF FORMULA I, butocarboxim (103)+COMPOUND OF FORMULA I, butonate (932)+COMPOUND OF FORMULA I, butoxycarboxim (104)+COMPOUND OF FORMULA I, butylpyridaben (alternative name)+COMPOUND OF FORMULA I, cadusafos (109)+COMPOUND OF FORMULA I, calcium arsenate [CCN]+COMPOUND OF FORMULA I, calcium cyanide (444)+COMPOUND OF FORMULA I, calcium polysulfide (IUPAC name) (111)+COMPOUND OF FORMULA I, camphechlor (941)+COMPOUND OF FORMULA I, carbanolate (943)+COMPOUND OF FORMULA I, carbaryl (115)+COMPOUND OF FORMULA I, carbofuran (118)+COMPOUND OF FORMULA I, carbon disulfide (IUPAC/Chemical Abstracts name) (945)+COMPOUND OF FORMULA I, carbon tetrachloride (IUPAC name) (946)+COMPOUND OF FORMULA I, carbophenothion (947)+COMPOUND OF FORMULA I, carbosulfan (119)+COMPOUND OF FORMULA I, cartap (123)+COMPOUND OF FORMULA I, cartap hydrochloride (123)+COMPOUND OF FORMULA I, cevadine (alternative name) (725)+COMPOUND OF FORMULA I, chlorantraniliprole [CCN]+COMPOUND OF FORMULA I, chlorbicyclen (960)+COMPOUND OF FORMULA I, chlordane (128)+COMPOUND OF FORMULA I, chlordecone (963)+COMPOUND OF FORMULA I, chlordimeform (964)+COMPOUND OF FORMULA I, chlordimeform hydrochloride (964)+COMPOUND OF FORMULA I, chlorethoxyfos (129)+COMPOUND OF FORMULA I, chlorfenapyr (130)+COMPOUND OF FORMULA I, chlorfenvinphos (131)+COMPOUND OF FORMULA I, chlorfluazuron (132)+COMPOUND OF FORMULA I, chlormephos (136)+COMPOUND OF FORMULA I, chloroform [CCN]+COMPOUND OF FORMULA I, chloropicrin (141)+COMPOUND OF FORMULA I, chlorphoxim (989)+COMPOUND OF FORMULA I, chiorprazophos (990)+COMPOUND OF FORMULA I, chlorpyrifos (145)+COMPOUND OF FORMULA I, chlorpyrifos-methyl (146)+COMPOUND OF FORMULA I, chlorthiophos (994)+COMPOUND OF FORMULA I, chromafenozide (150)+COMPOUND OF FORMULA I, cinerin I (696)+COMPOUND OF FORMULA I, cinerin II (696)+COMPOUND OF FORMULA I, cinerins (696)+COMPOUND OF FORMULA I, cis-resmethrin (alternative name)+COMPOUND OF FORMULA I, cismethrin (80)+COMPOUND OF FORMULA I, clocythrin (alternative name)+COMPOUND OF FORMULA I, cloethocarb (999)+COMPOUND OF FORMULA I, closantel (alternative name) [CCN]+COMPOUND OF FORMULA I, clothianidin (165)+COMPOUND OF FORMULA I, copper acetoarsenite [CCN]+COMPOUND OF FORMULA I, copper arsenate [CCN]+COMPOUND OF FORMULA I, copper oleate [CCN]+COMPOUND OF FORMULA I, coumaphos (174)+COMPOUND OF FORMULA I, coumithoate (1006)+COMPOUND OF FORMULA I, crotamiton (alternative name) [CCN]+COMPOUND OF FORMULA I, crotoxyphos (1010)+COMPOUND OF FORMULA I, crufomate (1011)+COMPOUND OF FORMULA I, cryolite (alternative name) (177)+COMPOUND OF FORMULA I, CS 708 (development code) (1012)+COMPOUND OF FORMULA I, cyanofenphos (1019)+COMPOUND OF FORMULA I, cyanophos (184)+COMPOUND OF FORMULA I, cyanthoate (1020)+COMPOUND OF FORMULA I, cyantraniliprole [CCN]+COMPOUND OF FORMULA I, cyclethrin [CCN]+COMPOUND OF FORMULA I, cycloprothrin (188)+COMPOUND OF FORMULA I, cyfluthrin (193)+COMPOUND OF FORMULA I, cyhalothrin (196)+COMPOUND OF FORMULA I, cypermethrin (201)+COMPOUND OF FORMULA I, cyphenothrin (206)+COMPOUND OF FORMULA I, cyromazine (209)+COMPOUND OF FORMULA I, cythioate (alternative name) [CCN]+COMPOUND OF FORMULA I, d-limonene (alternative name) [CCN]+COMPOUND OF FORMULA I, d-tetramethrin (alternative name) (788)+COMPOUND OF FORMULA I, DAEP (1031)+COMPOUND OF FORMULA I, dazomet (216)+COMPOUND OF FORMULA I, DDT (219)+COMPOUND OF FORMULA I, decarbofuran (1034)+COMPOUND OF FORMULA I, deltamethrin (223)+COMPOUND OF FORMULA I, demephion (1037)+COMPOUND OF FORMULA I, demephion-O (1037)+COMPOUND OF FORMULA I, demephion-S (1037)+COMPOUND OF FORMULA I, demeton (1038)+COMPOUND OF FORMULA I, demeton-methyl (224)+COMPOUND OF FORMULA I, demeton-O (1038)+COMPOUND OF FORMULA I, demeton-O-methyl (224)+COMPOUND OF FORMULA I, demeton-S (1038)+COMPOUND OF FORMULA I, demeton-S-methyl (224)+COMPOUND OF FORMULA I, demeton-S-methylsulphon (1039)+COMPOUND OF FORMULA I, diafenthiuron (226)+COMPOUND OF FORMULA I, dialifos (1042)+COMPOUND OF FORMULA I, diamidafos (1044)+COMPOUND OF FORMULA I, diazinon (227)+COMPOUND OF FORMULA I, dicapthon (1050)+COMPOUND OF FORMULA I, dichlofenthion (1051)+COMPOUND OF FORMULA I, dichlorvos (236)+COMPOUND OF FORMULA I, dicliphos (alternative name)+COMPOUND OF FORMULA I, dicresyl (alternative name) [CCN]+COMPOUND OF FORMULA I, dicrotophos (243)+COMPOUND OF FORMULA I, dicyclanil (244)+COMPOUND OF FORMULA I, dieldrin (1070)+COMPOUND OF FORMULA I, diethyl 5-methylpyrazol-3-yl phosphate (IUPAC name) (1076)+COMPOUND OF FORMULA I, diflubenzuron (250)+COMPOUND OF FORMULA I, dilor (alternative name) [CCN]+COMPOUND OF FORMULA I, dimefluthrin [CCN]+COMPOUND OF FORMULA I, dimefox (1081)+COMPOUND OF FORMULA I, dimetan (1085)+COMPOUND OF FORMULA I, dimethoate (262)+COMPOUND OF FORMULA I, dimethrin (1083)+COMPOUND OF FORMULA I, dimethylvinphos (265)+COMPOUND OF FORMULA I, dimetilan (1086)+COMPOUND OF FORMULA I, dinex (1089)+COMPOUND OF FORMULA I, dinex-diclexine (1089)+COMPOUND OF FORMULA I, dinoprop (1093)+COMPOUND OF FORMULA I, dinosam (1094)+COMPOUND OF FORMULA I, dinoseb (1095)+COMPOUND OF FORMULA I, dinotefuran (271)+COMPOUND OF FORMULA I, diofenolan (1099)+COMPOUND OF FORMULA I, dioxabenzofos (1100)+COMPOUND OF FORMULA I, dioxacarb (1101)+COMPOUND OF FORMULA I, dioxathion (1102)+COMPOUND OF FORMULA I, disulfoton (278)+COMPOUND OF FORMULA I, dithicrofos (1108)+COMPOUND OF FORMULA I, DNOC (282)+COMPOUND OF FORMULA I, doramectin (alternative name) [CCN]+COMPOUND OF FORMULA I, DSP (1115)+COMPOUND OF FORMULA I, ecdysterone (alternative name) [CCN]+COMPOUND OF FORMULA I, EI 1642 (development code) (1118)+COMPOUND OF FORMULA I, emamectin (291)+COMPOUND OF FORMULA I, emamectin benzoate (291)+COMPOUND OF FORMULA I, EMPC (1120)+COMPOUND OF FORMULA I, empenthrin (292)+COMPOUND OF FORMULA I, endosulfan (294)+COMPOUND OF FORMULA I, endothion (1121)+COMPOUND OF FORMULA I, endrin (1122)+COMPOUND OF FORMULA I, EPBP (1123)+COMPOUND OF FORMULA I, EPN (297)+COMPOUND OF FORMULA I, epofenonane (1124)+COMPOUND OF FORMULA I, eprinomectin (alternative name) [CCN]+COMPOUND OF FORMULA I, esfenvalerate (302)+COMPOUND OF FORMULA I, etaphos (alternative name) [CCN]+COMPOUND OF FORMULA I, ethiofencarb (308)+COMPOUND OF FORMULA I, ethion (309)+COMPOUND OF FORMULA I, ethiprole (310)+COMPOUND OF FORMULA I, ethoate-methyl (1134)+COMPOUND OF FORMULA I, ethoprophos (312)+COMPOUND OF FORMULA I, ethyl formate (IUPAC name) [CCN]+COMPOUND OF FORMULA I, ethyl-DDD (alternative name) (1056)+COMPOUND OF FORMULA I, ethylene dibromide (316)+COMPOUND OF FORMULA I, ethylene dichloride (chemical name) (1136)+COMPOUND OF FORMULA I, ethylene oxide [CCN]+COMPOUND OF FORMULA I, etofenprox (319)+COMPOUND OF FORMULA I, etrimfos (1142)+COMPOUND OF FORMULA I, EXD (1143)+COMPOUND OF FORMULA I, famphur (323)+COMPOUND OF FORMULA I, fenamiphos (326)+COMPOUND OF FORMULA I, fenazaflor (1147)+COMPOUND OF FORMULA I, fenchlorphos (1148)+COMPOUND OF FORMULA I, fenethacarb (1149)+COMPOUND OF FORMULA I, fenfluthrin (1150)+COMPOUND OF FORMULA I, fenitrothion (335)+COMPOUND OF FORMULA I, fenobucarb (336)+COMPOUND OF FORMULA I, fenoxacrim (1153)+COMPOUND OF FORMULA I, fenoxycarb (340)+COMPOUND OF FORMULA I, fenpirithrin (1155)+COMPOUND OF FORMULA I, fenpropathrin (342)+COMPOUND OF FORMULA I, fenpyrad (alternative name)+COMPOUND OF FORMULA I, fensulfothion (1158)+COMPOUND OF FORMULA I, fenthion (346)+COMPOUND OF FORMULA I, fenthion-ethyl [CCN]+COMPOUND OF FORMULA I, fenvalerate (349)+COMPOUND OF FORMULA I, fipronil (354)+COMPOUND OF FORMULA I, flonicamid (358)+COMPOUND OF FORMULA I, flubendiamide (CAS. Reg. No.: 272451-65-7)+COMPOUND OF FORMULA I, flucofuron (1168)+COMPOUND OF FORMULA I, flucycloxuron (366)+COMPOUND OF FORMULA I, flucythrinate (367)+COMPOUND OF FORMULA I, fluenetil (1169)+COMPOUND OF FORMULA I, flufenerim [CCN]+COMPOUND OF FORMULA I, flufenoxuron (370)+COMPOUND OF FORMULA I, flufenprox (1171)+COMPOUND OF FORMULA I, flumethrin (372)+COMPOUND OF FORMULA I, fluvalinate (1184)+COMPOUND OF FORMULA I, FMC 1137 (development code) (1185)+COMPOUND OF FORMULA I, fonofos (1191)+COMPOUND OF FORMULA I, formetanate (405)+COMPOUND OF FORMULA I, formetanate hydrochloride (405)+COMPOUND OF FORMULA I, formothion (1192)+COMPOUND OF FORMULA I, formparanate (1193)+COMPOUND OF FORMULA I, fosmethilan (1194)+COMPOUND OF FORMULA I, fospirate (1195)+COMPOUND OF FORMULA I, fosthiazate (408)+COMPOUND OF FORMULA I, fosthietan (1196)+COMPOUND OF FORMULA I, furathiocarb (412)+COMPOUND OF FORMULA I, furethrin (1200)+COMPOUND OF FORMULA I, gamma-cyhalothrin (197)+COMPOUND OF FORMULA I, gamma-HCH (430)+COMPOUND OF FORMULA I, guazatine (422)+COMPOUND OF FORMULA I, guazatine acetates (422)+COMPOUND OF FORMULA I, GY-81 (development code) (423)+COMPOUND OF FORMULA I, halfenprox (424)+COMPOUND OF FORMULA I, halofenozide (425)+COMPOUND OF FORMULA I, HCH (430)+COMPOUND OF FORMULA I, HEOD (1070)+COMPOUND OF FORMULA I, heptachlor (1211)+COMPOUND OF FORMULA I, heptenophos (432)+COMPOUND OF FORMULA I, heterophos [CCN]+COMPOUND OF FORMULA I, hexaflumuron (439)+COMPOUND OF FORMULA I, HHDN (864)+COMPOUND OF FORMULA I, hydramethylnon (443)+COMPOUND OF FORMULA I, hydrogen cyanide (444)+COMPOUND OF FORMULA I, hydroprene (445)+COMPOUND OF FORMULA I, hyquincarb (1223)+COMPOUND OF FORMULA I, imidacloprid (458)+COMPOUND OF FORMULA I, imiprothrin (460)+COMPOUND OF FORMULA I, indoxacarb (465)+COMPOUND OF FORMULA I, iodomethane (IUPAC name) (542)+COMPOUND OF FORMULA I, IPSP (1229)+COMPOUND OF FORMULA I, isazofos (1231)+COMPOUND OF FORMULA I, isobenzan (1232)+COMPOUND OF FORMULA I, isocarbophos (alternative name) (473)+COMPOUND OF FORMULA I, isodrin (1235)+COMPOUND OF FORMULA I, isofenphos (1236)+COMPOUND OF FORMULA I, isolane (1237)+COMPOUND OF FORMULA I, isoprocarb (472)+COMPOUND OF FORMULA I, isopropyl O-(methoxyaminothiophosphoryl)salicylate (IUPAC name) (473)+COMPOUND OF FORMULA I, isoprothiolane (474)+COMPOUND OF FORMULA I, isothioate (1244)+COMPOUND OF FORMULA I, isoxathion (480)+COMPOUND OF FORMULA I, ivermectin (alternative name) [CCN]+COMPOUND OF FORMULA I, jasmolin I (696)+COMPOUND OF FORMULA I, jasmolin 11(696)+COMPOUND OF FORMULA I, jodfenphos (1248)+COMPOUND OF FORMULA I, juvenile hormone I (alternative name) [CCN]+COMPOUND OF FORMULA I, juvenile hormone II (alternative name) [CCN]+COMPOUND OF FORMULA I, juvenile hormone III (alternative name) [CCN]+COMPOUND OF FORMULA I, kelevan (1249)+COMPOUND OF FORMULA I, kinoprene (484)+COMPOUND OF FORMULA I, lambda-cyhalothrin (198)+COMPOUND OF FORMULA I, lead arsenate [CCN]+COMPOUND OF FORMULA I, lepimectin (CCN)+COMPOUND OF FORMULA I, leptophos (1250)+COMPOUND OF FORMULA I, lindane (430)+COMPOUND OF FORMULA I, lirimfos (1251)+COMPOUND OF FORMULA I, lufenuron (490)+COMPOUND OF FORMULA I, lythidathion (1253)+COMPOUND OF FORMULA I, m-cumenyl methylcarbamate (IUPAC name) (1014)+COMPOUND OF FORMULA I, magnesium phosphide (IUPAC name) (640)+COMPOUND OF FORMULA I, malathion (492)+COMPOUND OF FORMULA I, malonoben (1254)+COMPOUND OF FORMULA I, mazidox (1255)+COMPOUND OF FORMULA I, mecarbam (502)+COMPOUND OF FORMULA I, mecarphon (1258)+COMPOUND OF FORMULA I, menazon (1260)+COMPOUND OF FORMULA I, mephosfolan (1261)+COMPOUND OF FORMULA I, mercurous chloride (513)+COMPOUND OF FORMULA I, mesulfenfos (1263)+COMPOUND OF FORMULA I, metaflumizone (CCN)+COMPOUND OF FORMULA I, metam (519)+COMPOUND OF FORMULA I, metam-potassium (alternative name) (519)+COMPOUND OF FORMULA I, metam-sodium (519)+COMPOUND OF FORMULA I, methacrifos (1266)+COMPOUND OF FORMULA I, methamidophos (527)+COMPOUND OF FORMULA I, methanesulfonyl fluoride (IUPAC/Chemical Abstracts name) (1268)+COMPOUND OF FORMULA I, methidathion (529)+COMPOUND OF FORMULA I, methiocarb (530)+COMPOUND OF FORMULA I, methocrotophos (1273)+COMPOUND OF FORMULA I, methomyl (531)+COMPOUND OF FORMULA I, methoprene (532)+COMPOUND OF FORMULA I, methoquin-butyl (1276)+COMPOUND OF FORMULA I, methothrin (alternative name) (533)+COMPOUND OF FORMULA I, methoxychlor (534)+COMPOUND OF FORMULA I, methoxyfenozide (535)+COMPOUND OF FORMULA I, methyl bromide (537)+COMPOUND OF FORMULA I, methyl isothiocyanate (543)+COMPOUND OF FORMULA I, methylchloroform (alternative name) [CCN]+COMPOUND OF FORMULA I, methylene chloride [CCN]+COMPOUND OF FORMULA I, metofluthrin [CCN]+COMPOUND OF FORMULA I, metolcarb (550)+COMPOUND OF FORMULA I, metoxadiazone (1288)+COMPOUND OF FORMULA I, mevinphos (556)+COMPOUND OF FORMULA I, mexacarbate (1290)+COMPOUND OF FORMULA I, milbemectin (557)+COMPOUND OF FORMULA I, milbemycin oxime (alternative name) [CCN]+COMPOUND OF FORMULA I, mipafox (1293)+COMPOUND OF FORMULA I, mirex (1294)+COMPOUND OF FORMULA I, monocrotophos (561)+COMPOUND OF FORMULA I, morphothion (1300)+COMPOUND OF FORMULA I, moxidectin (alternative name) [CCN]+COMPOUND OF FORMULA I, naftalofos (alternative name) [CCN]+COMPOUND OF FORMULA I, naled (567)+COMPOUND OF FORMULA I, naphthalene (IUPAC/Chemical Abstracts name) (1303)+COMPOUND OF FORMULA I, NC-170 (development code) (1306)+COMPOUND OF FORMULA I, NC-184 (compound code)+COMPOUND OF FORMULA I, nicotine (578)+COMPOUND OF FORMULA I, nicotine sulfate (578)+COMPOUND OF FORMULA I, nifluridide (1309)+COMPOUND OF FORMULA I, nitenpyram (579)+COMPOUND OF FORMULA I, nithiazine (1311)+COMPOUND OF FORMULA I, nitrilacarb (1313)+COMPOUND OF FORMULA I, nitrilacarb 1:1 zinc chloride complex (1313)+COMPOUND OF FORMULA I, NNI-0101 (compound code)+COMPOUND OF FORMULA I, NNI-0250 (compound code)+COMPOUND OF FORMULA I, nornicotine (traditional name) (1319)+COMPOUND OF FORMULA I, novaluron (585)+COMPOUND OF FORMULA I, noviflumuron (586)+COMPOUND OF FORMULA I, O-5-dichloro-4-iodophenyl O-ethyl ethylphosphonothioate (IUPAC name) (1057)+COMPOUND OF FORMULA I, O,O-diethyl O-4-methyl-2-oxo-2H-chromen-7-yl phosphorothioate (IUPAC name) (1074)+COMPOUND OF FORMULA I, O,O-diethyl O-6-methyl-2-propylpyrimidin-4-yl phosphorothioate (IUPAC name) (1075)+COMPOUND OF FORMULA I, O,O,O',O'-tetrapropyl dithiopyrophosphate (IUPAC name) (1424)+COMPOUND OF FORMULA I, oleic acid (IUPAC name) (593)+COMPOUND OF FORMULA I, omethoate (594)+COMPOUND OF FORMULA I, oxamyl (602)+COMPOUND OF FORMULA I, oxydemeton-methyl (609)+COMPOUND OF FORMULA I, oxydeprofos (1324)+COMPOUND OF FORMULA I, oxydisulfoton (1325)+COMPOUND OF FORMULA I, pp'-DDT (219)+COMPOUND OF FORMULA I, para-dichlorobenzene [CCN]+COMPOUND OF FORMULA I, parathion (615)+COMPOUND OF FORMULA I, parathion-methyl (616)+COMPOUND OF FORMULA I, penfluoron (alternative name) [CCN]+COMPOUND OF FORMULA I, pentachlorophenol (623)+COMPOUND OF FORMULA I, pentachlorophenyl laurate (IUPAC name) (623)+COMPOUND OF FORMULA I, permethrin (626)+COMPOUND OF FORMULA I, petroleum oils (alternative name) (628)+COMPOUND OF FORMULA I, PH 60-38 (development code) (1328)+COMPOUND OF FORMULA I, phenkapton (1330)+COMPOUND OF FORMULA I, phenothrin (630)+COMPOUND OF FORMULA I, phenthoate (631)+COMPOUND OF FORMULA I, phorate (636)+COMPOUND OF FORMULA I, phosalone (637)+COMPOUND OF FORMULA I, phosfolan (1338)+COMPOUND OF FORMULA I, phosmet (638)+COMPOUND OF FORMULA I, phosnichlor (1339)+COMPOUND OF FORMULA I, phosphamidon (639)+COMPOUND OF FORMULA I, phosphine (IUPAC name) (640)+COMPOUND OF FORMULA I, phoxim (642)+COMPOUND OF FORMULA I, phoxim-methyl (1340)+COMPOUND OF FORMULA I, pirimetaphos (1344)+COMPOUND OF FORMULA I, pirimicarb (651)+COMPOUND OF FORMULA I, pirimiphos-ethyl (1345)+COMPOUND OF FORMULA I, pirimiphos-methyl (652)+COMPOUND OF FORMULA I, polychlorodicyclopentadiene isomers (IUPAC name) (1346)+COMPOUND OF FORMULA I, polychloroterpenes (traditional name) (1347)+COMPOUND OF FORMULA I, potassium arsenite [CCN]+COMPOUND OF FORMULA I, potassium thiocyanate [CCN]+COMPOUND OF FORMULA I, prallethrin (655)+COMPOUND OF FORMULA I, precocene I (alternative name) [CCN]+COMPOUND OF FORMULA I, precocene II (alternative name) [CCN]+COMPOUND OF FORMULA I, precocene III (alternative name) [CCN]+COMPOUND OF FORMULA I, primidophos (1349)+COMPOUND OF FORMULA I, profenofos (662)+COMPOUND OF FORMULA I, profluthrin [CCN]+COMPOUND OF FORMULA I, promacyl (1354)+COMPOUND OF FORMULA I, promecarb (1355)+COMPOUND OF FORMULA I, propaphos (1356)+COMPOUND OF FORMULA I, propetamphos (673)+COMPOUND OF FORMULA I, propoxur (678)+COMPOUND OF FORMULA I, prothidathion (1360)+COMPOUND OF FORMULA I, prothiofos (686)+COMPOUND OF FORMULA I, prothoate (1362)+COMPOUND OF FORMULA I, protrifenbute [CCN]+COMPOUND OF FORMULA I, pymetrozine (688)+COMPOUND OF FORMULA I, pyraclofos (689)+COMPOUND OF FORMULA I, pyrafluprole [CCN]+COMPOUND OF FORMULA I, pyrazophos (693)+COMPOUND OF FORMULA I, pyresmethrin (1367)+COMPOUND OF FORMULA I, pyrethrin I (696)+COMPOUND OF FORMULA I, pyrethrin 11(696)+COMPOUND OF FORMULA I, pyrethrins (696)+COMPOUND OF FORMULA I, pyridaben (699)+COMPOUND OF FORMULA I, pyridalyl (700)+COMPOUND OF FORMULA I, pyridaphenthion (701)+COMPOUND OF FORMULA I, pyrifluquinazon [CCN]+COMPOUND OF FORMULA I, pyrimidifen (706)+COMPOUND OF FORMULA I, pyrimitate (1370)+COMPOUND OF FORMULA I, pyriprole [CCN]+COMPOUND OF FORMULA I, pyriproxyfen (708)+COMPOUND OF FORMULA I, quassia (alternative name) [CCN]+COMPOUND OF FORMULA I, quinalphos (711)+COMPOUND OF FORMULA I, quinalphos-methyl (1376)+COMPOUND OF FORMULA I, quinothion (1380)+COMPOUND OF FORMULA I, quintiofos (1381)+COMPOUND OF FORMULA I, R-1492 (development code) (1382)+COMPOUND OF FORMULA I, rafoxanide (alternative name) [CCN]+COMPOUND OF FORMULA I, resmethrin (719)+COMPOUND OF FORMULA I, rotenone (722)+COMPOUND OF FORMULA I, RU 15525 (development code) (723)+COMPOUND OF FORMULA I, RU 25475 (development code) (1386)+COMPOUND OF FORMULA I, ryania (alternative name) (1387)+COMPOUND OF FORMULA I, ryanodine (traditional name) (1387)+COMPOUND OF FORMULA I, sabadilla (alternative name) (725)+COMPOUND OF FORMULA I, schradan (1389)+COMPOUND OF FORMULA I, sebufos (alternative name)+COMPOUND OF FORMULA I, selamectin (alternative name) [CCN]+COMPOUND OF FORMULA I, SI-0009 (compound code)+COMPOUND OF FORMULA I, SI-0205 (compound code)+COMPOUND OF FORMULA I, SI-0404 (compound code)+COMPOUND OF FORMULA I, SI-0405 (compound code)+COMPOUND OF FORMULA I, silafluofen (728)+COMPOUND OF FORMULA I, SN 72129 (development code) (1397)+COMPOUND OF FORMULA I, sodium arsenite [CCN]+COMPOUND OF FORMULA I, sodium cyanide (444)+COMPOUND OF FORMULA I, sodium fluoride (IUPAC/Chemical Abstracts name) (1399)+COMPOUND OF FORMULA I, sodium hexafluorosilicate (1400)+COMPOUND OF FORMULA I, sodium pentachlorophenoxide (623)+COMPOUND OF FORMULA I, sodium selenate (IUPAC name) (1401)+COMPOUND OF FORMULA I, sodium thiocyanate [CCN]+COMPOUND OF FORMULA I, sophamide (1402)+COMPOUND OF FORMULA I, spinetoram [CCN]+COMPOUND OF FORMULA I, spinosad (737)+COMPOUND OF FORMULA I, spiromesifen (739)+COMPOUND OF FORMULA I, spirotetramat [CCN]+COMPOUND OF FORMULA I, sulcofuron (746)+COMPOUND OF FORMULA I, sulcofuron-sodium (746)+COMPOUND OF FORMULA I, sulfluramid (750)+COMPOUND OF FORMULA I, sulfotep (753)+COMPOUND OF FORMULA I, sulfoxaflor [CCN]+COMPOUND OF FORMULA I, sulfuryl fluoride (756)+COMPOUND OF FORMULA I, sulprofos (1408)+COMPOUND OF FORMULA I, tar oils (alternative name) (758)+COMPOUND OF FORMULA I, tau-fluvalinate (398)+COMPOUND OF FORMULA I, tazimcarb (1412)+COMPOUND OF FORMULA I, TDE (1414)+COMPOUND OF FORMULA I, tebufenozide (762)+COMPOUND OF FORMULA I, tebufenpyrad (763)+COMPOUND OF FORMULA I, tebupirimfos (764)+COMPOUND OF FORMULA I, teflubenzuron (768)+COMPOUND OF FORMULA I, tefluthrin (769)+COMPOUND OF FORMULA I, temephos (770)+COMPOUND OF FORMULA I, TEPP (1417)+COMPOUND OF FORMULA I, terallethrin (1418)+COMPOUND OF FORMULA I, terbam (alternative name)+COMPOUND OF FORMULA I, terbufos (773)+COMPOUND OF FORMULA I, tetrachloroethane [CCN]+COMPOUND OF FORMULA I, tetrachlorvinphos (777)+COMPOUND OF FORMULA I, tetramethrin (787)+COMPOUND OF FORMULA I, tetramethylfluthrin (CAS. Reg. No.: 84937-88-2)+COMPOUND OF FORMULA I, theta-cypermethrin (204)+COMPOUND OF FORMULA I, thiacloprid (791)+COMPOUND OF FORMULA I, thiafenox (alternative name)+COMPOUND OF FORMULA I, thiamethoxam (792)+COMPOUND OF FORMULA I, thicrofos (1428)+COMPOUND OF FORMULA I, thiocarboxime (1431)+COMPOUND OF FORMULA I, thiocyclam (798)+COMPOUND OF FORMULA I, thiocyclam hydrogen oxalate (798)+COMPOUND OF FORMULA I, thiodicarb (799)+COMPOUND OF FORMULA I, thiofanox (800)+COMPOUND OF FORMULA I, thiometon (801)+COMPOUND OF FORMULA I, thionazin (1434)+COMPOUND OF FORMULA I, thiosultap (803)+COMPOUND OF FORMULA I, thiosultap-sodium (803)+COMPOUND OF FORMULA I, thuringiensin (alternative name) [CCN]+COMPOUND OF FORMULA I, tolfenpyrad (809)+COMPOUND OF FORMULA I, tralomethrin (812)+COMPOUND OF FORMULA I, transfluthrin (813)+COMPOUND OF FORMULA I, transpermethrin (1440)+COMPOUND OF FORMULA I, triamiphos (1441)+COMPOUND OF FORMULA I, triazamate (818)+COMPOUND OF FORMULA I, triazophos (820)+COMPOUND OF FORMULA I, triazuron (alternative name)+COMPOUND OF FORMULA I, trichlorfon (824)+COMPOUND OF FORMULA I, trichlormetaphos-3 (alternative name) [CCN]+COMPOUND OF FORMULA I, trichloronat (1452)+COMPOUND OF FORMULA I, trifenofos (1455)+COMPOUND OF FORMULA I, triflumuron (835)+COMPOUND OF FORMULA I, trimethacarb (840)+COMPOUND OF FORMULA I, triprene (1459)+COMPOUND OF FORMULA I, vamidothion (847)+COMPOUND OF FORMULA I, vaniliprole [CCN]+COMPOUND OF FORMULA I, veratridine (alternative name) (725)+COMPOUND OF FORMULA I, veratrine (alternative name) (725)+COMPOUND OF FORMULA I, XMC (853)+COMPOUND OF FORMULA I, xylylcarb (854)+COMPOUND OF FORMULA I, yl-5302 (compound code)+COMPOUND OF FORMULA I, zeta-cypermethrin (205)+COMPOUND OF FORMULA I, zetamethrin (alternative name)+COMPOUND OF FORMULA I, zinc phosphide (640)+COMPOUND OF FORMULA I, zolaprofos (1469) and ZXI 8901 (development code) (858)+COMPOUND OF FORMULA I, a molluscicide selected from the group of substances consisting of bis(tributyltin) oxide (IUPAC name) (913)+COMPOUND OF FORMULA I, bromoacetamide [CCN]+COMPOUND OF FORMULA I, calcium arsenate [CCN]+COMPOUND OF FORMULA I, cloethocarb (999)+COMPOUND OF FORMULA I, copper acetoarsenite [CCN]+COMPOUND OF FORMULA I, copper sulfate (172)+COMPOUND OF FORMULA I, fentin (347)+COMPOUND OF FORMULA I, ferric phosphate (IUPAC name) (352)+COMPOUND OF FORMULA I, metaldehyde (518)+COMPOUND OF FORMULA I, methiocarb (530)+COMPOUND OF FORMULA I, niclosamide (576)+COMPOUND OF FORMULA I, niclosamide-olamine (576)+COMPOUND OF FORMULA I, pentachlorophenol (623)+COMPOUND OF FORMULA I, sodium pentachlorophenoxide (623)+COMPOUND OF FORMULA I, tazimcarb (1412)+COMPOUND OF FORMULA I, thiodicarb (799)+COMPOUND OF FORMULA I, tralopyril [CCN]+COMPOUND OF FORMULA I, tributyltin oxide (913)+COMPOUND OF FORMULA I, trifenmorph (1454)+COMPOUND OF FORMULA I, trimethacarb (840)+COMPOUND OF FORMULA I, triphenyltin acetate (IUPAC name) (347) and triphenyltin hydroxide (IUPAC name) (347)+COMPOUND OF FORMULA I, a nematicide selected from the group of substances consisting of AKD-3088 (compound code)+COMPOUND OF FORMULA I, 1,2-dibromo-3-chloropropane (IUPAC/Chemical Abstracts name) (1045)+COMPOUND OF FORMULA I, 1,2-dichloropropane (IUPAC/Chemical Abstracts name) (1062)+COMPOUND OF FORMULA I, 1,2-dichloropropane with 1,3-dichloropropene (IUPAC name) (1063)+COMPOUND OF FORMULA I, 1,3-dichloropropene (233)+COMPOUND OF FORMULA I, 3,4-dichlorotetrahydrothiophene 1,1-dioxide (IUPAC/Chemical Abstracts name) (1065)+COMPOUND OF FORMULA I, 3-(4-chlorophenyl)-5-methylrhodanine (IUPAC name) (980)+COMPOUND OF FORMULA I, 5-methyl-6-thioxo-1,3,5-thiadiazinan-3-ylacetic acid (IUPAC name) (1286)+COMPOUND OF FORMULA I, 6-isopentenylaminopurine (alternative name) (210)+COMPOUND OF FORMULA I, abamectin (1)+COMPOUND OF FORMULA I, acetoprole [CCN]+COMPOUND OF FORMULA I, alanycarb (15)+COMPOUND OF FORMULA I, aldicarb (16)+COMPOUND OF FORMULA I, aldoxycarb (863)+COMPOUND OF FORMULA I, AZ 60541 (compound code)+COMPOUND OF FORMULA I, benclothiaz [CCN]+COMPOUND OF FORMULA I, benomyl (62)+COMPOUND OF FORMULA I, butylpyridaben (alternative name)+COMPOUND OF FORMULA I, cadusafos (109)+COMPOUND OF FORMULA I, carbofuran (118)+COMPOUND OF FORMULA I, carbon disulfide (945)+COMPOUND OF FORMULA I, carbosulfan (119)+COMPOUND OF FORMULA I, chloropicrin (141)+COMPOUND OF FORMULA I, chlorpyrifos (145)+COMPOUND OF FORMULA I, cloethocarb (999)+COMPOUND OF FORMULA I, cytokinins (alternative name) (210)+COMPOUND OF FORMULA I, dazomet (216)+COMPOUND OF FORMULA I, DBCP (1045)+COMPOUND OF FORMULA I, DCIP (218)+COMPOUND OF FORMULA I, diamidafos (1044)+COMPOUND OF FORMULA I, dichlofenthion (1051)+COMPOUND OF FORMULA I, dicliphos (alternative name)+COMPOUND OF FORMULA I, dimethoate (262)+COMPOUND OF FORMULA I, doramectin (alternative name) [CCN]+COMPOUND OF FORMULA I, emamectin (291)+COMPOUND OF FORMULA I, emamectin benzoate (291)+COMPOUND OF FORMULA I, eprinomectin (alternative name) [CCN]+COMPOUND OF FORMULA I, ethoprophos (312)+COMPOUND OF FORMULA I, ethylene dibromide (316)+COMPOUND OF FORMULA I, fenamiphos (326)+COMPOUND OF FORMULA I, fenpyrad (alternative name)+COMPOUND OF FORMULA I, fensulfothion (1158)+COMPOUND OF FORMULA I, fluensulfone (CAS. Reg. No.: 318290-98-1)+COMPOUND OF FORMULA I, fosthiazate (408)+COMPOUND OF FORMULA I, fosthietan (1196)+COMPOUND OF FORMULA I, furfural (alternative name) [CCN]+COMPOUND OF FORMULA I, GY-81 (development code) (423)+COMPOUND OF FORMULA I, heterophos [CCN]+COMPOUND OF FORMULA I, imicyafos [CCN]+COMPOUND OF FORMULA I, iodomethane (IUPAC name) (542)+COMPOUND OF FORMULA I, isamidofos (1230)+COMPOUND OF FORMULA I, isazofos (1231)+COMPOUND OF FORMULA I, ivermectin (alternative name) [CCN]+COMPOUND OF FORMULA I, kinetin (alternative name) (210)+COMPOUND OF FORMULA I, mecarphon (1258)+COMPOUND OF FORMULA I, metam (519)+COMPOUND OF FORMULA I, metam-potassium (alternative name) (519)+COMPOUND OF FORMULA I, metam-sodium (519)+COMPOUND OF FORMULA I, methyl bromide (537)+COMPOUND OF FORMULA I, methyl isothiocyanate (543)+COMPOUND OF FORMULA I, milbemycin oxime (alternative name) [CCN]+COMPOUND OF FORMULA I, moxidectin (alternative name) [CCN]+COMPOUND OF FORMULA I, *Myrothecium verrucaria* composition (alternative name) (565)+COMPOUND OF FORMULA I, NC-184 (compound code)+COMPOUND OF FORMULA I, oxamyl (602)+COMPOUND OF FORMULA I, phorate (636)+COMPOUND OF FORMULA I, phosphamidon (639)+COMPOUND OF FORMULA I, phosphocarb [CCN]+COMPOUND OF FORMULA I, sebufos (alternative name)+COMPOUND OF FORMULA I, selamectin (alternative name) [CCN]+COMPOUND OF FORMULA I, spinosad (737)+COMPOUND OF FORMULA I, terbam (alternative name)+COMPOUND OF FORMULA I, terbufos (773)+COMPOUND OF FORMULA I, tetrachlorothiophene (IUPAC/Chemical Abstracts name) (1422)+COMPOUND OF FORMULA I, thiafenox (alternative name)+COMPOUND OF FORMULA I, thionazin (1434)+COMPOUND OF FORMULA I, triazophos (820)+COMPOUND OF FORMULA I, triazuron (alternative name)+COMPOUND OF FORMULA I, xylenols [CCN]+COMPOUND OF FORMULA I, yl-5302 (compound code) and zeatin (alternative name) (210)+COMPOUND OF FORMULA I, a nitrification inhibitor selected from the group of substances consisting of potassium ethylxanthate [CCN] and nitrapyrin (580)+COMPOUND OF FORMULA I, a plant activator selected from the group of substances consisting of acibenzolar (6)+COMPOUND OF FORMULA I, acibenzolar-S-methyl (6)+COMPOUND OF FORMULA I, probenazole (658) and *Reynoutria sachalinensis* extract (alternative name) (720)+COMPOUND OF FORMULA I, a rodenticide selected from the group of substances consisting of 2-isovalerylindan-1,3-dione (IUPAC name) (1246)+COMPOUND OF FORMULA I, 4-(quinoxalin-2-ylamino)benzenesulfonamide (IUPAC name) (748)+COMPOUND OF FORMULA I, alpha-chlorohydrin [CCN]+COMPOUND OF FORMULA I, aluminium phosphide (640)+COMPOUND OF FORMULA I, antu (880)+COMPOUND OF FORMULA I, arsenous oxide (882)+COMPOUND OF FORMULA I, barium carbonate (891)+COMPOUND OF FORMULA I, bisthiosemi (912)+COMPOUND OF FORMULA I, brodifacoum (89)+COMPOUND OF FORMULA I, bromadiolone (91)+COMPOUND OF FORMULA I, bromethalin (92)+COMPOUND OF FORMULA I, calcium cyanide (444)+COMPOUND OF FORMULA I, chloralose (127)+COMPOUND OF FORMULA I, chlorophacinone (140)+COMPOUND OF FORMULA I, cholecalciferol (alternative name) (850)+COMPOUND OF FORMULA I, coumachlor (1004)+COMPOUND OF FORMULA I, coumafuryl (1005)+COMPOUND OF FORMULA I, coumatetralyl (175)+COMPOUND OF FORMULA I, crimidine (1009)+COMPOUND OF FORMULA I, difenacoum (246)+COMPOUND OF FORMULA I, difethialone (249)+COMPOUND OF FORMULA I, diphacinone (273)+COMPOUND OF FORMULA I, ergocalciferol (301)+COMPOUND OF FORMULA I, flocoumafen (357)+COMPOUND OF FORMULA I, fluoroacetamide (379)+COMPOUND OF FORMULA I, flupropadine (1183)+COMPOUND OF FORMULA I, flupropadine hydrochloride (1183)+COMPOUND OF FORMULA I, gamma-HCH (430)+COMPOUND OF FORMULA I, HCH (430)+COMPOUND OF FORMULA I, hydrogen cyanide (444)+COMPOUND OF FORMULA I, iodomethane (IUPAC name) (542)+COMPOUND OF FORMULA I, lindane (430)+COMPOUND OF FORMULA I, magnesium phosphide (IUPAC name) (640)+COMPOUND OF FORMULA I, methyl bromide (537)+COMPOUND OF FORMULA I, norbormide (1318)+COMPOUND OF FORMULA I, phosacetim (1336)+COMPOUND OF FORMULA I, phosphine (IUPAC name) (640)+COMPOUND OF FORMULA I, phosphorus [CCN]+COMPOUND OF FORMULA I, pindone (1341)+COMPOUND OF FORMULA I, potassium arsenite [CCN]+COMPOUND OF FORMULA I, pyrinuron (1371)+COMPOUND OF FORMULA I, scilliroside (1390)+COMPOUND OF FORMULA I, sodium arsenite [CCN]+COMPOUND OF FORMULA I, sodium cyanide (444)+COMPOUND OF FORMULA I, sodium fluoroacetate (735)+COMPOUND OF FORMULA I, strychnine (745)+COMPOUND OF FORMULA I, thallium sulfate [CCN]+COMPOUND OF FORMULA I, warfarin (851) and zinc phosphide (640)+COMPOUND OF FORMULA I, a synergist selected from the group of substances consisting of 2-(2-butoxyethoxy)-ethyl piperonylate (IUPAC name) (934)+COMPOUND OF FORMULA I, 5-(1,3-benzodioxol-5-yl)-3-hexylcyclohex-2-enone (IUPAC name) (903)+COMPOUND OF FORMULA I, farnesol with nerolidol (alternative name) (324)+COMPOUND OF FORMULA I, MB-599 (development code) (498)+COMPOUND OF FORMULA I, MGK 264 (development code) (296)+COMPOUND OF FORMULA I, piperonyl butoxide (649)+COMPOUND OF FORMULA I, piprotal (1343)+COMPOUND OF FORMULA I, propyl isomer (1358)+COMPOUND OF FORMULA I, S421 (development code) (724)+COMPOUND OF FORMULA I, sesamex (1393)+COMPOUND OF FORMULA I, sesasmolin (1394) and sulfoxide (1406)+COMPOUND OF FORMULA I, an animal repellent selected from the group of substances consisting of anthraquinone (32)+COMPOUND OF FORMULA I, chloralose (127)+COMPOUND OF FORMULA I, copper naphthenate [CCN]+COMPOUND OF FORMULA I, copper oxychloride (171)+COMPOUND OF FORMULA I, diazinon (227)+COMPOUND OF FORMULA I, dicyclopentadiene (chemical name) (1069)+COMPOUND OF FORMULA I, guazatine (422)+COMPOUND OF FORMULA I, guazatine acetates (422)+COMPOUND OF FORMULA I, methiocarb (530)+COMPOUND OF FORMULA I, pyridin-4-amine (IUPAC name) (23)+COMPOUND OF FORMULA I, thiram (804)+COMPOUND OF FORMULA I, trimethacarb (840)+COMPOUND OF FORMULA I, zinc naphthenate [CCN] and ziram (856)+COMPOUND OF FORMULA I, a virucide selected from the group of substances consisting of imanin (alternative name) [CCN] and ribavirin (alternative name) [CCN]+COMPOUND OF FORMULA I, a wound protectant selected from the group of substances consisting of mercuric oxide (512)+COMPOUND OF FORMULA I, octhilinone (590) and thiophanate-methyl (802)+COMPOUND OF FORMULA I, an insecticide selected from the group consisting of the compound of the formula A-1

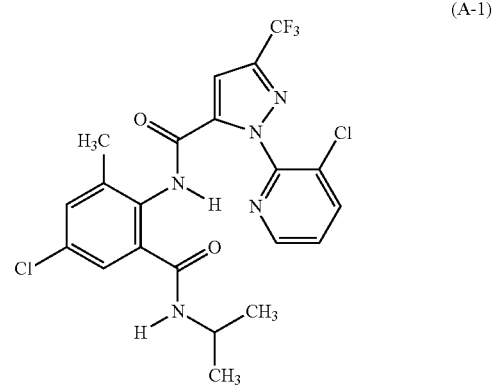 [SMILES: Cc1cc(Cl)cc(C(=O)NC(C)C)c1NC(=O)c1cc(C(F)(F)F)nn1-c1ncccc1Cl]

(A-1)

+COMPOUND OF FORMULA I, the formula A-2

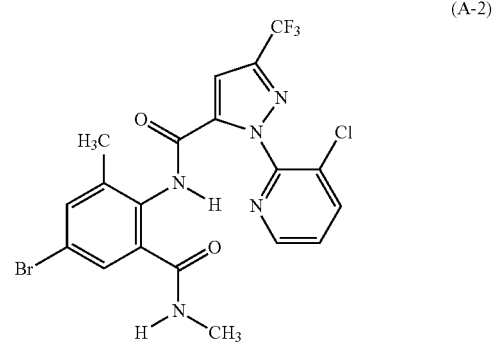 [SMILES: CNC(=O)c1cc(Br)cc(C)c1NC(=O)c1cc(C(F)(F)F)nn1-c1ncccc1Cl]

(A-2)

| 71 | 72 |
+COMPOUND OF FORMULA I, the formula A-3 (A-3)
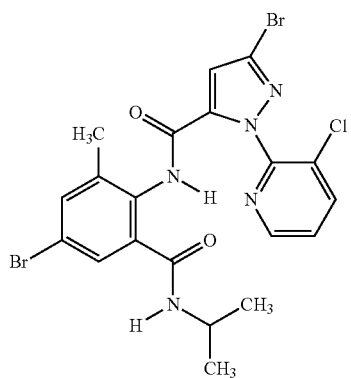
+COMPOUND OF FORMULA I, the formula A-7 (A-7)
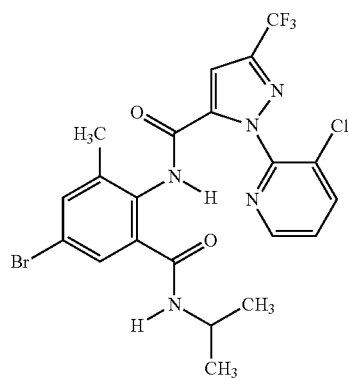
+COMPOUND OF FORMULA I, the formula A-4 (A-4)
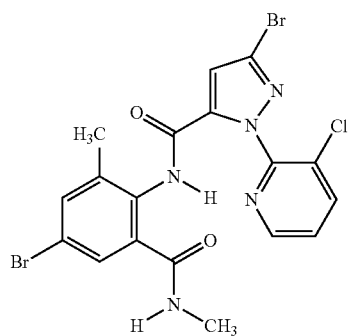
+COMPOUND OF FORMULA I, the formula A-8 (A-8)
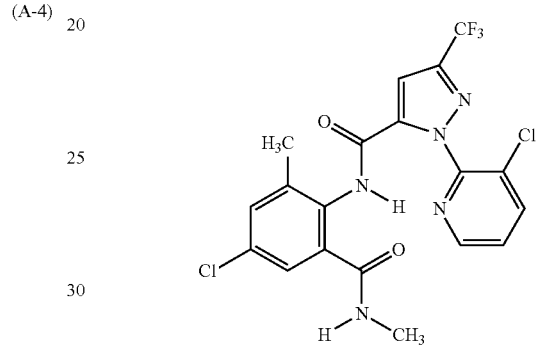
+COMPOUND OF FORMULA I, the formula A-5 (A-5)
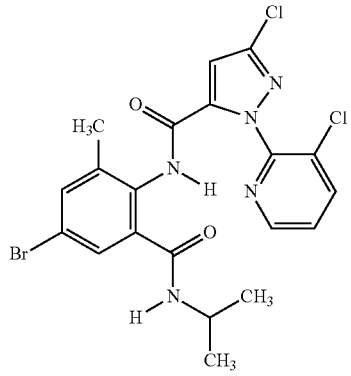
+COMPOUND OF FORMULA I, the formula A-9 (A-9)
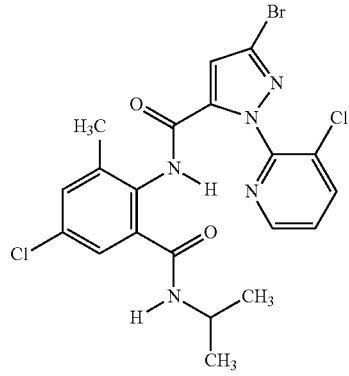
+COMPOUND OF FORMULA I, the formula A-6 (A-6)
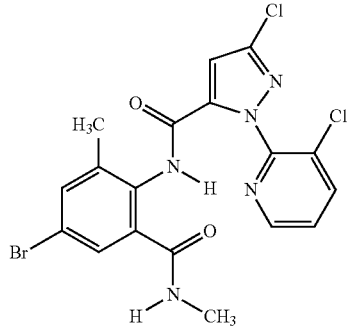
+COMPOUND OF FORMULA I, the formula A-10 (A-10)
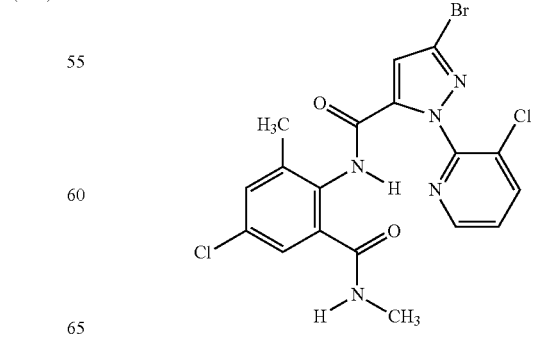

73
+COMPOUND OF FORMULA I, the formula A-11 (A-11)
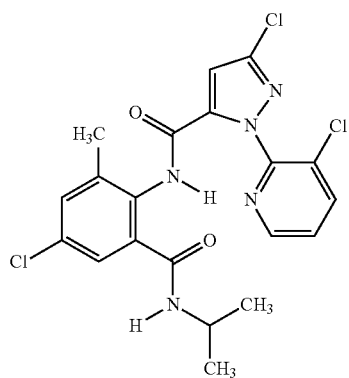
+COMPOUND OF FORMULA I, the formula A-12 (A-12)
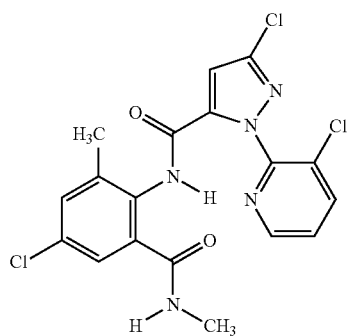
+COMPOUND OF FORMULA I, the formula A-13 (A-13)
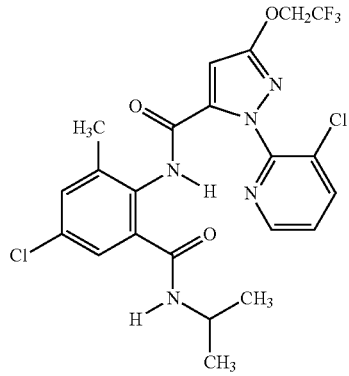
+COMPOUND OF FORMULA I, the formula A-14 (A-14)
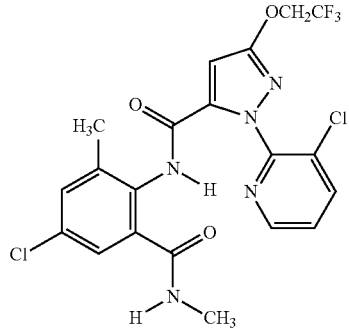
74
+COMPOUND OF FORMULA I, the formula A-15 (A-15)
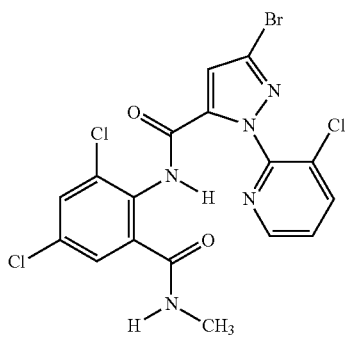
+COMPOUND OF FORMULA I, the formula A-16 (A-16)
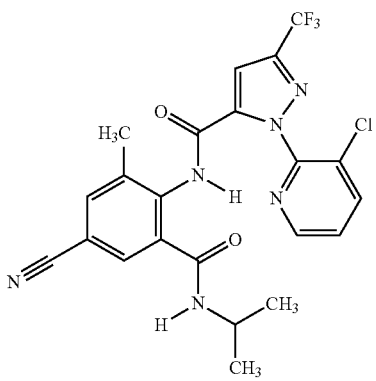
+COMPOUND OF FORMULA I, the formula A-17 (A-17)
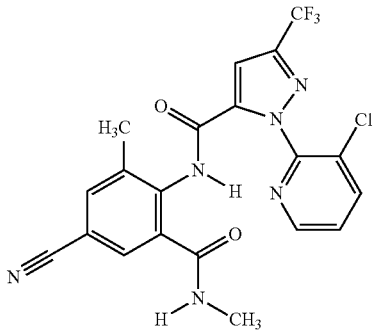
+COMPOUND OF FORMULA I, the formula A-18 (A-18)
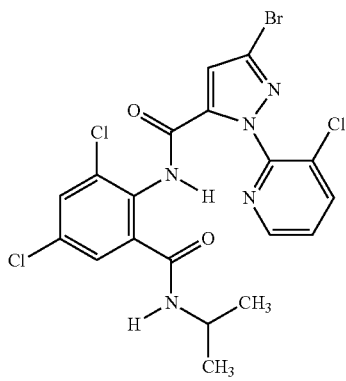

+COMPOUND OF FORMULA I, the formula A-19
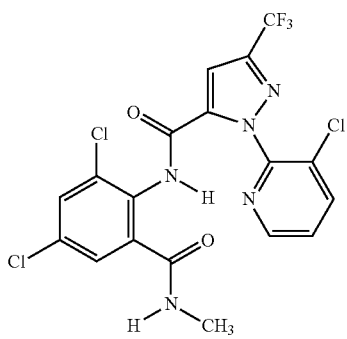
(A-19)
+COMPOUND OF FORMULA I, the formula A-20
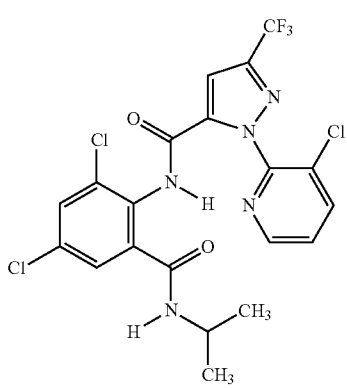
(A-20)
+COMPOUND OF FORMULA I, the formula A-21
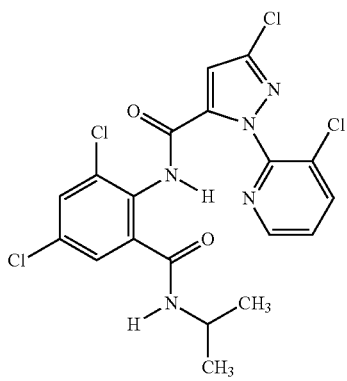
(A-21)
+COMPOUND OF FORMULA I, the formula A-22
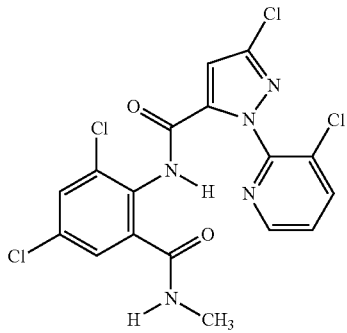
(A-22)
+COMPOUND OF FORMULA I, the formula A-23
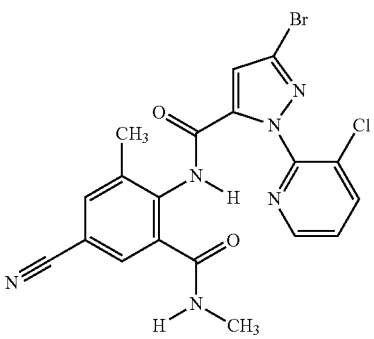
(A-23)
+COMPOUND OF FORMULA I, the formula A-24
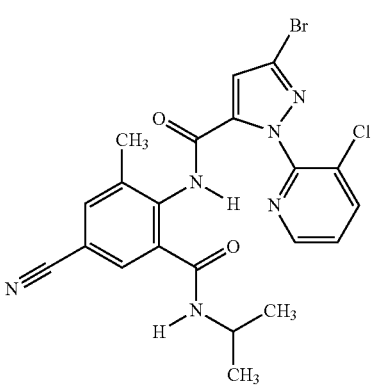
(A-24)
+COMPOUND OF FORMULA I, the formula A-25
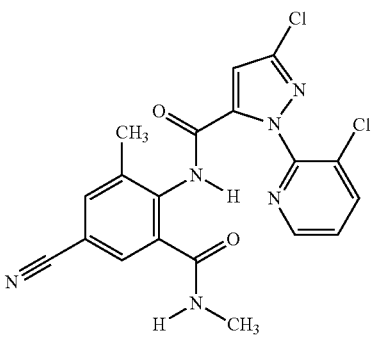
(A-25)
+COMPOUND OF FORMULA I, the formula A-26
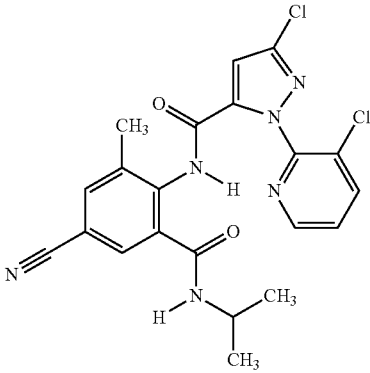
(A-26)

+COMPOUND OF FORMULA I, and the formula A-27

(A-27)

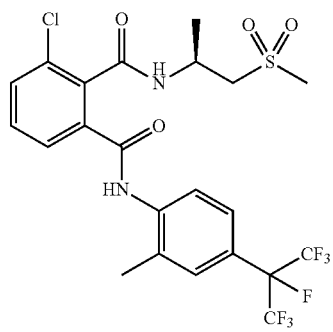

+COMPOUND OF FORMULA I.

The references in brackets behind the active ingredients, e.g. [3878-19-1] refer to the Chemical Abstracts Registry number. The compounds of the formula A-1 to A-26 are described in WO 03/015518 or in WO 04/067528. The compound of the formula A-27 is described in WO 06/022225 and in WO 07/112,844. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright © 1995-2004]; for example, the compound "acetoprole" is described under the internet address http://www.alanwood.net/pesticides/acetoprole.htmL.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The compounds of formula I according to the invention can also be used in combination with one or more fungicides. In particular, in the following mixtures of the compounds of formula I with fungicides, the term COMPOUND OF FORMULA I preferably refers to a compound selected from one of the Tables 1 to 28:
COMPOUND OF FORMULA I+(E)-N-methyl-2-[2-(2,5-dimethylphenoxymethyl)phenyl]-2-methoxy-iminoacetamide (SSF-129), COMPOUND OF FORMULA I+4-bromo-2-cyano-N,N-dimethyl-6-trifluoromethylbenzimidazole-1-sulphonamide, COMPOUND OF FORMULA I+α-[N-(3-chloro-2,6-xylyl)-2-methoxyacetamido]-7-butyrolactone, COMPOUND OF FORMULA I+4-chloro-2-cyano-N,N-dimethyl-5-p-tolylimidazole-1-sulfonamide (IKF-916, cyamidazosulfamid), COMPOUND OF FORMULA I+3-5-dichloro-N-(3-chloro-1-ethyl-1-methyl-2-oxopropyl)-4-methylbenzamide (RH-7281, zoxamide), COMPOUND OF FORMULA I+N-allyl-4,5-dimethyl-2-trimethylsilylthiophene-3-carboxamide (MON65500), COMPOUND OF FORMULA I+N-(1-cyano-1,2-dimethylpropyl)-2-(2,4-dichlorophenoxy)propionamide (AC382042), COMPOUND OF FORMULA I+N-(2-methoxy-5-pyridyl)-cyclopropane carboxamide, COMPOUND OF FORMULA I+acibenzolar, COMPOUND OF FORMULA I+alanycarb, COMPOUND OF FORMULA I+aldimorph, COMPOUND OF FORMULA I+amisulbrom, COMPOUND OF FORMULA I+anilazine, COMPOUND OF FORMULA I+azaconazole, COMPOUND OF FORMULA I+azoxystrobin, COMPOUND OF FORMULA I+benalaxyl, COMPOUND OF FORMULA I+benalaxyl-M, COMPOUND OF FORMULA I+benomyl, COMPOUND OF FORMULA I+benthiavalicarb, COMPOUND OF FORMULA I+biloxazol, COMPOUND OF FORMULA I+bitertanol, COMPOUND OF FORMULA I+bixafen, COMPOUND OF FORMULA I+blasticidin S, COMPOUND OF FORMULA I+boscalid, COMPOUND OF FORMULA I+bromuconazole, COMPOUND OF FORMULA I+bupirimate, COMPOUND OF FORMULA I+captafol, COMPOUND OF FORMULA I+captan, COMPOUND OF FORMULA I+carbendazim, COMPOUND OF FORMULA I+carbendazim chlorhydrate, COMPOUND OF FORMULA I+carboxin, COMPOUND OF FORMULA I+carpropamid, carvone, COMPOUND OF FORMULA I+CGA41396, COMPOUND OF FORMULA I+CGA41397, COMPOUND OF FORMULA I+chinomethionate, COMPOUND OF FORMULA I+chlazafenone, COMPOUND OF FORMULA I+chlorothalonil, COMPOUND OF FORMULA I+chlorozolinate, COMPOUND OF FORMULA I+clozylacon, COMPOUND OF FORMULA I+copper containing compounds such as copper oxychloride, copper oxyquinolate, copper sulphate, copper tallate and Bordeaux mixture, COMPOUND OF FORMULA I+cyazofamid, COMPOUND OF FORMULA I+cyflufenamid, COMPOUND OF FORMULA I+cymoxanil, COMPOUND OF FORMULA I+cyproconazole, COMPOUND OF FORMULA I+cyprodinil, COMPOUND OF FORMULA I+debacarb, COMPOUND OF FORMULA I+di-2-pyridyl disulphide 1,1'-dioxide, COMPOUND OF FORMULA I+dichlofluanid, COMPOUND OF FORMULA I+diclomezine, COMPOUND OF FORMULA I+dicloran, COMPOUND OF FORMULA I+diethofencarb, COMPOUND OF FORMULA I+difenoconazole, COMPOUND OF FORMULA I+difenzoquat, COMPOUND OF FORMULA I+diflumetorim, COMPOUND OF FORMULA I+O, O-di-iso-propyl-S-benzyl thiophosphate, COMPOUND OF FORMULA I+dimefluazole, COMPOUND OF FORMULA I+dimetconazole, COMPOUND OF FORMULA I+dimethomorph, COMPOUND OF FORMULA I+dimethirimol, COMPOUND OF FORMULA I+dimoxystrobin, COMPOUND OF FORMULA I+diniconazole, COMPOUND OF FORMULA I+dinocap, COMPOUND OF FORMULA I+dithianon, COMPOUND OF FORMULA I+dodecyl dimethyl ammonium chloride, COMPOUND OF FORMULA I+dodemorph, COMPOUND OF FORMULA I+dodine, COMPOUND OF FORMULA I+doguadine, COMPOUND OF FORMULA I+edifenphos, COMPOUND OF FORMULA I+epoxiconazole, COMPOUND OF FORMULA I+ethirimol, COMPOUND OF FORMULA I+ethyl(Z)—N-benzyl-N([methyl(methyl-thioethylideneaminooxycarbonyl)amino]thio)-β-alaninate, COMPOUND OF FORMULA I+etridiazole, COMPOUND OF FORMULA I+famoxadone, COMPOUND OF FORMULA I+fenamidone (RPA407213), COMPOUND OF FORMULA I+fenarimol, COMPOUND OF FORMULA I+fenbuconazole, COMPOUND OF FOR- MULA I+fenfuram, COMPOUND OF FORMULA I+fenhexamid (KBR2738), COMPOUND OF FORMULA I+fenoxanil, COMPOUND OF FORMULA I+fenpiclonil, COMPOUND OF FORMULA I+fenpropidin, COMPOUND OF FORMULA I+fenpropimorph, COMPOUND OF FORMULA I+fenpyrazamine/ipfenpyrazolone, COMPOUND OF FORMULA I+fentin acetate, COMPOUND OF FORMULA I+fentin hydroxide, COMPOUND OF FORMULA I+ferbam, COMPOUND OF FORMULA I+ferimzone, COMPOUND OF FORMULA I+fluazinam, COMPOUND OF FORMULA I+fludioxonil, COMPOUND OF FORMULA I+flumetover, COMPOUND OF FORMULA I+flumorph, COMPOUND OF FORMULA I+fluopicolide, COMPOUND OF FORMULA I+fluopyram, COMPOUND OF FORMULA I+fluoxastrobin, COMPOUND OF FORMULA I+fluoroimide, COMPOUND OF FORMULA I+fluquinconazole, COMPOUND OF FORMULA I+flusilazole, COMPOUND OF FORMULA I+flutianil, COMPOUND OF FORMULA I+flutolanil, COMPOUND OF FORMULA I+flutriafol, COMPOUND OF FORMULA I+fluxapyroxad, COMPOUND OF FORMULA I+folpet, COMPOUND OF FORMULA I+fuberidazole, COMPOUND OF FORMULA I+furalaxyl, COMPOUND OF FORMULA I+furametpyr, COMPOUND OF FORMULA I+guazatine, COMPOUND OF FORMULA I+hexaconazole, COMPOUND OF FORMULA I+hydroxyisoxazole, COMPOUND OF FORMULA I+hymexazole, COMPOUND OF FORMULA I+imazalil, COMPOUND OF FORMULA I+imibenconazole, COMPOUND OF FORMULA I+iminoctadine, COMPOUND OF FORMULA I+iminoctadine triacetate, COMPOUND OF FORMULA I+ipconazole, COMPOUND OF FORMULA I+iprobenfos, COMPOUND OF FORMULA I+iprodione, COMPOUND OF FORMULA I+iprovalicarb (SZX0722), COMPOUND OF FORMULA I+isopropanyl butyl carbamate, COMPOUND OF FORMULA I+isoprothiolane, COMPOUND OF FORMULA I+isopyrazam, COMPOUND OF FORMULA I+isotianil, COMPOUND OF FORMULA I+kasugamycin, COMPOUND OF FORMULA I+kresoximmethyl, COMPOUND OF FORMULA I+LY186054, COMPOUND OF FORMULA I+LY211795, COMPOUND OF FORMULA I+LY248908, COMPOUND OF FORMULA I+mancozeb, COMPOUND OF FORMULA I+mandipropamid, COMPOUND OF FORMULA I+maneb, COMPOUND OF FORMULA I+mefenoxam, COMPOUND OF FORMULA I+mepanipyrim, COMPOUND OF FORMULA I+mepronil, COMPOUND OF FORMULA I+meptyldinocap, COMPOUND OF FORMULA I+metalaxyl, COMPOUND OF FORMULA I+metconazole, COMPOUND OF FORMULA I+metiram, COMPOUND OF FORMULA I+metiram-zinc, COMPOUND OF FORMULA I+metominostrobin, COMPOUND OF FORMULA I+metrafenone, COMPOUND OF FORMULA I+myclobutanil, COMPOUND OF FORMULA I+neoasozin, COMPOUND OF FORMULA I+nickel dimethyldithiocarbamate, COMPOUND OF FORMULA I+nicobifen, COMPOUND OF FORMULA I+nitrothal-isopropyl, COMPOUND OF FORMULA I+nuarimol, COMPOUND OF FORMULA I+ofurace, COMPOUND OF FORMULA I+organomercury compounds, COMPOUND OF FORMULA I+orysastrobin, COMPOUND OF FORMULA I+oxadixyl, COMPOUND OF FORMULA I+oxasulfuron, COMPOUND OF FORMULA I+oxolinic acid, COMPOUND OF FORMULA I+oxpoconazole, COMPOUND OF FORMULA I+oxycarboxin, COMPOUND OF FORMULA I+pefurazoate, COMPOUND OF FORMULA I+penconazole, COMPOUND OF FORMULA I+pencycuron, COMPOUND OF FORMULA I+penthiopyrad, COMPOUND OF FORMULA I+phenazin oxide, COMPOUND OF FORMULA I+phosetyl-Al, COMPOUND OF FORMULA I+phosphorus acids, COMPOUND OF FORMULA I+phthalide, COMPOUND OF FORMULA I+picoxystrobin (ZA1963), COMPOUND OF FORMULA I+polyoxin D, COMPOUND OF FORMULA I+polyram, COMPOUND OF FORMULA I+probenazole, COMPOUND OF FORMULA I+prochloraz, COMPOUND OF FORMULA I+procymidone, COMPOUND OF FORMULA I+propamocarb, COMPOUND OF FORMULA I+propiconazole, COMPOUND OF FORMULA I+propineb, COMPOUND OF FORMULA I+propionic acid, COMPOUND OF FORMULA I+proquinazid, COMPOUND OF FORMULA I+prothioconazole, COMPOUND OF FORMULA I+pyraclostrobin, COMPOUND OF FORMULA I+pyrazophos, COMPOUND OF FORMULA I+pyribencarb, COMPOUND OF FORMULA I+pyrifenox, COMPOUND OF FORMULA I+pyrimethanil, COMPOUND OF FORMULA I+pyroquilon, COMPOUND OF FORMULA I+pyroxyfur, COMPOUND OF FORMULA I+pyrrolnitrin, COMPOUND OF FORMULA I+quaternary ammonium compounds, COMPOUND OF FORMULA I+quinomethionate, COMPOUND OF FORMULA I+quinoxyfen, COMPOUND OF FORMULA I+quintozene, COMPOUND OF FORMULA I+sedaxane, COMPOUND OF FORMULA I+sipconazole (F-155), COMPOUND OF FORMULA I+sodium pentachlorophenate, COMPOUND OF FORMULA I+spiroxamine, COMPOUND OF FORMULA I+streptomycin, COMPOUND OF FORMULA I+sulphur, COMPOUND OF FORMULA I+tebuconazole, COMPOUND OF FORMULA I+tecloftalam, COMPOUND OF FORMULA I+tecnazene, COMPOUND OF FORMULA I+tetraconazole, COMPOUND OF FORMULA I+thiabendazole, COMPOUND OF FORMULA I+thifluzamid, COMPOUND OF FORMULA I+2-(thiocyanomethylthio)benzothiazole, COMPOUND OF FORMULA I+thiophanate-methyl, COMPOUND OF FORMULA I+thiram, COMPOUND OF FORMULA I+tiadinil, COMPOUND OF FORMULA I+timibenconazole, COMPOUND OF FORMULA I+tolclofos-methyl, COMPOUND OF FORMULA I+tolylfluanid, COMPOUND OF FORMULA I+triadimefon, COMPOUND OF FORMULA I+triadimenol, COMPOUND OF FORMULA I+triazbutil, COMPOUND OF FORMULA I+triazoxide, COMPOUND OF FORMULA I+tricyclazole, COMPOUND OF FORMULA I+tridemorph, COMPOUND OF FORMULA I+trifloxystrobin, COMPOUND OF FORMULA I+triforine, COMPOUND OF FORMULA I+triflumizole, COMPOUND OF FORMULA I+triticonazole, COMPOUND OF FORMULA I+validamycin A, COMPOUND OF FORMULA I+valiphenal, COMPOUND OF FORMULA I+vapam, COMPOUND OF FORMULA I+vinclozolin, COMPOUND OF FORMULA I+zineb and COMPOUND OF FORMULA I+ziram.

The compounds of formula I may be mixed with soil, peat or other rooting media for the protection of plants against seed-borne, soil-borne or foliar fungal diseases.

The compounds of formula I according to the invention can also be used in combination with one or more other synergists. In particular, the following mixtures of the COMPOUND OF FORMULA I, where this term preferably refers to a compound selected from one of the Tables 1 to 28, are important:
COMPOUND OF FORMULA I+piperonyl butoxide, COMPOUND OF FORMULA I+sesamex, COMPOUND OF FORMULA I+safroxan and COMPOUND OF FORMULA I+dodecyl imidazole.

The compounds of formula I according to the invention can also be used in combination with one or more other herbicides. In particular, the following mixtures of the COMPOUND OF FORMULA I, where this term preferably refers to a compound selected from one of the Tables 1 to 28, are important:
COMPOUND OF FORMULA I+acetochlor, COMPOUND OF FORMULA I+acifluorfen, COMPOUND OF FORMULA I+acifluorfen-sodium, COMPOUND OF FORMULA I+aclonifen, COMPOUND OF FORMULA I+acrolein, COMPOUND OF FORMULA I+alachlor, COMPOUND OF FORMULA I+alloxydim, COMPOUND OF FORMULA I+allyl alcohol, COMPOUND OF FORMULA I+ametryn, COMPOUND OF FORMULA I+amicarbazone, COMPOUND OF FORMULA I+amidosulfuron, COMPOUND OF FORMULA I+aminocyclopyrachlor, COMPOUND OF FORMULA I+aminopyralid, COMPOUND OF FORMULA I+amitrole, COMPOUND OF FORMULA I+ammonium sulfamate, COMPOUND OF FORMULA I+anilofos, COMPOUND OF FORMULA I+asulam, COMPOUND OF FORMULA I+atraton, COMPOUND OF FORMULA I+atrazine, COMPOUND OF FORMULA I+azimsulfuron, COMPOUND OF FORMULA I+BCPC, COMPOUND OF FORMULA I+beflubutamid, COMPOUND OF FORMULA I+benazolin, COMPOUND OF FORMULA I+bencarbazone, COMPOUND OF FORMULA I+benfluralin, COMPOUND OF FORMULA I+benfuresate, COMPOUND OF FORMULA I+bensulfuron, COMPOUND OF FORMULA I+bensulfuron-methyl, COMPOUND OF FORMULA I+bensulide, COMPOUND OF FORMULA I+bentazone, COMPOUND OF FORMULA I+benzfendizone, COMPOUND OF FORMULA I+benzobicyclon, COMPOUND OF FORMULA I+benzofenap, COMPOUND OF THE FORMULA I+bicyclopyrone, COMPOUND OF FORMULA I+bifenox, COMPOUND OF FORMULA I+bilanafos, COMPOUND OF FORMULA I+bispyribac, COMPOUND OF FORMULA I+bispyribac-sodium, COMPOUND OF FORMULA I+borax, COMPOUND OF FORMULA I+bromacil, COMPOUND OF FORMULA I+bromobutide, COMPOUND OF FORMULA I+bromoxynil, COMPOUND OF FORMULA I+butachlor, COMPOUND OF FORMULA I+butafenacil, COMPOUND OF FORMULA I+butamifos, COMPOUND OF FORMULA I+butralin, COMPOUND OF FORMULA I+butroxydim, COMPOUND OF FORMULA I+butylate, COMPOUND OF FORMULA I+cacodylic acid, COMPOUND OF FORMULA I+calcium chlorate, COMPOUND OF FORMULA I+cafenstrole, COMPOUND OF FORMULA I+carbetamide, COMPOUND OF FORMULA I+carfentrazone, COMPOUND OF FORMULA I+carfentrazone-ethyl, COMPOUND OF FORMULA I+CDEA, COMPOUND OF FORMULA I+CEPC, COMPOUND OF FORMULA I+chloroflurenol, COMPOUND OF FORMULA I+chloroflurenol-methyl, COMPOUND OF FORMULA I+chloridazon, COMPOUND OF FORMULA I+chlorimuron, COMPOUND OF FORMULA I+chlorimuron-ethyl, COMPOUND OF FORMULA I+chloroacetic acid, COMPOUND OF FORMULA I+chlorotoluron, COMPOUND OF FORMULA I+chlorpropham, COMPOUND OF FORMULA I+chlorsulfuron, COMPOUND OF FORMULA I+chlorothal, COMPOUND OF FORMULA I+chlorothal-dimethyl, COMPOUND OF FORMULA I+cinidon-ethyl, COMPOUND OF FORMULA I+cinmethylin, COMPOUND OF FORMULA I+cinosulfuron, COMPOUND OF FORMULA I+cisanilide, COMPOUND OF FORMULA I+clethodim, COMPOUND OF FORMULA I+clodinafop, COMPOUND OF FORMULA I+clodinafop-propargyl, COMPOUND OF FORMULA I+clomazone, COMPOUND OF FORMULA I+clomeprop, COMPOUND OF FORMULA I+clopyralid, COMPOUND OF FORMULA I+cloransulam, COMPOUND OF FORMULA I+cloransulam-methyl, COMPOUND OF FORMULA I+CMA, COMPOUND OF FORMULA I+4-CPB, COMPOUND OF FORMULA I+CPMF, COMPOUND OF FORMULA I+4-CPP, COMPOUND OF FORMULA I+CPPC, COMPOUND OF FORMULA I+cresol, COMPOUND OF FORMULA I+cumyluron, COMPOUND OF FORMULA I+cyanamide, COMPOUND OF FORMULA I+cyanazine, COMPOUND OF FORMULA I+cycloate, COMPOUND OF FORMULA I+cyclosulfamuron, COMPOUND OF FORMULA I+cycloxydim, COMPOUND OF FORMULA I+cyhalofop, COMPOUND OF FORMULA I+cyhalofop-butyl, COMPOUND OF FORMULA I+2,4-D, COMPOUND OF FORMULA I+3,4-DA, COMPOUND OF FORMULA I+daimuron, COMPOUND OF FORMULA I+dalapon, COMPOUND OF FORMULA I+dazomet, COMPOUND OF FORMULA I+2,4-DB, COMPOUND OF FORMULA I+3,4-DB, COMPOUND OF FORMULA I+2,4-DEB, COMPOUND OF FORMULA I+desmedipham, COMPOUND OF FORMULA I+dicamba, COMPOUND OF FORMULA I+dichlobenil, COMPOUND OF FORMULA I+ortho-dichlorobenzene, COMPOUND OF FORMULA I+para-dichlorobenzene, COMPOUND OF FORMULA I+dichlorprop, COMPOUND OF FORMULA I+dichlorprop-P, COMPOUND OF FORMULA I+diclofop, COMPOUND OF FORMULA I+diclofop-methyl, COMPOUND OF FORMULA I+diclosulam, COMPOUND OF FORMULA I+difenzoquat, COMPOUND OF FORMULA I+difenzoquat metilsulfate, COMPOUND OF FORMULA I+diflufenican, COMPOUND OF FORMULA I+diflufenzopyr, COMPOUND OF FORMULA I+dimefuron, COMPOUND OF FORMULA I+dimepiperate, COMPOUND OF FORMULA I+dimethachlor, COMPOUND OF FORMULA I+dimethametryn, COMPOUND OF FORMULA I+dimethenamid, COMPOUND OF FORMULA I+dimethenamid-P, COMPOUND OF FORMULA I+dimethipin, COMPOUND OF FORMULA I+dimethylarsinic acid, COMPOUND OF FORMULA I+dinitramine, COMPOUND OF FORMULA I+dinoterb, COMPOUND OF FORMULA I+diphenamid, COMPOUND OF FORMULA I+diquat, COMPOUND OF FORMULA I+diquat dibromide, COMPOUND OF FORMULA I+dithiopyr, COMPOUND OF FORMULA I+diuron, COMPOUND OF FORMULA I+DNOC, COMPOUND OF FORMULA I+3,4-DP, COMPOUND OF FORMULA I+DSMA, COMPOUND OF FORMULA I+EBEP, COMPOUND OF FORMULA I+endothal, COMPOUND OF FORMULA I+EPTC, COMPOUND OF FORMULA I+esprocarb, COMPOUND OF FORMULA I+ethalfluralin, COMPOUND OF FORMULA I+ethametsulfuron, COMPOUND OF FORMULA I+ethametsulfuron-methyl, COMPOUND OF FORMULA I+ethofumesate, COMPOUND OF FORMULA I+ethoxyfen, COMPOUND OF FORMULA I+ethoxysulfuron, COMPOUND OF FORMULA I+etobenzanid, COMPOUND OF FORMULA I+fenoxaprop-P, COMPOUND OF FORMULA I+fenoxaprop-P-ethyl, COMPOUND OF FORMULA I+fentrazamide, COMPOUND OF FORMULA I+ferrous sulfate, COMPOUND OF FORMULA I+flamprop-M, COMPOUND OF FORMULA I+flazasulfuron, COMPOUND OF FORMULA I+florasulam, COMPOUND OF FORMULA I+fluazifop, COMPOUND OF FORMULA I+fluazifop-butyl, COMPOUND OF FORMULA I+fluazifop-P, COMPOUND OF FORMULA I+fluazifop-P-butyl, COMPOUND OF FORMULA I+flucarbazone, COMPOUND OF FORMULA I+flucarbazone-sodium, COMPOUND OF FORMULA I+flucetosulfuron, COMPOUND OF FORMULA I+fluchloralin, COMPOUND OF FORMULA I+flufenacet, COMPOUND OF FORMULA I+flufenpyr, COMPOUND OF FORMULA I+flufenpyr-ethyl, COMPOUND OF FORMULA I+flumetsulam, COMPOUND OF FORMULA I+flumiclorac, COMPOUND OF FORMULA I+flumiclorac-pentyl, COMPOUND OF FORMULA I+flumioxazin, COMPOUND OF FORMULA I+fluometuron, COMPOUND OF FORMULA I+fluoroglycofen, COMPOUND OF FORMULA I+fluoroglycofen-ethyl, COMPOUND OF FORMULA I+flupropanate, COMPOUND OF FORMULA I+flupyrsulfuron, COMPOUND OF FORMULA I+flupyrsulfuron-methyl-sodium, COMPOUND OF FORMULA I+flurenol, COMPOUND OF FORMULA I+fluridone, COMPOUND OF FORMULA I+fluorochloridone, COMPOUND OF FORMULA I+fluoroxypyr, COMPOUND OF FORMULA I+flurtamone, COMPOUND OF FORMULA I+fluthiacet, COMPOUND OF FORMULA I+fluthiacet-methyl, COMPOUND OF FORMULA I+fomesafen, COMPOUND OF FORMULA I+foramsulfuron, COMPOUND OF FORMULA I+fosamine, COMPOUND OF FORMULA I+glufosinate, COMPOUND OF FORMULA I+glufosinate-ammonium, COMPOUND OF FORMULA I+glufosinate-P, COMPOUND OF FORMULA I+glyphosate, COMPOUND OF FORMULA I+glyphosate-trimesium, COMPOUND OF FORMULA I+halosulfuron, COMPOUND OF FORMULA I+halosulfuron-methyl, COMPOUND OF FORMULA I+haloxyfop, COMPOUND OF FORMULA I+haloxyfop-P, COMPOUND OF FORMULA I+HC-252, COMPOUND OF FORMULA I+hexazinone, COMPOUND OF FORMULA I+imazamethabenz, COMPOUND OF FORMULA I+imazamethabenz-methyl, COMPOUND OF FORMULA I+imazamox, COMPOUND OF FORMULA I+imazapic, COMPOUND OF FORMULA I+imazapyr, COMPOUND OF FORMULA I+imazaquin, COMPOUND OF FORMULA I+imazethapyr, COMPOUND OF FORMULA I+imazosulfuron, COMPOUND OF FORMULA I+indanofan, COMPOUND OF FORMULA I+indaziflam, COMPOUND OF FORMULA I+iodomethane, COMPOUND OF FORMULA I+iodosulfuron, COMPOUND OF FORMULA I+iodosulfuron-methyl-sodium, COMPOUND OF FORMULA I+ioxynil, COMPOUND OF FORMULA I+ipfencarbazone, COMPOUND OF FORMULA I+isoproturon, COMPOUND OF FORMULA I+isouron, COMPOUND OF FORMULA I+isoxaben, COMPOUND OF FORMULA I+isoxachlortole, COMPOUND OF FORMULA I+isoxaflutole, COMPOUND OF FORMULA I+karbutilate, COMPOUND OF FORMULA I+lactofen, COMPOUND OF FORMULA I+lenacil, COMPOUND OF FORMULA I+linuron, COMPOUND OF FORMULA I+MM, COMPOUND OF FORMULA I+MAMA, COMPOUND OF FORMULA I+MCPA, COMPOUND OF FORMULA I+MCPA-thioethyl, COMPOUND OF FORMULA I+MCPB, COMPOUND OF FORMULA I+mecoprop, COMPOUND OF FORMULA I+mecoprop-P, COMPOUND OF FORMULA I+mefenacet, COMPOUND OF FORMULA I+mefluidide, COMPOUND OF FORMULA I+mesosulfuron, COMPOUND OF FORMULA I+mesosulfuron-methyl, COMPOUND OF FORMULA I+mesotrione, COMPOUND OF FORMULA I+metam, COMPOUND OF FORMULA I+metamifop, COMPOUND OF FORMULA I+metamitron, COMPOUND OF FORMULA I+metazachlor, COMPOUND OF FORMULA I+methabenzthiazuron, COMPOUND OF FORMULA I+methylarsonic acid, COMPOUND OF FORMULA I+methyldymron, COMPOUND OF FORMULA I+methyl isothiocyanate, COMPOUND OF FORMULA I+metobenzuron, COMPOUND OF FORMULA I+metolachlor, COMPOUND OF FORMULA I+S-metolachlor, COMPOUND OF FORMULA I+metosulam, COMPOUND OF FORMULA I+metoxuron, COMPOUND OF FORMULA I+metribuzin, COMPOUND OF FORMULA I+metsulfuron, COMPOUND OF FORMULA I+metsulfuron-methyl, COMPOUND OF FORMULA I+MK-616, COMPOUND OF FORMULA I+molinate, COMPOUND OF FORMULA I+monolinuron, COMPOUND OF FORMULA I+MSMA, COMPOUND OF FORMULA I+naproanilide, COMPOUND OF FORMULA I+napropamide, COMPOUND OF FORMULA I+naptalam, COMPOUND OF FORMULA I+neburon, COMPOUND OF FORMULA I+nicosulfuron, COMPOUND OF FORMULA I+nonanoic acid, COMPOUND OF FORMULA I+norflurazon, COMPOUND OF FORMULA I+oleic acid (fatty acids), COMPOUND OF FORMULA I+orbencarb, COMPOUND OF FORMULA I+orthosulfamuron, COMPOUND OF FORMULA I+oryzalin, COMPOUND OF FORMULA I+oxadiargyl, COMPOUND OF FORMULA I+oxadiazon, COMPOUND OF FORMULA I+oxasulfuron, COMPOUND OF FORMULA I+oxaziclomefone, COMPOUND OF FORMULA I+oxyfluorfen, COMPOUND OF FORMULA I+paraquat, COMPOUND OF FORMULA I+paraquat dichloride, COMPOUND OF FORMULA I+pebulate, COMPOUND OF FORMULA I+pendimethalin, COMPOUND OF FORMULA I+penoxsulam, COMPOUND OF FORMULA I+pentachlorophenol, COMPOUND OF FORMULA I+pentanochlor, COMPOUND OF FORMULA I+pentoxazone, COMPOUND OF FORMULA I+pethoxamid, COMPOUND OF FORMULA I+petrolium oils, COMPOUND OF FORMULA I+phenmedipham, COMPOUND OF FORMULA I+phenmedipham-ethyl, COMPOUND OF FORMULA I+picloram, COMPOUND OF FORMULA I+picolinafen, COMPOUND OF FORMULA I+pinoxaden, COMPOUND OF FORMULA I+piperophos, COMPOUND OF FORMULA I+potassium arsenite, COMPOUND OF FORMULA I+potassium azide, COMPOUND OF FORMULA I+pretilachlor, COMPOUND OF FORMULA I+primisulfuron, COMPOUND OF FORMULA I+primisulfuron-methyl, COMPOUND OF FORMULA I+prodiamine, COMPOUND OF FORMULA I+profluazol, COMPOUND OF FORMULA I+profoxydim, COMPOUND OF FORMULA I+prometon, COMPOUND OF FORMULA I+prometryn, COMPOUND OF FORMULA I+propachlor, COMPOUND OF FORMULA I+propanil, COMPOUND OF FORMULA I+propaquizafop, COMPOUND OF FORMULA I+propazine, COMPOUND OF FORMULA I+propham, COMPOUND OF FORMULA I+propisochlor, COMPOUND OF FORMULA I+propoxycarbazone, COMPOUND OF FORMULA I+propoxycarbazone-sodium, COMPOUND OF FORMULA I+propyrisulfuron, COMPOUND OF FORMULA I+propyzamide, COMPOUND OF FORMULA I+prosulfocarb, COMPOUND OF FORMULA I+prosulfuron, COMPOUND OF FORMULA I+pyraclonil, COMPOUND OF FORMULA I+pyraflufen, COMPOUND OF FORMULA I+pyraflufen-ethyl, COMPOUND OF FORMULA I+pyrasulfutole, COMPOUND OF FORMULA I+pyrazolynate, COMPOUND OF FORMULA I+pyrazosulfuron, COMPOUND OF FORMULA I+pyrazosulfuron-ethyl, COMPOUND OF FORMULA I+pyrazoxyfen, COMPOUND OF FORMULA I+pyribenzoxim, COMPOUND OF FORMULA I+pyributicarb, COMPOUND OF FORMULA I+pyridafol, COMPOUND OF FORMULA I+pyridate, COMPOUND OF FORMULA I+pyriftalid, COMPOUND OF FORMULA I+pyriminobac, COMPOUND OF FORMULA I+pyriminobac-methyl, COMPOUND OF FORMULA I+pyrimisulfan, COMPOUND OF FORMULA I+pyrithiobac, COMPOUND OF FORMULA I+pyrithiobac-sodium, COMPOUND OF FOR- MULA I+pyroxsulam, COMPOUND OF FORMULA I+pyroxasulfone, COMPOUND OF FORMULA I+quinclorac, COMPOUND OF FORMULA I+quinmerac, COMPOUND OF FORMULA I+quinoclamine, COMPOUND OF FORMULA I+quizalofop, COMPOUND OF FORMULA I+quizalofop-P, COMPOUND OF FORMULA I+rimsulfuron, COMPOUND OF FORMULA I+saflufenacil, COMPOUND OF FORMULA I+sethoxydim, COMPOUND OF FORMULA I+siduron, COMPOUND OF FORMULA I+simazine, COMPOUND OF FORMULA I+simetryn, COMPOUND OF FORMULA I+SMA, COMPOUND OF FORMULA I+sodium arsenite, COMPOUND OF FORMULA I+sodium azide, COMPOUND OF FORMULA I+sodium chlorate, COMPOUND OF FORMULA I+sulcotrione, COMPOUND OF FORMULA I+sulfentrazone, COMPOUND OF FORMULA I+sulfometuron, COMPOUND OF FORMULA I+sulfometuron-methyl, COMPOUND OF FORMULA I+sulfosate, COMPOUND OF FORMULA I+sulfosulfuron, COMPOUND OF FORMULA I+sulfuric acid, COMPOUND OF FORMULA I+tar oils, COMPOUND OF FORMULA I+2,3,6-TBA, COMPOUND OF FORMULA I+TCA, COMPOUND OF FORMULA I+TCA-sodium, COMPOUND OF FORMULA I+tebuthiuron, COMPOUND OF FORMULA I+tefuryltrione, COMPOUND OF FORMULA I+tembotrione, COMPOUND OF FORMULA I+tepraloxydim, COMPOUND OF FORMULA I+terbacil, COMPOUND OF FORMULA I+terbumeton, COMPOUND OF FORMULA I+terbuthylazine, COMPOUND OF FORMULA I+terbutryn, COMPOUND OF FORMULA I+thenylchlor, COMPOUND OF FORMULA I+thiazopyr, COMPOUND OF FORMULA I+thiencarbazone, COMPOUND OF FORMULA I+thiencarbazone-methyl, COMPOUND OF FORMULA I+thifensulfuron, COMPOUND OF FORMULA I+thifensulfuron-methyl, COMPOUND OF FORMULA I+thiobencarb, COMPOUND OF FORMULA I+tiocarbazil, COMPOUND OF FORMULA I+topramezone, COMPOUND OF FORMULA I+tralkoxydim, COMPOUND OF FORMULA I+tri-allate, COMPOUND OF FORMULA I+triasulfuron, COMPOUND OF FORMULA I+triaziflam, COMPOUND OF FORMULA I+tribenuron, COMPOUND OF FORMULA I+tribenuron-methyl, COMPOUND OF FORMULA I+tricamba, COMPOUND OF FORMULA I+triclopyr, COMPOUND OF FORMULA I+trietazine, COMPOUND OF FORMULA I+trifloxysulfuron, COMPOUND OF FORMULA I+trifloxysulfuron-sodium, COMPOUND OF FORMULA I+trifluralin, COMPOUND OF FORMULA I+triflusulfuron, COMPOUND OF FORMULA I+triflusulfuron-methyl, COMPOUND OF FORMULA I+trihydroxytriazine, COMPOUND OF FORMULA I+tritosulfuron, COMPOUND OF FORMULA I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), COMPOUND OF FORMULA I+4-[(4,5-dihydro-3-methoxy-4-methyl-5-oxo)-1H-1,2,4-triazol-1-yl-carbonylsulfamoyl]-5-methylthiophene-3-carboxylic acid (BAY636), COMPOUND OF FORMULA I+BAY747 (CAS RN 335104-84-2), COMPOUND OF FORMULA I+topramezone (CAS RN 210631-68-8), COMPOUND OF FORMULA I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and COMPOUND OF FORMULA I+4-hydroxy-3-[[2-(3-methoxypropyl)-6-(difluoromethyl)-3-pyridinyl]carbonyl]-bicyclo[3.2.1]oct-3-en-2-one.

The compounds of formula (I) according to the invention can also be used in combination with safeners. Preferably, in these mixtures, the compound of the formula (I) is one of those compounds listed in Tables 1 to 28 above. The following mixtures with safeners, especially, come into consideration:

compound of formula (I)+cloquintocet-mexyl, compound of formula (I)+cloquintocet acid and salts thereof, compound of formula (I)+cyprosulfamide, compound of formula (I)+fenchlorazole-ethyl, compound of formula (I)+fenchlorazole acid and salts thereof, compound of formula (I)+mefenpyr-diethyl, compound of formula (I)+mefenpyr diacid, compound of formula (I)+isoxadifen-ethyl, compound of formula (I)+isoxadifen acid, compound of formula (I)+furilazole, compound of formula (I)+furilazole R isomer, compound of formula (I)+benoxacor, compound of formula (I)+dichlormid, compound of formula (I)+AD-67, compound of formula (I)+oxabetrinil, compound of formula (I)+cyometrinil, compound of formula (I)+cyometrinil Z-isomer, compound of formula (I)+fenclorim, compound of formula (I)+cyprosulfamide, compound of formula (I)+naphthalic anhydride, compound of formula (I)+flurazole, compound of formula (I)+N-(2-methoxybenzoyl)-4-[(methylaminocarbonyl)amino]benzenesulfonamide, compound of formula (I)+CL 304,415, compound of formula (I)+dicyclonon, compound of formula (I)+fluxofenim, compound of formula (I)+DKA-24, compound of formula (I)+R-29148 and compound of formula (I)+PPG-1292. A safening effect can also be observed for the mixtures compound of the formula (I)+dymron, compound of the formula (I)+MCPA, compound of the formula (I)+mecopropand compound of the formula (I)+mecoprop-P.

The mixing partners of the compound of formula I may also be in the form of esters or salts, as mentioned e.g. in The Pesticide Manual, 12th Edition (BCPC), 2000.

In the above different lists of active ingredients to be mixed with a COMPOUND OF FORMULA I, the compound of the formula I is preferably a compound of Tables 1 to 28, whereby G can be hydrogen, C(O)OEt or C(O)OiPr.

In the above-mentioned mixtures of compounds of formula I, in particular a compound selected from said Tables 1 to 28, with other insecticides, fungicides, herbicides, safeners, adjuvants and the like, the mixing ratios can vary over a large range and are, preferably 100:1 to 1:6000, especially 50:1 to 1:50, more especially 20:1 to 1:20, even more especially 10:1 to 1:10. Those mixing ratios are understood to include, on the one hand, ratios by weight and also, on other hand, molar ratios.

The mixtures can advantageously be used in the above-mentioned formulations (in which case "active ingredient" relates to the respective mixture of compound of formula I with the mixing partner).

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The mixtures comprising a compound of formula I selected from Tables 1 to 28 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 28 and the active ingredients as described above is not essential for working the present invention.

The invention is illustrated by the following preparation examples. The H-NMR data of certain compounds of this invention show line broadening at room temperature, suggesting the existence of plural conformational isomers due to, for example keto-enol tautomerism, hindered rotation, ring inversion in the piperidine moitey or nitrogen inversion at the piperidine N—OR center. Broad signals have been labeled with 'br' accordingly.

EXAMPLE 1

Preparation of Carbonic acid 3-(2,5-dimethyl-phenyl)-8-methoxy-2-oxo-1-oxa-8-aza-spiro[4.5]dec-3-en-4-yl ester ethyl ester (compound P1.1)

Step 1: Preparation of 1-methoxy-4-trimethylsilanyloxy-piperidine-4-carbonitrile (compound P4.1)

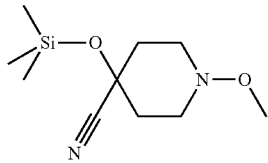

To a solution of 1-methoxy-piperidin-4-one (10.0 g, 77.4 mmol, prepared according to J. Org. Chem. 1961, 26, 1867-74) in 100 ml dichloromethane was added anhydrous $ZnCl_2$ (1.24 g, 3.9 mmol) under argon. Then trimethylsilyl cyanide $Me_3Si$—CN (9.21 g, 92.9 mmol) was added dropwise. During the addition the temperature slightly increased to 28° C. The reaction was left stirring at room temperature overnight. Then it was poured into cold (0° C.) water and stirred for 30 minutes. The aqueous phase was carefully extracted three times with dichloromethane. The combined organic layers were dried over magnesium sulfate and concentrated in vacuum. The crude product (yellow liquid) was used directly without further purification. Yield: 14.4 g of 1-methoxy-4-trimethylsilanyloxy-piperidine-4-carbonitrile (compound P4.1).

$^1$H-NMR ($CDCl_3$): δ ppm 0.25 (s, 9H), 1.76-2.30 (m, 4H), 2.70-3.34 (m, 4H), 3.51 (s, 3H).

Step 2: Preparation of 4-hydroxy-1-methoxy-piperidine-4-carbonitrile (compound P4.2)

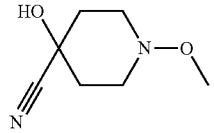

1-Methoxy-4-trimethylsilanyloxy-piperidine-4-carbonitrile (1.0 g, 4.4 mmol) was slowly added to aqueous HCl (3N) at 15° C. The mixture was stirred for two hours at room temperature and then poured into cold (0° C.) water. Sodium hydrogen sulfate (saturated aqueous solution) was slowly added to adjust the pH to 7. The aqueous layer was carefully extracted with ethyl acetate three times. All organic layers were combined, dried over magnesium sulfate and concentrated. The crude product (ca 94% pure) was used directly for the next step without further purification. Yield: 500 mg of 4-hydroxy-1-methoxy-piperidine-4-carbonitrile (compound P4.2) as light yellow solid.

$^1$H-NMR ($CDCl_3$): δ ppm 1.80-2.34 (br m, 4H), 2.73-3.20 (m, 2H), 3.51 (s, 3H).

$^{13}$C-NMR ($CDCl_3$): δ ppm 38.3, 49.7, 53.9, 59.3, 121.4.

Step 3: Preparation of 4-hydroxy-1-methoxy-piperidine-4-carboxylic acid ethyl ester (compound P4.3)

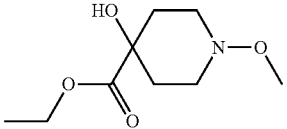

To a solution of 4-hydroxy-1-methoxy-piperidine-4-carbonitrile (13.40 g, 85.8 mmol) in 100 ml ethanol was introduced gaseous HCl at −20° C. for about 30 minutes. The reaction mixture was stirred for one hour at ca −10 to −20° C. and became light brown. Then once again gaseous HCl was introduced into the reaction mixture for 30 minutes and the whole was left stirring at room temperature overnight. The solvent was evaporated at 40° C. under vacuum and ice was added to the residue. The pH was adjusted to ca 5.5 and the aqueous phase extracted three times thoroughly with dichloromethane. The organic layers were combined, washed with brine, dried over sodium sulfate and concentrated. The crude product (brown oil) was purified by column chromatography on silica gel (ethyl acetate/cyclohexane 1:3). Yield: 7.2 g of 4-hydroxy-1-methoxy-piperidine-4-carboxylic acid ethyl ester (compound P4.3) as light yellow oil.

$^1$H-NMR ($CDCl_3$): δ ppm 1.25 (t, 3H), 1.25-1.75 (m, 2H), 2.03-2.2.40 (m, 2H), 2.65-3.27 (m, 4H+OH), 3.52 (br s, 3H), 4.19 (q, 2H).

$^{13}$C-NMR ($CDCl_3$): δ ppm 14.0, 34.3, 50.6, 59.0, 70.4, 176.4.

LC/MS (ES+): 204 (M+H)$^+$

FTIR: ν(C═O) 1728 cm$^{-1}$, ν(OH$_{ass}$) 3480 cm$^{-1}$

Step 4: Preparation of 4-[2-(2,5-dimethyl-phenyl)-acetoxy]-1-methoxy-piperidine-4-carboxylic acid ethyl ester (compound P3.1)

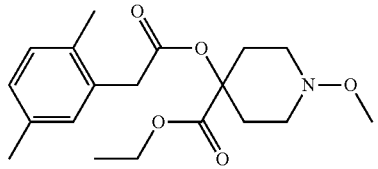 [SMILES: CCOC(=O)C1(OC(=O)Cc2cc(C)ccc2C)CCN(OC)CC1]

To a solution of 4-hydroxy-1-methoxy-piperidine-4-carboxylic acid ethyl ester (1.0 g, 4.92 mmol) in 10 ml pyridine under argon was added 4-dimethylaminopyridine DMAP (30 mg, 0.25 mmol). The solution was cooled down to 0° C., then (2,5-dimethyl-phenyl)-acetyl chloride (0.99 g, 5.4 mmol) was added dropwise. The reaction mixture was warmed up to room temperature and left stirring for 5 days. Then the reaction mixture was concentrated and the crude product was purified by column chromatography on silica gel (ethyl acetate/cyclohexane first 1:15, then 1:9) to give pure 4-[2-(2, 5-dimethyl-phenyl)-acetoxy]-1-methoxy-piperidine-4-carboxylic acid ethyl ester (compound P3.2) as light yellow oil. Yield: 530 mg.

¹H-NMR (CDCl₃): δ ppm 1.70-3.24 (br m, 8H, mixture of conformers), 2.29 (s, 3H), 2.30 (s, 3H), 3.52 (br s, 3H), 3.65 (s, 2H), 4.13 (q, 2H), 6.94-7.10 (m, 3H).

LC/MS (ES+): 350 (M+H)⁺

Step 5: Preparation of 3-(2,5-dimethyl-phenyl)-4-hydroxy-8-methoxy-1-oxa-8-aza-spiro[4.5]dec-3-en-2-one (compound P2.1)

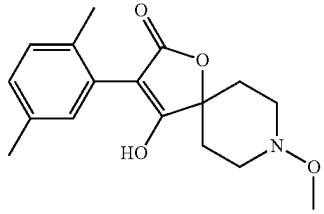

To a solution of 4-[2-(2,5-dimethyl-phenyl)-acetoxy]-1-methoxy-piperidine-4-carboxylic acid ethyl ester (84 mg, 0.24 mmol) in THF (3 ml) at 0° C. was added portionwise potassium tert-butoxide (57 mg, 0.48 mmol) under argon. After the addition, stirring was continued at 0° C. for 15 minutes. Then the reaction mixture was warmed up to room temperature, stirred for one hour and for additional two hours at reflux. The reaction mixture was poured into cold water (0° C.), the pH adjusted to ca 6 by adding 1 N HCl and then thoroughly extracted three times with dichloromethane. The combined organic layers were dried over magnesium sulfate, filtered and concentrated. The resulting crude material (resin) was triturated with cyclohexane/ethyl acetate (ca 1:1), filtered and dried to give a white solid. Yield: 50 mg of 3-(2,5-dimethyl-phenyl)-4-hydroxy-8-methoxy-1-oxa-8-aza-spiro[4.5]dec-3-en-2-one (compound P2.1), mp 205-208° C.

¹H-NMR (CD₃OD): δ ppm 1.58-2.85 (br m, 4H, mixture of conformers), 2.19 (s, 3H), 2.33 (s, 3H), 2.70-2.85 (br m, 1H), 3.13-3.30 (br m, 1H, covered in part by solvent peak), 2.88-2.99 (br m, 2H), 3.59 (s, 3H), 6.99 (s, 1H), 7.10 (d, 1H), 7.17 (d, 1H).

LC/MS (ES+): 304 (M+H)⁺

Step 6: Preparation of carbonic acid 3-(2,5-dimethyl-phenyl)-8-methoxy-2-oxo-1-oxa-8-aza-spiro[4.5]dec-3-en-4-yl ester ethyl ester (title compound P1.1)

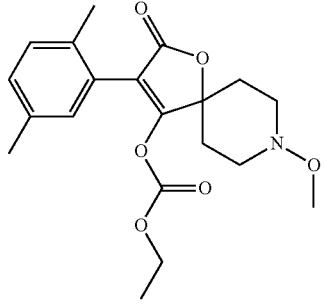 [SMILES: CCOC(=O)OC1=C(c2cc(C)ccc2C)C(=O)OC12CCN(OC)CC2]

To a solution of 3-(2,5-dimethyl-phenyl)-4-hydroxy-8-methoxy-1-oxa-8-aza-spiro[4.5]dec-3-en-2-one (120 mg, 0.40 mmol), triethylamine (0.08 ml, 60 mg, 0.60 mmol) and 4-dimethylaminopyridine DMAP (2 mg, 0.02 mmol) in 4 ml THF at 0° C. was added a solution of ethyl chloroformate (0.05 ml, 52 mg, 0.50 mmol) dissolved in 1 ml THF dropwise. The suspension was kept at 0° C. for 30 minutes under argon and left stirring at room temperature overnight. Then the solvent was removed under vacuum. Ethyl acetate was added to the residue and the precipitation was filtered off. The filtrate was concentrated under vacuum to give the crude product, which was purified by column chromatography on silica gel (ethyl acetate/cyclohexane 1:9). Yield: 111 mg of carbonic acid 3-(2,5-dimethylphenyl)-8-methoxy-2-oxo-1-oxa-8-aza-spiro[4.5]dec-3-en-4-yl ester ethyl ester (title compound P1.1) as a light yellow gum.

¹H-NMR (CDCl₃): δ ppm 1.11 (t, 3H), 1.35-1.90 (br m, 2H), 2.15-2.92 (br, m, 3H), 3.18-3.45 (br m, 3H), 3.55 (br s, 3H), 4.03 (q, 2H), 6.96 (s, 1H), 7.08 (s, 1H), 7.12 (s, 1H).

LC/MS (ES+): 376 (M+H)⁺

EXAMPLE 2

Preparation of 4-Hydroxy-8-methoxy-3-(2,4,5-trimethyl-phenyl)-1-oxa-8-aza-spiro[4.5]dec-3-en-2-one (compound P2.2)

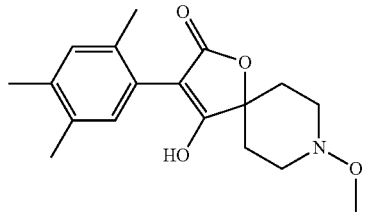

To a solution of (2,4,5-trimethyl-phenyl)acetic acid methyl ester (0.6 g, 3.12 mmol) and 4-hydroxy-1-methoxy-piperidine-4-carboxylic acid ethyl ester (0.76 g, 3.74 mmol) in 7 ml anhydrous THF was added a 1 M solution of potassium tert-butoxide (6.9 ml, 8.87 mmol) in THF at room temperature. The suspension obtained was first stirred at room temperature for one hour, and then refluxed under argon for one hour. After cooling to room temperature, the reaction mixture was concentrated, water was added and the mixture acidified with little HCl (37%). The aqueous layer was extracted with dichloromethane, and the combined organic layers were then washed with brine and dried over sodium sulfate. After filtration and concentration under vacuum, the residue was purified by column chromatography (silica gel, ethyl acetate 100%). Yield: 280 mg of 4-hydroxy-8-methoxy-3-(2,4,5-trimethyl-phenyl)-1-oxa-8-aza-spiro[4.5]dec-3-en-2-one (title compound P2.2) as a white solid, mp 199-204° C.

¹H-NMR (CDCl₃): δ ppm 1.30-2.60 (br m, 4H), 2.17 (s, 3H), 2.22 (s, 6H), 2.78-3.40 (br m, 4H), 3.55 (br s, 3H), 6.92 (s, 1H), 7.05 (s, 1H).

LC/MS (ES+): 318 (M+H)⁺

EXAMPLE 3

Preparation of Carbonic acid ethyl ester 8-methoxy-2-oxo-3-(2,4,6-trimethylphenyl)-1-oxa-8-aza-spiro [4.5]dec-3-en-4-yl ester (compound P1.5)

Step 1: Preparation of (2,4,6-trimethyl-phenyl)-acetic acid 4-cyano-1-methoxy-piperidin-4-yl ester (compound P3.4)

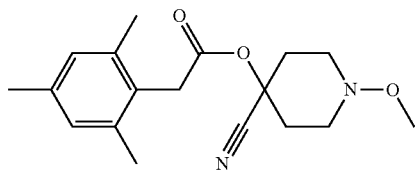

To a cooled (−20° C.) solution of 4-hydroxy-1-methoxy-piperidine-4-carbonitrile (0.32 g, 2.05 mmol) in 2 ml dichloromethane was added 4-dimethylaminopyridine DMAP (13 mg, 0.05 mmol) under argon. Then (2,4,6-trimethyl-phenyl)-acetyl chloride (0.52 g, 2.64 mmol) dissolved in dichloromethane (3 ml) was added dropwise. The reaction mixture was stirred at −20° C. for 30 minutes, then 30 minutes at 0° C. and finally left stirring overnight at room temperature. The reaction mixture was poured into water and extracted three times with dichloromethane. The combined organic layers were dried over sodium sulfate, filtered and concentrated under vacuum. The crude product was purified by column chromatography on silica gel to give pure (2,4,6-trimethyl-phenyl)-acetic acid 4-cyano-1-methoxy-piperidin-4-yl ester (compound P3.5) as white solid, mp 75-78° C. Yield: 480 mg.

$^1$H-NMR (CDCl$_3$): δ ppm 1.84-2.02 (br m, 1H), 2.06-2.20 (br m, 1H), 2.30-258 (br m, 2H), 2.27 (s, 3H), 2.29 (s, 6H), 2.62-3.24 (br m, 4H), 3.50 (s, 3H), 3.73 (s, 2H), 6.96 (s, 2H).

LC/MS (ES+): 317 (M+H)$^+$

Step 2: Preparation of 1-methoxy-4-[2-(2,4,6-trimethyl-phenyl)-acetoxy]-piperidine-4-carboxylic acid ethyl ester (compound P3.5)

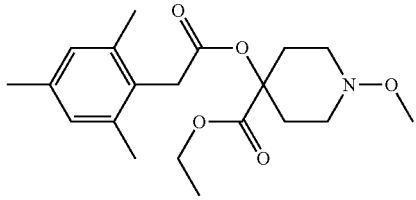

Method A:

To a solution of (2,4,6-trimethyl-phenyl)-acetic acid 4-cyano-1-methoxypiperidin-4-yl ester (1.30 g, 4.11 mmol) in 25 ml ethanol was introduced gaseous HCl at −20° C. for about two hours, and then left stirring at room temperature overnight. The solvent was evaporated at 40° C. under vacuum and ice was added to the residue. The reaction mixture was stirred for 45 minutes, the pH adjusted to ca 5.5 and the aqueous phase extracted three times thoroughly with dichloromethane. The organic layers were combined, washed with brine, dried over sodium sulfate and concentrated. The crude product was used directly for the next step without purification. Yield: 1.2 g (ca 50% purity) of 1-methoxy-4-[2-(2,4,6-trimethyl-phenyl)-acetoxy]-piperidine-4-carboxylic acid ethyl ester (compound P3.6) as brown oil (the product is contaminated with (2,4,6-trimethyl-phenyl)acetic acid 4-carbamoyl-1-methoxy-piperidin-4-yl ester).

$^1$H-NMR (CDCl$_3$, selected peaks): δ ppm 1.18 (t, 3H), 2.25 (s, 3H), 2.29 (s, 6H), 4.13 (q, 2H), 6.85 (s, 2H).

LC/MS (ES+): 364 (M+H)$^+$

Method B:

To a solution of 4-hydroxy-1-methoxy-piperidine-4-carboxylic acid ethyl ester (0.5 g, 2.46 mmol) in 15 ml pyridine under argon was added 4-dimethylaminopyridine DMAP (0.11 g, 0.9 mmol). The solution was cooled down to 0° C., then (2,4,6-trimethylphenyl)-acetyl chloride (0.58 g, 2.95 mmol) was added dropwise. The reaction mixture was warmed up to room temperature and left stirring for 3 days. Then the reaction mixture was concentrated and cold (0° C.) water was added. The aqueous phase was thoroughly extracted three times with dichloromethane. The organic layers were combined, washed with brine, dried over sodium sulfate and concentrated. The crude product was purified by column chromatography on silica gel (ethyl acetate/cyclohexane 1:4) to give pure 1-methoxy-4-[2-(2,4,6-trimethyl-phenyl)-acetoxy]-piperidine-4-carboxylic acid ethyl ester (compound P3.6) as light yellow oil. Yield: 610 mg.

$^1$H-NMR (CDCl$_3$): δ ppm 1.18 (t, 3H), 1.69-2.44 (br m, 4H), 2.25 (s, 3H), 2.29 (s, 6H), 2.44-3.27 (br m, 4H), 3.51 (br s, 3H), 3.69 (s, 2H), 4.13 (q, 2H), 6.85 (s, 2H).

LC/MS (ES+): 364 (M+H)$^+$

Step 3: Preparation of 4-hydroxy-8-methoxy-3-(2,4,6-trimethyl-phenyl)-1-oxa-8-aza-spiro[4.5]dec-3-en-2-one (compound P2.3)

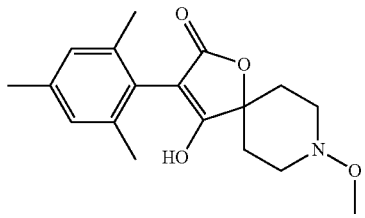

Method A:

To a suspension of crude (ca 50% purity) 1-methoxy-4-[2-(2,4,6-trimethylphenyl)-acetoxy]-piperidine-4-carboxylic acid ethyl ester (1.12 g, 3.0 mmol) in dimethylformamide (2 ml) at 0° C. under argon was added portionwise potassium tert-butoxide (1.04 g, 9.24 mmol). After completion of the addition, the reaction mixture was warmed up to room temperature and left stirring for one hour. The reaction mixture was poured into cold water (0° C.) and acidified with aqueous HCl (1N) to adjust the pH to ca 5.5. Then the reaction mixture was thoroughly extracted with ethyl acetate (three times). The combined organic layers were washed with brine, dried over sodium sulfate and concentrated. The resulting crude material (ca 50% purity) was directly used for the preparation of compound P1.5. Yield: 1.0 g of 4-hydroxy-8-methoxy-3-(2,4,6-trimethylphenyl)-1-oxa-8-aza-spiro[4.5]dec-3-en-2-one (compound P2.3) as light yellow solid.

$^1$H-NMR (CDCl$_3$, selected peaks): δ ppm 2.12 (s, 6H), 2.25 (s, 3H), 2.18 (s, 6H), 3.51 (br s, 3H), 6.89 (s, 2H).

FIMS (ES+): 318 (M+H)$^+$

Method B:

To a solution of carbonic acid ethyl ester 8-methoxy-2-oxo-3-(2,4,6-trimethylphenyl)-1-oxa-8-aza-spiro[4.5]dec-3-en-4-yl ester (compound P1.5) (108 mg, 0.30 mmol) in THF (3 ml) at room temperature was added dropwise LiOH dissolved in 1 ml H$_2$O. After the addition, the reaction mixture was left stirring for 30 minutes at room temperature. The reaction mixture was acidified with aqueous HCl (1N) to adjust the pH to ca 6. The reaction mixture was reduced to ⅔ of the original volume, poured into cold water (0° C.) and then thoroughly extracted with ethyl acetate. The combined organic layers were dried over magnesium sulfate and concentrated. Yield: 59 mg of 4-hydroxy-8-methoxy-3-(2,4,6-trimethyl-phenyl)-1-oxa-8-aza-spiro[4.5]dec-3-en-2-one (compound P2.3) as amorphous solid.

$^1$H-NMR (CDCl$_3$, selected peaks): δ ppm 2.12 (s, 6H), 2.25 (s, 3H), 2.18 (s, 6H), 3.51 (br s, 3H), 6.89 (s, 2H).

FIMS (ES+): 318 (M+H)$^+$

Method C:

To a solution of (2,4,6-trimethyl-phenyl)acetic acid methyl ester (0.2 g, 1.04 mmol) and 4-hydroxy-1-methoxy-piperidine-4-carboxylic acid methyl ester (0.24 g, 1.25 mmol) in 3 ml anhydrous THF was added a 1 M solution of potassium tert-butoxide (2.3 ml, 2.29 mmol) in THF at room temperature. The suspension obtained was first stirred at room temperature for one hour, refluxed under argon for two hours, and then left stirring at room temperature overnight. The reaction mixture was concentrated, water was added and the mixture acidified with little HCl (37%) to adjust the pH to ca 5.5. The aqueous layer was extracted with dichloromethane three times. The combined organic layers were then washed with brine and dried over sodium sulfate. After filtration and concentration under vacuum, the residue was purified by column chromatography (silica gel; first ethyl acetate/cyclohexane 1:1, then ethyl acetate 100%). Yield: 130 mg of 4-hydroxy-8-methoxy-3-(2,4,6-trimethyl-phenyl)-1-oxa-8-aza-spiro[4.5]dec-3-en-2-one (compound P2.3) as a light yellow solid, mp 197-201° C.

$^1$H-NMR (CD$_3$OD): δ ppm 1.61-2.71 (br m, 5H), 2.01 (s, 6H), 2.18 (s, 3H), 3.0-3.37 (br m, 3H), 3.45 (s, 3H), 6.81 (s, 2H).

LC/MS (ES+): 318 (M+H)$^+$

Step 4: Preparation of carbonic acid ethyl ester 8-methoxy-2-oxo-3-(2,4,6-trimethylphenyl)-1-oxa-8-aza-spiro[4.5]dec-3-en-4-yl ester (title compound P1.5)

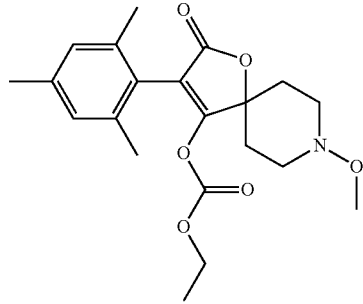

To a solution of crude (ca 50% purity) 4-hydroxy-8-methoxy-3-(2,4,6-trimethyl-phenyl)-1-oxa-8-aza-spiro[4.5]dec-3-en-2-one (1.0 g, 3.15 mmol), triethylamine (0.8 ml, 0.57 g, 5.67 mmol) in 6 ml THF at 0° C. under argon was added ethyl chloroformate (0.36 ml, 0.41 g, 3.78 mmol) dropwise. The suspension became immediately quite thick. It was diluted with additional 2 ml THF while stirring was continued at 0° C. for 30 minutes. The reaction mixture was poured into cold water (0° C.) and extracted three times with ethyl acetate. The combined organic layers were dried over sodium sulfate and concentrated. The crude product (brown oil) was purified by column chromatography on silica gel (ethyl acetate/cyclohexane 1:1). Yield: 220 mg of carbonic acid ethyl ester 8-methoxy-2-oxo-3-(2,4,6-trimethyl-phenyl)-1-oxa-8-aza-spiro[4.5]dec-3-en-4-yl ester (title compound P1.5) as a white solid.

$^1$H-NMR (CDCl$_3$): δ ppm 1.11 (t, 3H), 1.75-2.95 (br m, 4H), 2.15 (s, 6H), 2.26 (s, 3H), 3.13-3.70 (br m, 4H), 3.58 (s, 3H), 4.01 (q, 2H), 6.86 (s, 2H).

LC/MS (ES+): 390 (M+H)$^+$

EXAMPLE 4

Preparation of Carbonic acid ethyl ester 8-methoxy-2-oxo-3-(2,4,6-trimethylphenyl)-1-thia-8-aza-spiro[4.5]dec-3-en-4-yl ester (compound P1.7)

Step 1: Preparation of 1-methoxy-piperidin-4-ol

Under an atmosphere of argon, 200 ml ethanol was cooled to 10° C. and 3.7 g sodium borohydride was added. A solution of 25 g 1-methoxy-piperidin-4-one (prepared according to J. Org. Chem. 1961, 26, 1867-74) in 200 ml ethanol was added to the stirred suspension, while the temperature was kept in the range of 15-20° C. Then the mixture was stirred at ambient temperature for 3 hours. 50 ml aqueous ammonium chloride was added slowly and then the solvent evaporated. The residue was purified by chromatography on silica gel, using ethyl acetate as a solvent. Thus, 22.8 g 1-methoxy-piperidin-4-ol was obtained.

$^1$H-NMR (CDCl$_3$): δ ppm 1.50-3.90 (br m signals, total 10H), 3.53 (s, 3H).

Step 2: Preparation of methanesulfonic acid 1-methoxy-piperidin-4-yl ester

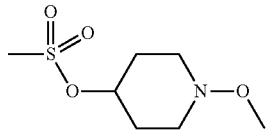

21 g 1-Methoxy-piperidin-4-ol (from Step 1) and 19.4 g triethylamine were dissolved in 200 ml ethyl acetate, and cooled to 0° C. 15.0 g Methanesulfonyl chloride was added slowly. The resulting white suspension was stirred at 0° C. for 1 hour, then at room temperature for an additional 1 hour. Then the mixture was filtered and the solvent evaporated, yielding 34.6 g of methanesulfonic acid 1-methoxy-piperidin-4-yl ester. This material was used for the next step without further purification.

$^1$H-NMR (CDCl$_3$): δ ppm 1.70-4.90 (br m signals, total 9H), 3.03 (s, 3H), 3.52 (s, 3H).

Step 3: Preparation of 1-methoxy-piperidine-4-carbonitrile

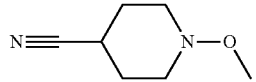

Method A: 200 mg Methanesulfonic acid 1-methoxy-piperidin-4-yl ester (from Step 2), 251 mg tetrabutylammonium cyanide and 272 mg sodium cyanide were mixed in 1 ml dimethylsulfoxide, and heated to 55° C. for 18 hours. Then the mixture was cooled to room temperature, 1 ml saturated aqueous sodium bicarbonate and 3 ml water were added, and extracted three times with diethyl ether. The organic layer was dried over anhydrous sodium sulfate and the solvent evaporated. The residue was purified by chromatography on silica gel with ethyl acetate/cyclohexane (1:1, then 2:1, then pure ethyl acetate) as a solvent. 116 mg 1-methoxy-piperidine-4-carbonitrile was obtained.

$^1$H-NMR (CDCl$_3$): δ ppm 1.85 (br m, 2H), 2.13 (br m, 1H), 2.40 (br m, 2H), 2.80 (br m, 2H), 3.20 (br m, 1H), 3.35 (br m, 1H), 3.51 (s, 3H).

Method B: To a solution of 1-methoxy-piperidin-4-one (5.0 g, 38.71 mmol, prepared according to J. Org. Chem. 1961, 26, 1867-74) and tosylmethyl isocyanide (TosMIC, 10.13 g, 50.33 mmol) in a mixture of 1,2-dimethoxyethane (100 ml, DME) and ethanol (3 ml) kept at 5-10° C. was added solid potassium tert-butoxide (8.78 g, 77.42 mmol) in portions. The suspension was stirred at room temperature for 30 minutes, then at 35-40° C. for further 30 minutes. The cooled precipitate was removed by filtration and washed with DME. The combined DME solutions were concentrated in vacuo, the residue triturated with hexane/ether 1:2 and the precipitate further removed by filtration. The filtrate was treated with charcoal, stirred, filtered and concentrated. Yield: 4.5 g of 1-methoxy-piperidine-4-carbonitrile as a colorless oil. The spectral data for this material were identical to those described above under preparation example 4, step 3, Method A.

FTIR: ν(CN) 2239 cm$^{-1}$. LC/MS (ES+): 141 (M+H)$^+$

Step 4: Preparation of
1-methoxy-piperidine-4-carboxylic acid methyl ester

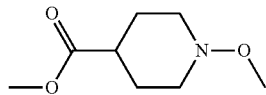

1 g 1-Methoxy-piperidine-4-carbonitrile (from Step 3) was dissolved in 10 ml methanol, and 2.66 ml concentrated sulfuric acid was added dropwise. The mixture was stirred at 55° C. for 6 days, then cooled to ambient temperature and poured on ice. The pH was adjusted to 4.3 by the addition of aqueous sodium hydroxide (30% w/w). The mixture was extracted with ethyl acetate, the organic layer dried over sodium sulfate, and the solvent evaporated. The residue was chromatographed on silica gel with ethyl acetate/cyclohexane (1:9, then 1:5, then 1:2) as a solvent. 729 mg 1-methoxy-piperidine-4-carboxylic acid methyl ester was obtained as an oil.

$^1$H-NMR (CDCl$_3$): δ ppm 1.75-3.05 (br m, total 7H), 3.38 (m, 2H), 3.52 (s, 3H), 3.67 (s, 3H).

Step 5: Preparation of 1-methoxy-4-(4-methoxy-benzylsulfanyl)-piperidine-4-carboxylic acid

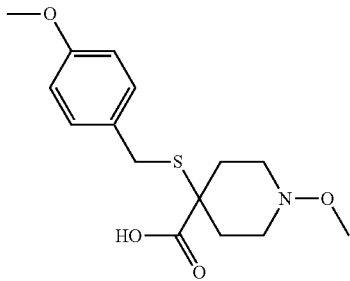

Under an atmosphere of argon, 0.55 g diisopropylamine was added to 12 ml tetrahydrofuran, and cooled to −70° C. Then 2.6 ml n-butyllithium (1.6M in hexane) was added, and the mixture warmed to −5° C., then cooled to −75° C. A solution of 720 mg 1-methoxy-piperidine-4-carboxylic acid methyl ester (from Step 4) in 3 ml tetrahydrofuran was added, and the mixture stirred at −75° C. for 1 hour. Then 1.26 g bis(4-methoxybenzyl)disulfide was added and the mixture warmed to room temperature. Then the mixture was extracted with water and t-butylmethyl ether, the organic layer dried over sodium sulfate, and the solvent evaporated. The oily residue was dissolved in 18 ml methanol, 1.07 g potassium hydroxide was added, and the mixture heated on reflux for 18 hours. Then the mixture was cooled to room temperature, evaporated, and the residue dissolved in water. The pH was adjusted to 5.3 by the addition of aqueous hydrochloric acid. The resulting suspension was extracted with ethyl acetate, dried over sodium sulfate and evaporated. The residue was suspended in t-butylmethyl ether, filtered and dried. Thus, 462 mg 1-methoxy-4-(4-methoxy-benzylsulfanyl)-piperidine-4-carboxylic acid was obtained as a white solid.

$^1$H-NMR (DMSO-d$_6$): δ ppm 1.60-3.23 (br m signals, total 9H), 3.40 (s, 3H), 3.72 (s, 3H), 3.76 (br s, 2H), 6.87 (d, 2H), 7.20 (d, 2H).

Step 6: Preparation of 3-[1-methoxy-4-(4-methoxy-benzylsulfanyl)-piperidin-4-yl]-3-oxo-2-(2,4,6-trimethyl-phenyl)-propionic acid methyl ester

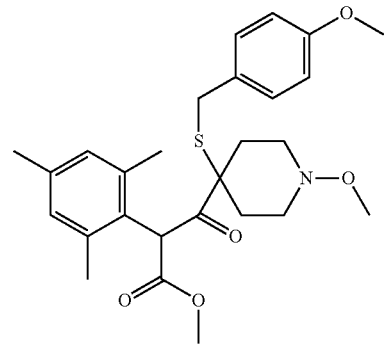

700 mg 1-Methoxy-4-(4-methoxy-benzylsulfanyl)-piperidine-4-carboxylic acid (from Step 5) was dissolved in 10 ml toluene, 1 drop N,N-dimethylformamide was added, followed by 400 mg thionyl chloride. The mixture was heated to 100° C. for 1 hour, at which time the evolution of gas has ceased. The solvent was evaporated, to yield crude 1-methoxy-4-(4-methoxy-benzylsulfanyl)-piperidine-4-carbonyl chloride.

In a separate flask, 512 mg diisopropylamine was dissolved in 15 ml tetrahydrofuran, cooled to −5° C., and 2.86 ml n-butyllithium (1.6M in hexane) was added, then stirred at 0° C. for 1 hour. Then 864 mg (2,4,6-trimethyl-phenyl)-acetic acid methyl ester was added, and the mixture stirred for additional 30 minutes at 0° C. The crude 1-methoxy-4-(4-methoxybenzylsulfanyl)-piperidine-4-carbonyl chloride was dissolved in 5 ml tetrahydrofuran and added to the reaction mixture, which was then allowed to warm to room temperature and stirred for 18 hours. The solvent was evaporated, the residue partitioned between half saturated aqueous ammonium chloride and t-butylmethyl ether, the organic layer washed with brine, dried over sodium sulfate, and evaporated. The residue was chromatographed on silica gel with ethyl acetate/cyclohexane (1:9, then 1:5, then 1:2) as a solvent. Thus, 508 mg 3-[1-methoxy-4-(4-methoxy-benzylsulfanyl)-piperidin-4-yl]-3-oxo-2-(2,4,6-trimethylphenyl)-propionic acid methyl ester was obtained.

$^1$H-NMR (CDCl$_3$): δ ppm 1.60-3.50 (br m signals, total 8H), 2.24 (s, 6H), 2.34 (s, 3H), 3.50 (s, 3H), 3.70 (s, 3H), 3.73 (br s, 2H), 3.77 (s, 3H), 6.00 (br s, 1H), 6.80 (d, 2H), 6.87 (s, 2H), 7.20 (d, 2H).

Step 7: Preparation of 4-hydroxy-8-methoxy-3-(2,4,6-trimethyl-phenyl)-1-thia-8-aza-spiro[4.5]dec-3-en-2-one (compound P2.4)

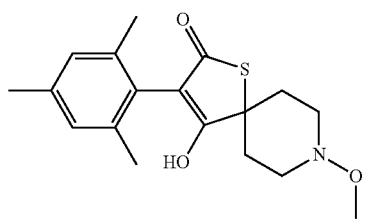

470 mg 3-[1-Methoxy-4-(4-methoxy-benzylsulfanyl)-piperidin-4-yl]-3-oxo-2-(2,4,6-trimethylphenyl)-propionic acid methyl ester (from Step 6) was dissolved in 15 ml trifluoroacetic acid and heated on reflux for 18 hours. The mixture was cooled to room temperature, diluted with water, the pH adjusted to 4.2 by the addition of aqueous sodium hydroxide, then extracted with t-butylmethyl ether. The organic layer was dried over anhydrous sodium sulfate, and the solvent evaporated. The residue was chromatographed on silica gel with ethyl acetate/cyclohexane (1:1, then 2:1) as a solvent, to yield 156 mg 4-hydroxy-8-methoxy-3-(2,4,6-trimethyl-phenyl)-1-thia-8-aza-spiro[4.5]dec-3-en-2-one (compound P2.4) as a solid, mp 67-71° C.

$^1$H-NMR (methanol-d$_4$): δ ppm 2.00-3.60 (br m signals, total 8H), 2.10 (s, 6H), 2.30 (s, 3H), 3.60 (br s, 3H), 6.94 (s, 2H).

LC/MS (ES+): 334 (M+H)$^+$

Step 8: Preparation of carbonic acid ethyl ester 8-methoxy-2-oxo-3-(2,4,6-trimethylphenyl)-1-thia-8-aza-spiro[4.5]dec-3-en-4-yl ester (title compound P1.7)

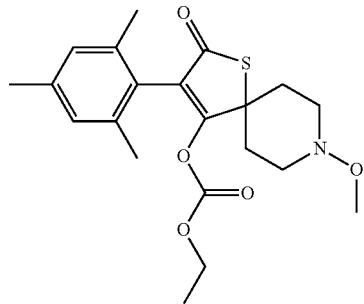

94 mg 4-Hydroxy-8-methoxy-3-(2,4,6-trimethyl-phenyl)-1-thia-8-aza-spiro[4.5]dec-3-en-2-one (from Step 7) and 43 mg triethylamine were dissolved in 10 ml tetrahydrofuran, and a solution of 32 mg ethyl chloroformate in 5 ml tetrahydrofuran was added dropwise. The mixture was stirred at ambient temperature for 18 hours, then partitioned between saturated aqueous sodium bicarbonate and t-butylmethyl ether, the organic layer dried over sodium sulfate, and the solvent evaporated. The residue was purified by chromatography on silica gel with ethylacetate/cyclohexane (1:2) as a solvent, to give 34 mg carbonic acid ethyl ester 8-methoxy-2-oxo-3-(2,4,6-trimethyl-phenyl)-1-thia-8-aza-spiro[4.5]dec-3-en-4-yl ester (title compound P1.7) as a solid, mp 87-89° C.

$^1$H-NMR (CDCl$_3$): δ ppm 0.95 (t, 3H), 1.86 (br m, 2H), 2.05 (s, 6H), 2.18 (s, 3H), 2.50 (br m, 4H), 3.47 (br m, 2H), 3.50 (br s, 3H), 3.87 (q, 2H), 6.78 (s, 2H).

LC/MS (ES+): 406 (M+H)$^+$

EXAMPLE 5

Preparation of 4-Hydroxy-1-methoxy-piperidine-4-carboxylic acid methyl ester (compound P4.4)

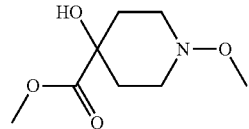

Acetyl chloride (40.7 g, 0.52 mol) was added slowly to dry methanol (115 ml) cooled to 0° C. under argon. After the addition, the solution was stirred for an additional ½ hour at 0° C. This solution was then added dropwise into a cold (0° C.) solution of 4-hydroxy-1-methoxypiperidine-4-carbonitrile (5.40 g, 34.6 mmol) in methanol (45 ml). The cooling was removed and the suspension formed was left stirring at room temperature overnight. The solvent was evaporated under vacuum and the residue was dissolved in cold (0° C.) water. NaHCO$_3$ (saturated aqueous solution) was added carefully to adjust the pH to 7. The aqueous phase was thoroughly extracted three times with ethyl acetate. The organic layers were combined, dried over magnesium sulfate, filtered and concentrated. The crude product was used without further purification. Yield: 4.9 g of 4-hydroxy-1-methoxy-piperidine-4-carboxylic acid methyl ester (title compound P4.4) as light yellow oil.

$^1$H-NMR (CDCl$_3$): δ ppm 1.30-3.30 (very br m, 8H, mixture of conformers), 3.54 (s, 3H), 3.78 (s, 3H).

LC/MS (ES+): 190 (M+H)$^+$

EXAMPLE 6

Preparation of 1-Ethoxy-4-hydroxy-piperidine-4-carbonitrile (compound P4.9)

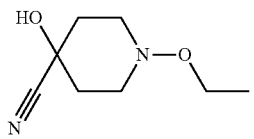

A solution of sodium bisulfite (10.7 g, 103 mmol) in 10 ml of water was cooled in an ice bath. Then, 1-ethoxy-piperidin-4-one (12.3 g, 86 mmol, prepared according to J. Org. Chem. 1961, 26, 1867-74) was added dropwise. After the addition, the mixture was stirred for another 30 min. A solution of potassium cyanide (8.4 g, 129 mmol) in 10 ml of water was added slowly, the reaction mixture was warmed up to room temperature and left stirring for 24 hours. The mixture was thoroughly extracted with ethyl acetate (4×30 ml) and the combined organic layers were washed twice with brine (2×30 ml) and dried over sodium sulfate. After filtration and concentration under vacuum, the residue was purified by column chromatography on silica gel. Yield: 13.2 g of 1-ethoxy-4-hydroxy-piperidine-4-carbonitrile (title compound P4.9) as a light yellow oil.

$^1$H-NMR (300 Mz, DMSO-d$_6$): δ ppm 1.09 (t, 3H), 1.68-2.06 (m, 4H), 2.49-3.17 (m, 4H), 3.63 (q, 2H), 6.51 (br d, 1H). ESI-MS (+): 171 (M+H)$^+$.

Compounds of the formula I from Table P1, compounds of the formula II from Table P2 and intermediates listed in Tables P3 and P4 can be prepared by analogous procedures. Either one of the following LC-MS methods was used to characterize the compounds:

Method A

MS:

ZQ Mass Spectrometer from Waters (Single quadrupole mass spectrometer); Ionisation method: Electrospray; Polarity: positive/negative ions; Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400; Mass range: 150 to 1000 or 100 to 900 Da.

LC:

HP 1100 HPLC from Agilent: solvent degasser, quaternary pump (ZCQ)/binary pump (ZDQ), heated column compartment and diode-array detector. Column: Phenomenex Gemini C18, 3 μm particle size, 110 Angström, 30×3 mm, Temp: 60° C.; DAD Wavelength range (nm): 200 to 500; Solvent gradient: A=water+0.05% v/v HCOOH, B=Acetonitrile/Methanol (4:1, v/v)+0.04% v/v HCOOH.

| Time (min) | A % | B % | Flow (ml/min) |
| --- | --- | --- | --- |
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method B
MS:

ZMD Mass Spectrometer from Waters (Single quadrupole mass spectrometer); Ionisation method: Electrospray; Polarity: positive/negative ions; Capillary (kV) 3.80, Cone (V) 30.00, Extractor (V) 3.00, Source Temperature (° C.) 150, Desolvation Temperature (° C.) 350, Cone Gas Flow (L/Hr) OFF, Desolvation Gas Flow (L/Hr) 600; Mass range: 150 to 1000 (100 to 1500 for LowMass) or 100 to 900 Da.
LC:

HP 1100 HPLC from Agilent: solvent degasser, binary pump, heated column compartment and diode-array detector. Column: Phenomenex Gemini C18, 3 μm particle size, 110 Angström, 30×3 mm, Temp: 60° C.; DAD Wavelength range (nm): 200 to 500; Solvent gradient: A=water+0.05% v/v HCOOH, B=Acetonitrile/Methanol (4:1, v/v)+0.04% v/v HCOOH.

| Time (min) | A % | B % | Flow (ml/min) |
| --- | --- | --- | --- |
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method C
MS:

Aquiety SQD Mass Spectrometer from Waters (Single quadrupole mass spectrometer); Ionisation method: Electrospray; Polarity: positive ions; Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700; Mass range: 100 to 800 Da.
LC:

Method Waters ACQUITY HPLC. Column: Waters ACQUITY HPLC HSS T3, column length: 30 mm, internal column diameter: 2.1 mm, particle size: 1.8 micron, temperature: 60° C.; DAD Wavelength range (nm): 210 to 400; HPLC gradient conditions:
Solvent A: Water/Methanol (9:1, v/v)+0.1% (v/v) formic acid and Solvent B: Acetonitrile+0.1% (v/v) formic acid.

| Time (min) | A % | B % | Flow (ml/min) |
| --- | --- | --- | --- |
| 0.00 | 100.0 | 0.0 | 1.50 |
| 0.10 | 100.0 | 0.0 | 1.50 |
| 0.20 | 100.0 | 0.0 | 0.75 |
| 1.20 | 0.0 | 100.0 | 0.75 |
| 1.40 | 0.0 | 100.0 | 0.75 |
| 1.45 | 100.0 | 0.0 | 0.75 |

Method D
MS:

ACQUITY SQD Mass Spectrometer from Waters (Single quadrupole mass spectrometer); Ionisation method: Electrospray; Polarity: positive ions; Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700 Mass range: 100 to 800 Da.
LC:

Method Waters ACQUITY HPLC. Column: Waters ACQUITY HPLC HSS T3, column length: 30 mm, internal column diameter: 2.1 mm, particle size: 1.8 micron, temperature: 60° C.; DAD Wavelength range (nm): 210 to 400; HPLC gradient conditions:

Solvent A: Water/Methanol (9:1, v/v)+0.1% (v/v) formic acid and Solvent B: Acetonitrile+0.1% (v/v) formic acid.

| Time (min) | A % | B % | Flow (ml/min) |
| --- | --- | --- | --- |
| 0.00 | 80.0 | 20.0 | 1.50 |
| 0.10 | 75.0 | 25.0 | 1.50 |
| 0.20 | 70.0 | 30.0 | 0.75 |
| 1.20 | 0.0 | 100.0 | 0.75 |
| 1.40 | 0.0 | 100.0 | 0.75 |
| 1.45 | 80.0 | 20.0 | 0.75 |

Method E
MS:

Instrument model: Shimadzu LCMS-2010EV; ESI (+)/ESI (−) scan mode; Nebulizer gas: 1.5 ml/min; CDL temperature: 250° C.; Interface Voltage: 3.5 kV; Detector Voltage: 1.5 kV.
HPLC:

Instrument model: Shimadzu LC-20AD; UV wavelength: 254 nm; Flow rate: 1 ml/min; Column temperature: 40° C.; Mobile phase: Acetonitrile/water; Column condition: Inertsil ODS-SP C18, 4.6×150 mm, 5 μm; Gradient elution:

| Time (min) | 0 | 15 | 25 |
| --- | --- | --- | --- |
| Acetonitrile % | 10 | 100 | 100 |

The characteristic values obtained for each compound were the retention time ("$R_t$", recorded in minutes) and the molecular ion as listed in Table P1, Table P2, Table P3 and Table P4.

TABLE P1
Physical data of compounds of formula I:
| Compound No. | Structures | Melting Point | MS/NMR |
|---|---|---|---|
| P1.1 | 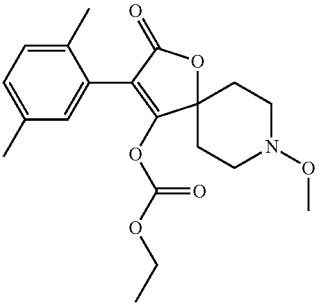 [SMILES: CCOC(=O)OC1=C(c2cc(C)ccc2C)C(=O)OC12CCN(OC)CC2] | gum | LC/MS: 376 (M + H)$^+$<br>R$_t$ = 1.87 min |
| P1.2 | 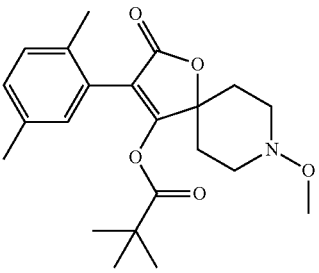 [SMILES: CON1CCC2(CC1)OC(=O)C(c1cc(C)ccc1C)=C2OC(=O)C(C)(C)C] | 135-136° C. | LC/MS: 388 (M + H)$^+$<br>R$_t$ = 2.03 min |
| P1.3 | 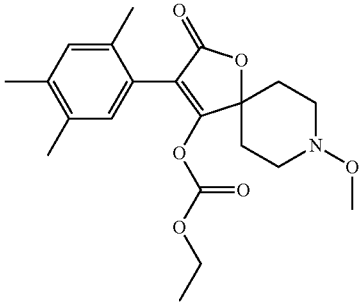 | gum | LC/MS: 390 (M + H)$^+$<br>R$_t$ = 1.94 min |
| P1.4 | 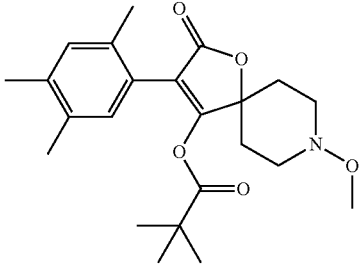 | 114-119° C. | LC/MS: 402 (M + H)$^+$<br>R$_t$ = 2.10 min |
| P1.5 | 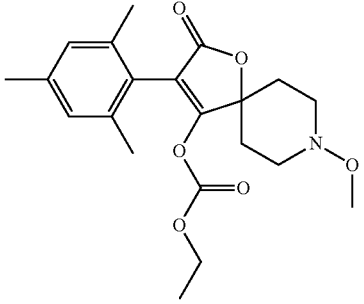 | solid | LC/MS: 390 (M + H)$^+$<br>R$_t$ = 1.92 min |

TABLE P1-continued

Physical data of compounds of formula I:

| Compound No. | Structures | Melting Point | MS/NMR |
|---|---|---|---|
| P1.6 | 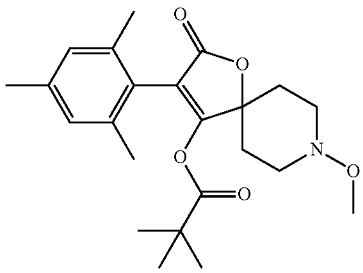 | 105-109° C. | LC/MS: 402 (M + H)+<br>R_t = 2.09 min |
| P1.7 | 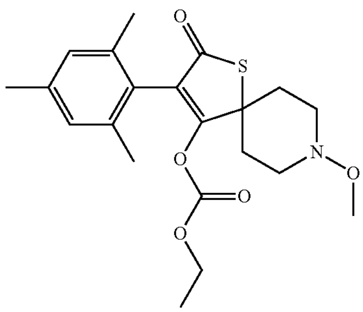 | 87-89° C. | LC/MS: 406 (M + H)+<br>R_t = 2.09 min |
| P1.8 | 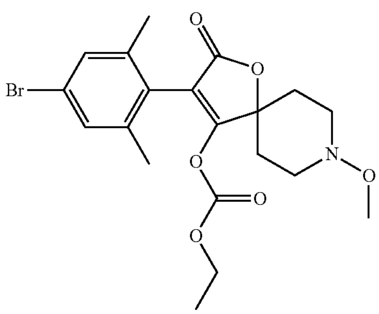 | 103-105° C. | LC/MS: 454 (M + H)<br>R_t = 1.99 min |
| P1.9 | 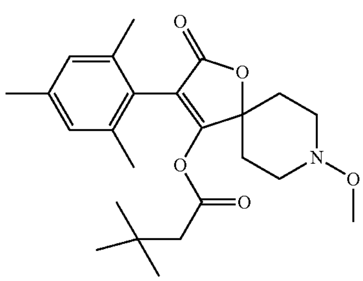 | 113-118° C. | LC/MS: 416 (M + H)<br>R_t = 2.15 min |
| P1.10 | 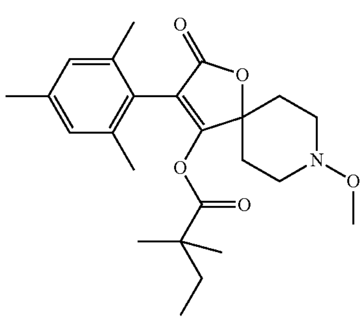 | 111-114° C. | LC/MS: 416 (M + H)<br>R_t = 2.14 min |

TABLE P1-continued

Physical data of compounds of formula I:

| Compound No. | Structures | Melting Point | MS/NMR |
|---|---|---|---|
| P1.11 | 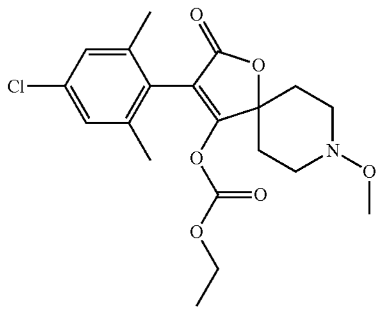 [SMILES: CCOC(=O)OC1=C(c2c(C)cc(Cl)cc2C)C(=O)OC12CCN(OC)CC2] | 128-130° C. | LC/MS: 410 (M + H)<br>$R_t$ = 1.96 min |
| P1.12 | 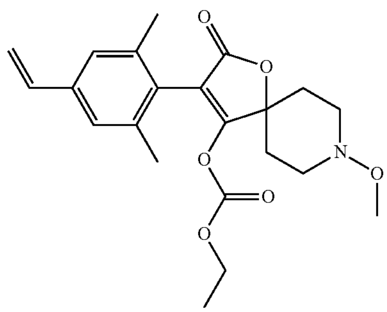 [SMILES: C=Cc1cc(C)c(C2=C(OC(=O)OCC)C3(CCN(OC)CC3)OC2=O)c(C)c1] | 127-130° C. | LC/MS: 402 (M + H)<br>$R_t$ = 1.98 min |
| P1.13 | 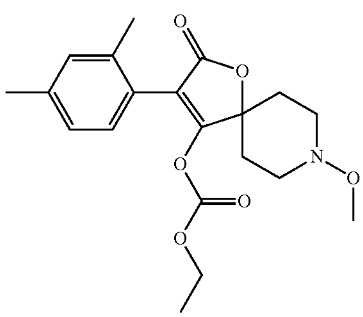 | 84-87° C. | ESI-MS: 376 (M + H)$^+$ |
| P1.14 | 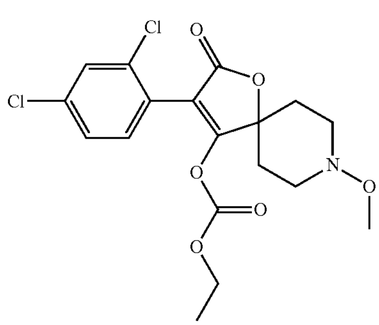 [SMILES: CCOC(=O)OC1=C(c2ccc(Cl)cc2Cl)C(=O)OC12CCN(OC)CC2] | 104-106° C. | ESI-MS: 416/418 (M + H)$^+$ |

TABLE P1-continued

Physical data of compounds of formula I:

| Compound No. | Structures | Melting Point | MS/NMR |
|---|---|---|---|
| P1.15 | 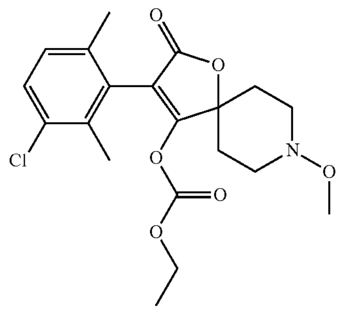 [SMILES: CCOC(=O)OC1=C(c2c(C)ccc(Cl)c2C)C(=O)OC12CCN(OC)CC2] | gum | ESI-MS: 410/412 (M + H)+ |
| P1.16 | 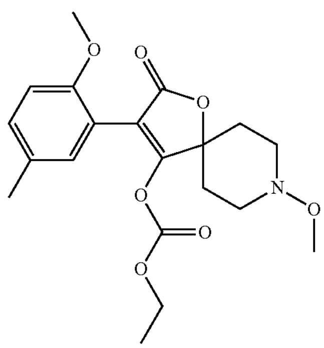 [SMILES: CCOC(=O)OC1=C(c2cc(C)ccc2OC)C(=O)OC12CCN(OC)CC2] | 81-83° C. | ESI-MS: 392 (M + H)+ |
| P1.17 | 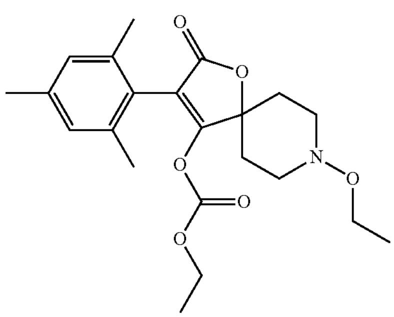 [SMILES: CCOC(=O)OC1=C(c2c(C)cc(C)cc2C)C(=O)OC12CCN(OCC)CC2] | gum | ESI-MS: 404 (M + H)+ |
| P1.18 | 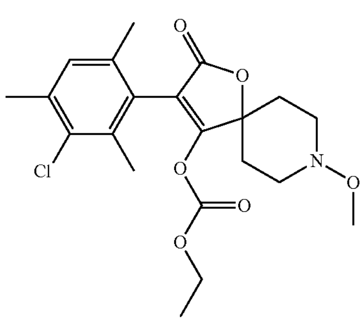 | 112-114° C. | ESI-MS: 446/448 (M + Na)+ |

TABLE P1-continued

Physical data of compounds of formula I:

| Compound No. | Structures | Melting Point | MS/NMR |
|---|---|---|---|
| P1.19 | 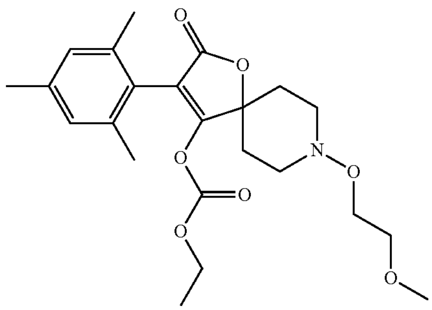 | 74-77° C. | ESI-MS: 434 (M + H)+ |
| P1.20 | 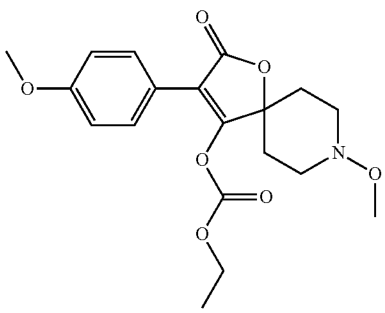 | solid | LC/MS: 378 (M + H)+<br>R$_t$ = 0.82 min |
| P1.21 | 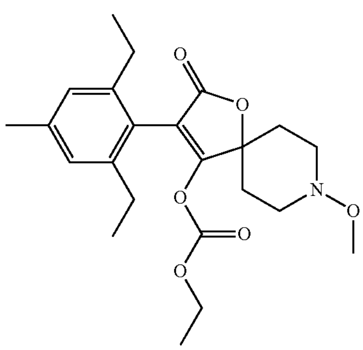 | solid | LC/MS: 418 (M + H)+<br>R$_t$ = 1.08 min |
| P1.22 | 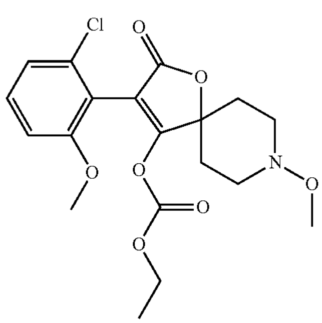 [SMILES: CCOC(=O)OC1=C(c2c(Cl)cccc2OC)C(=O)OC12CCN(OC)CC2] | solid | LC/MS: 412 (M + H)+<br>R$_t$ = 0.81 min |

TABLE P1-continued

Physical data of compounds of formula I:

| Compound No. | Structures | Melting Point | MS/NMR |
|---|---|---|---|
| P1.23 | 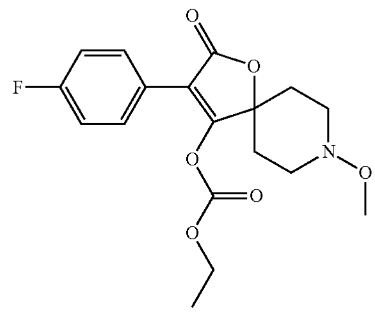 [SMILES: CCOC(=O)OC1=C(c2ccc(F)cc2)C(=O)OC12CCN(OC)CC2] | solid | LC/MS: 366 (M + H)$^+$<br>$R_t$ = 0.83 min |
| P1.24 | 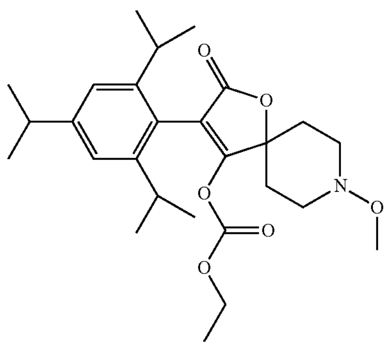 [SMILES: CCOC(=O)OC1=C(c2c(C(C)C)cc(C(C)C)cc2C(C)C)C(=O)OC12CCN(OC)CC2] | solid | LC/MS: 474 (M + H)$^+$<br>$R_t$ = 1.27 min |
| P1.25 | 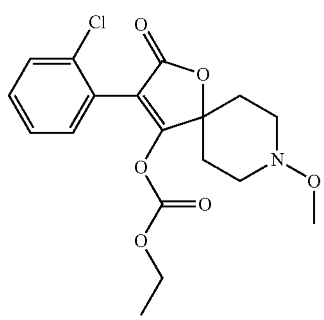 [SMILES: CCOC(=O)OC1=C(c2ccccc2Cl)C(=O)OC12CCN(OC)CC2] | solid | LC/MS: 382 (M + H)$^+$<br>$R_t$ = 0.82 min |
| P1.26 | 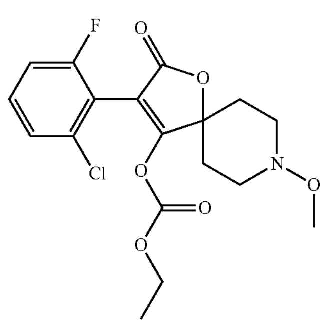 [SMILES: CCOC(=O)OC1=C(c2c(F)cccc2Cl)C(=O)OC12CCN(OC)CC2] | solid | LC/MS: 400 (M + H)$^+$<br>$R_t$ = 0.82 min |

TABLE P1-continued

Physical data of compounds of formula I:

| Compound No. | Structures | Melting Point | MS/NMR |
|---|---|---|---|
| P1.27 | 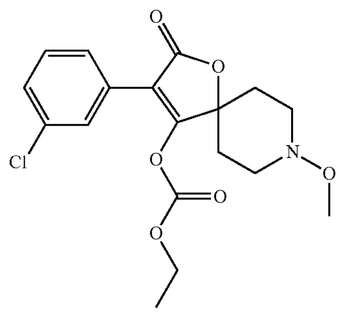 [SMILES: CCOC(=O)OC1=C(c2cccc(Cl)c2)C(=O)OC12CCN(OC)CC2] | solid | LC/MS: 382 (M + H)+<br>R$_t$ = 0.92 min |
| P1.28 | 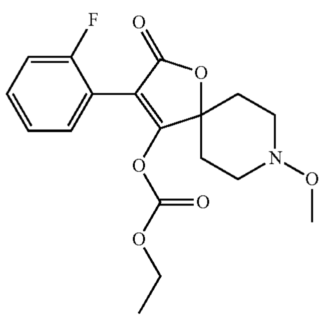 [SMILES: CCOC(=O)OC1=C(c2ccccc2F)C(=O)OC12CCN(OC)CC2] | solid | LC/MS: 366 (M + H)+<br>R$_t$ = 0.78 min |
| P1.29 | 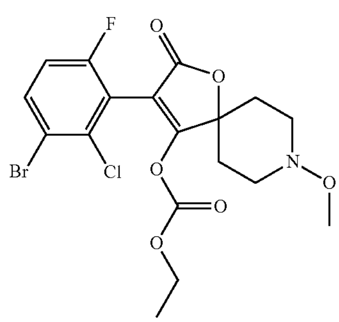 [SMILES: CCOC(=O)OC1=C(c2c(F)ccc(Br)c2Cl)C(=O)OC12CCN(OC)CC2] | gum | LC/MS: 478 (M + H)+<br>R$_t$ = 0.93 min |
| P1.30 | 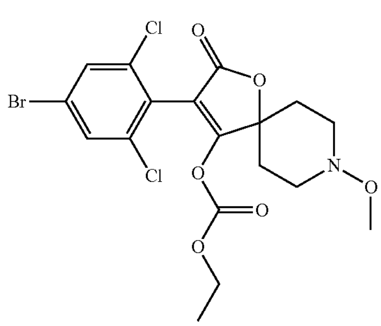 | 122-125° C. | LC/MS: 496 (M + H)+<br>R$_t$ = 1.99 min |

TABLE P1-continued

Physical data of compounds of formula I:

| Compound No. | Structures | Melting Point | MS/NMR |
|---|---|---|---|
| P1.31 | 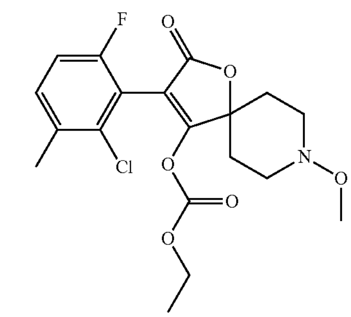 [SMILES: CCOC(=O)OC1=C(c2c(F)ccc(C)c2Cl)C(=O)OC12CCN(OC)CC2] | gum | LC/MS: 414 (M + H)+ <br> $R_t$ = 1.86 min |
| P1.32 | 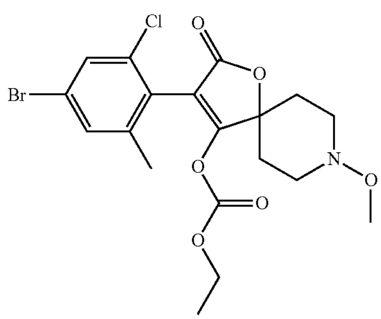 | gum | LC/MS: 475 (M + H)+ <br> $R_t$ = 2.01 min |
| P1.33 | 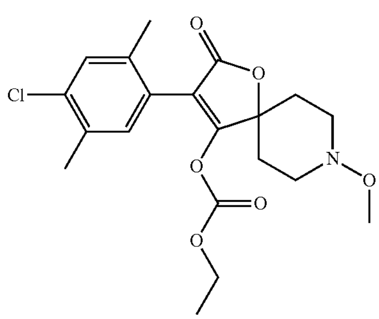 [SMILES: CCOC(=O)OC1=C(c2cc(C)c(Cl)cc2C)C(=O)OC12CCN(OC)CC2] | gum | LC/MS: 410 (M + H)+ <br> $R_t$ = 2.01 min |
| P1.34 | 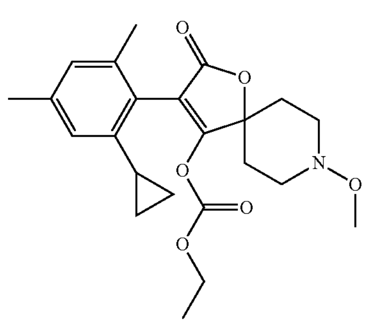 | gum | LC/MS: 416 (M + H)+ <br> $R_t$ = 2.02 min |

TABLE P1-continued
Physical data of compounds of formula I:
| Compound No. | Structures | Melting Point | MS/NMR |
|---|---|---|---|
| P1.35 | 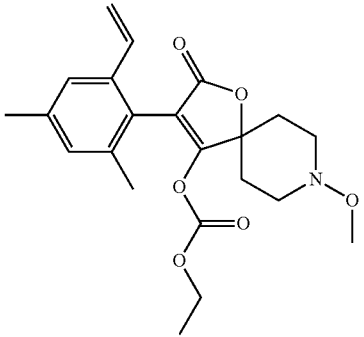 | gum | LC/MS: 416 (M + H)$^+$<br>$R_t$ = 1.97 min |
| P1.36 | 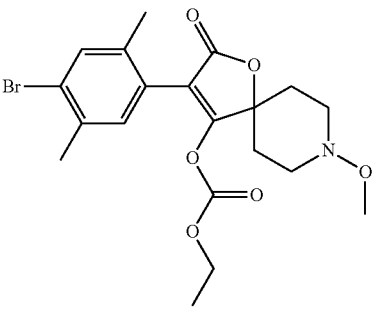 | gum | LC/MS: 455 (M + H)$^+$<br>$R_t$ = 2.03 min |
| P1.37 | 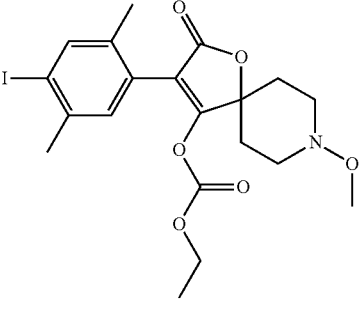 [SMILES: CCOC(=O)OC1=C(c2cc(C)c(I)cc2C)C(=O)OC12CCN(OC)CC2] | gum | LC/MS: 502 (M + H)$^+$<br>$R_t$ = 2.01 min |
| P1.38 | 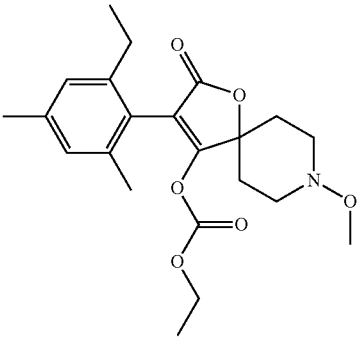 | gum | LC/MS: 404 (M + H)$^+$<br>$R_t$ = 2.01 min |

TABLE P1-continued

Physical data of compounds of formula I:

| Compound No. | Structures | Melting Point | MS/NMR |
|---|---|---|---|
| P1.39 | 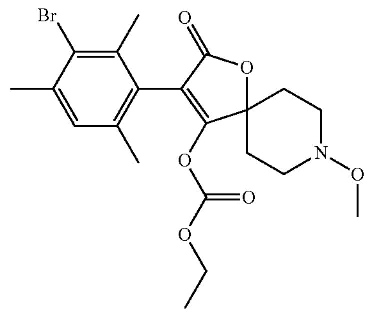 | 52-54° C. | ESI-MS: 468/470 (M + H)+, 490/492 (M + Na)+, 522/524 (M + Na + CH₃OH)+ |
| P1.40 | 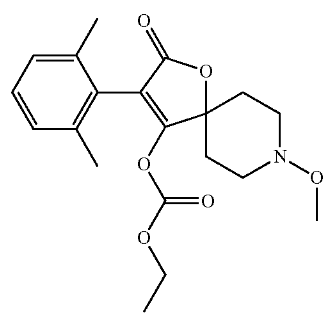 [SMILES: CCOC(=O)OC1=C(c2c(C)cccc2C)C(=O)OC12CCN(OC)CC2] | 93-94° C. | ESI-MS: 376 (M + H)+, 398 (M + Na)+, 430 (M + Na + CH₃OH)+ |
| P1.41 | 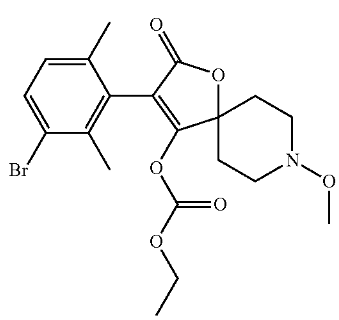 | gum | ESI-MS: 476/478 (M + Na)+, 508/510 (M + Na + CH₃OH)+ |
| P1.42 | 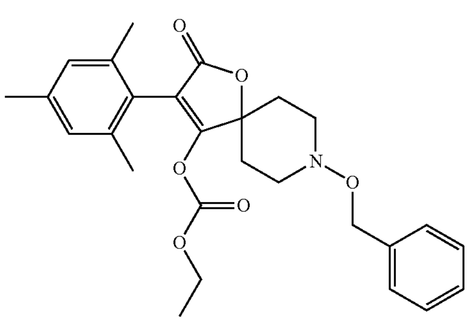 [SMILES: CCOC(=O)OC1=C(c2c(C)cc(C)cc2C)C(=O)OC12CCN(OCc1ccccc1)CC2] | gum | ESI-MS: 466 (M + H)+, 488 (M + Na)+ |

TABLE P1-continued

Physical data of compounds of formula I:

| Compound No. | Structures | Melting Point | MS/NMR |
|---|---|---|---|
| P1.43 | 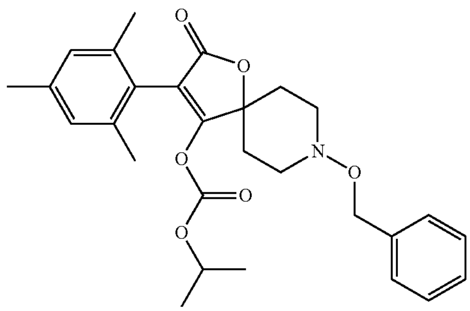 [SMILES: Cc1cc(C)c(C2=C(OC(=O)OC(C)C)C3(CCN(OCc4ccccc4)CC3)OC2=O)c(C)c1] | gum | ESI-MS: 480 (M + H)⁺, 502 (M + Na)⁺ |
| P1.44 | 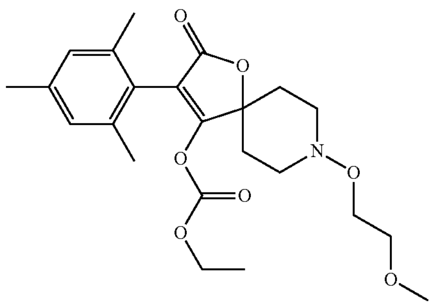 | 74-77° C. | ESI-MS: 434 (M + H)⁺, 456 (M + Na)⁺ |
| P1.45 | 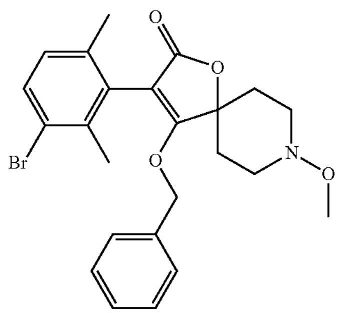 [SMILES: CON1CCC2(CC1)OC(=O)C(c1c(C)ccc(Br)c1C)=C2OCc1ccccc1] | solid | ESI-MS: 472/474 (M + H)⁺, 496/498 (M + Na)⁺, 526/528 (M + Na + CH₃OH)⁺ |
| P1.46 | 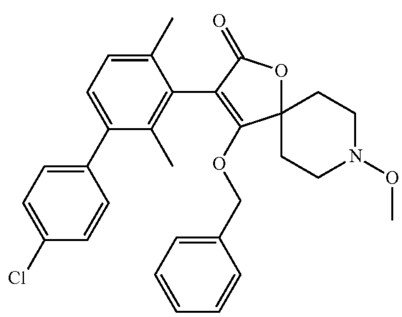 [SMILES: CON1CCC2(CC1)OC(=O)C(c1c(C)ccc(-c3ccc(Cl)cc3)c1C)=C2OCc1ccccc1] | solid | ESI-MS: 504 (M + H)⁺, 526 (M + Na)⁺, 558 (M + Na + CH₃OH)⁺ |
| P1.47 | 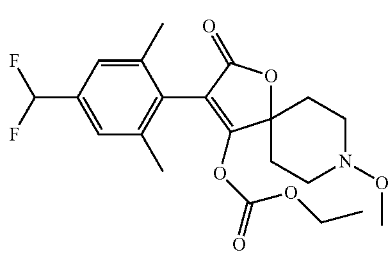 [SMILES: CCOC(=O)OC1=C(c2c(C)cc(C(F)F)cc2C)C(=O)OC12CCN(OC)CC2] | gum | LC/MS: 426 (M + H)⁺ |

TABLE P1-continued

Physical data of compounds of formula I:

| Compound No. | Structures | Melting Point | MS/NMR |
|---|---|---|---|
| P1.48 | 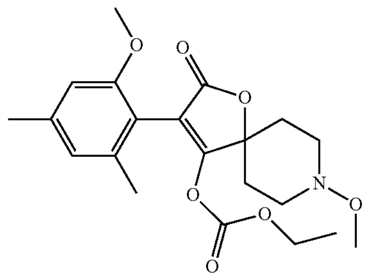 | gum | LC/MS: 406 (M + H)+ |

TABLE P2

Physical data of compounds of formula II:

| Compound No. | Structures | Melting Point | MS/NMR |
|---|---|---|---|
| P2.1 | 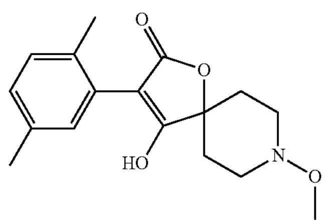 [SMILES: CON1CCC2(CC1)OC(=O)C(c1cc(C)ccc1C)=C2O] | 205-208° C. | LC/MS: 304 (M + H)+<br>$R_t$ = 1.54 min |
| P2.2 | 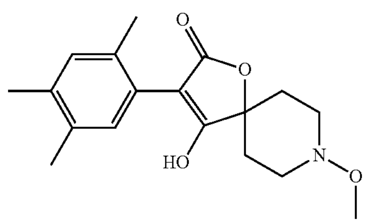 | 199-204° C. | LC/MS: 318 (M + H)+<br>$R_t$ = 1.65 min |
| P2.3 | 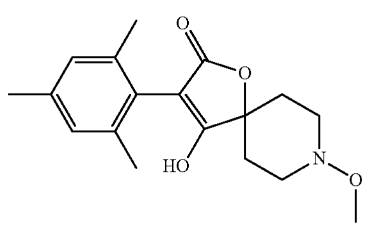 | 197-201° C. | LC/MS: 318 (M + H)+<br>$R_t$ = 1.61 min |
| P2.4 | 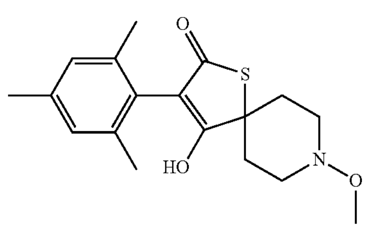 | 67-71° C. | LC/MS: 334 (M + H)+<br>$R_t$ = 1.80 min |

TABLE P2-continued

Physical data of compounds of formula II:

| Compound No. | Structures | Melting Point | MS/NMR |
|---|---|---|---|
| P2.5 | 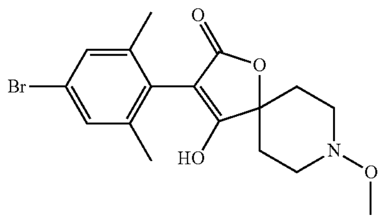 | 208-210° C. | LC/MS: 383 (M + H)+ R$_t$ = 1.75 min |
| P2.6 | 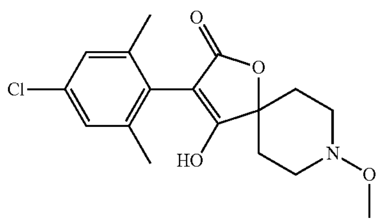 [SMILES: CON1CCC2(CC1)OC(=O)C(c1c(C)cc(Cl)cc1C)=C2O] | 165-168° C. | LC/MS: 338 (M + H)+ R$_t$ = 1.66 min |
| P2.7 | 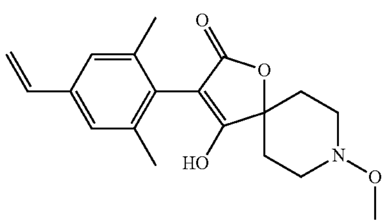 [SMILES: C=Cc1cc(C)c(C2=C(O)C3(CCN(OC)CC3)OC2=O)c(C)c1] | 210-212° C. | LC/MS: 330 (M + H)+ R$_t$ = 1.70 min |
| P2.8 | 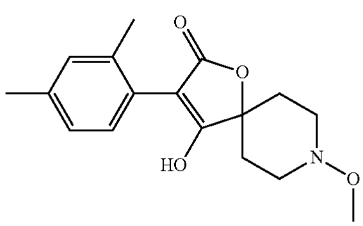 | 204-206° C. | ESI-MS: 304 (M + H)+ |
| P2.9 | 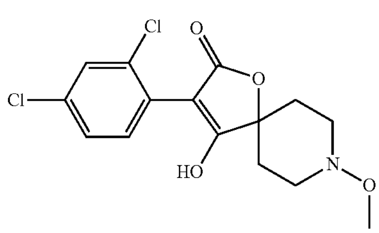 [SMILES: CON1CCC2(CC1)OC(=O)C(c1ccc(Cl)cc1Cl)=C2O] | 245-247° C. | ESI-MS: 342/344 (M − H)− |
| P2.10 | 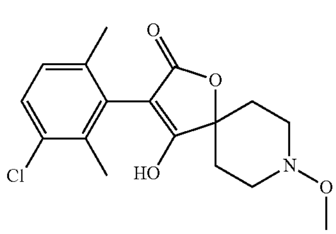 [SMILES: CON1CCC2(CC1)OC(=O)C(c1c(C)ccc(Cl)c1C)=C2O] | 117-120° C. | ESI-MS: 336/338 (M − H)− |

TABLE P2-continued

Physical data of compounds of formula II:

| Compound No. | Structures | Melting Point | MS/NMR |
|---|---|---|---|
| P2.11 | 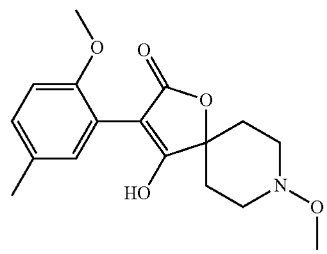 [SMILES: COc1ccc(C)cc1C1=C(O)C2(CCN(OC)CC2)OC1=O] | 159-161° C. | ESI-MS: 320 (M + H)+ |
| P2.12 | 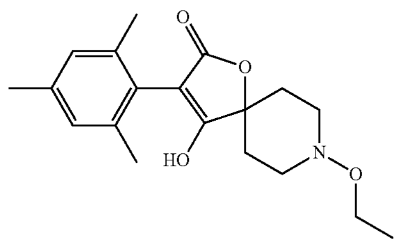 [SMILES: CCON1CCC2(CC1)OC(=O)C(c1c(C)cc(C)cc1C)=C2O] | 236-239° C. | ESI-MS: 332 (M + H)+ |
| P2.13 | 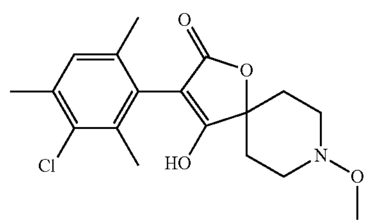 | 204-206° C. | ESI-MS: 352/354 (M + H)+ |
| P2.14 | 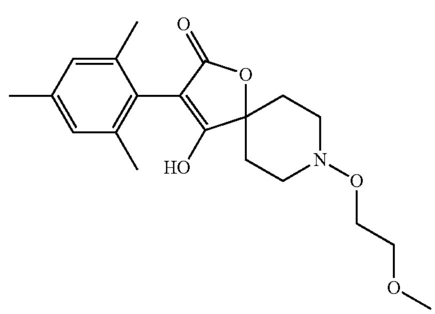 | 76-78° C. | ESI-MS: 362 (M + H)+ |
| P2.15 | 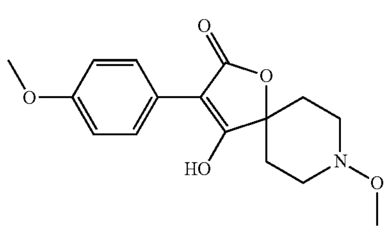 | solid | LC/MS: 306 (M + H)+<br>$R_t$ = 0.79 min |
| P2.16 | 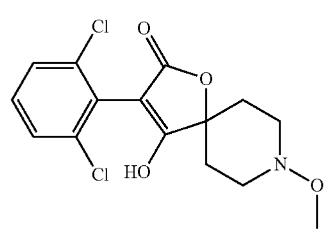 [SMILES: CON1CCC2(CC1)OC(=O)C(c1c(Cl)cccc1Cl)=C2O] | solid | LC/MS: 344 (M + H)+<br>$R_t$ = 0.78 min |

TABLE P2-continued

Physical data of compounds of formula II:

| Compound No. | Structures | Melting Point | MS/NMR |
|---|---|---|---|
| P2.17 | 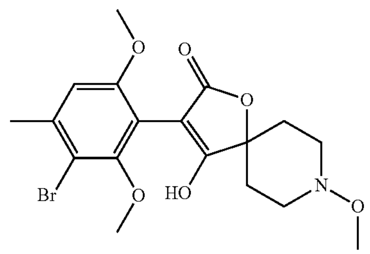 | solid | LC/MS: 428 (M + H)+ $R_t$ = 0.91 min |
| P2.18 | 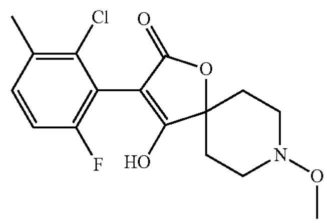 [SMILES: CON1CCC2(CC1)OC(=O)C(c1c(F)ccc(C)c1Cl)=C2O] | 113-114° C. | LC/MS: 342 (M + H)+ $R_t$ = 0.82 min |
| P2.19 | 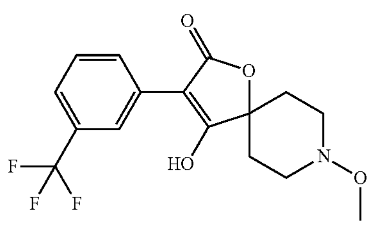 [SMILES: CON1CCC2(CC1)OC(=O)C(c1cccc(C(F)(F)F)c1)=C2O] | solid | LC/MS: 344 (M + H)+ $R_t$ = 0.827 min |
| P2.20 | 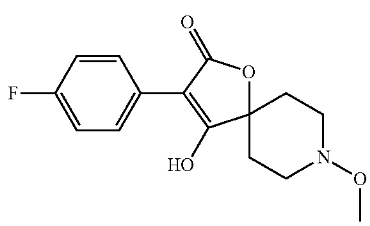 [SMILES: CON1CCC2(CC1)OC(=O)C(c1ccc(F)cc1)=C2O] | solid | LC/MS: 294 (M + H)+ $R_t$ = 0.79 min |
| P2.21 | 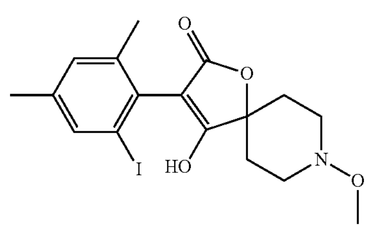 | solid | LC/MS: 430 (M + H)+ $R_t$ = 0.94 min |
| P2.22 | 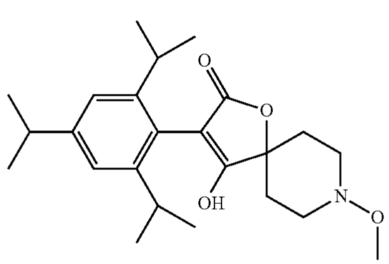 | solid | LC/MS: 430 (M + H)+ $R_t$ = 1.19 min |

TABLE P2-continued

Physical data of compounds of formula II:

| Compound No. | Structures | Melting Point | MS/NMR |
|---|---|---|---|
| P2.23 | (2-chlorophenyl substituted spiro lactone with N-OMe piperidine) | solid | LC/MS: 310 (M + H)+<br>$R_t$ = 0.76 min |
| P2.24 | (2-fluoro-6-chlorophenyl substituted spiro lactone with N-OMe piperidine) | solid | LC/MS: 328 (M + H)+<br>$R_t$ = 0.72 min |
| P2.25 | (3-chlorophenyl substituted spiro lactone with N-OMe piperidine) | solid | LC/MS: 310 (M + H)+<br>$R_t$ = 0.83 min |
| P2.26 | (4-bromophenyl substituted spiro lactone with N-OMe piperidine) | solid | LC/MS: 354 (M + H)+<br>$R_t$ = 0.85 min |
| P2.27 | (2-fluorophenyl substituted spiro lactone with N-OMe piperidine) | solid | LC/MS: 294 (M + H)+<br>$R_t$ = 0.71 min |
| P2.28 | (2-fluoro-3-bromo-6-chlorophenyl substituted spiro lactone with N-OMe piperidine) | solid | LC/MS: 406 (M + H)+<br>$R_t$ = 0.80 min |

TABLE P2-continued

Physical data of compounds of formula II:

| Compound No. | Structures | Melting Point | MS/NMR |
|---|---|---|---|
| P2.29 | 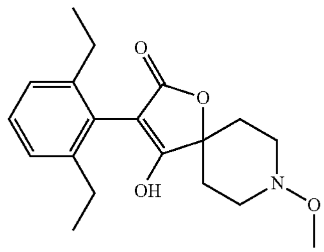 [SMILES: CCc1cccc(CC)c1C1=C(O)C2(CCN(OC)CC2)OC1=O] | solid | LC/MS: 332 (M + H)+<br>R$_t$ = 0.98 min |
| P2.30 | 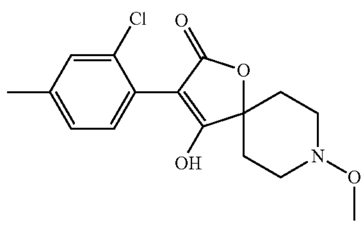 | solid | LC/MS: 324 (M + H)+<br>R$_t$ = 0.85 min |
| P2.31 | 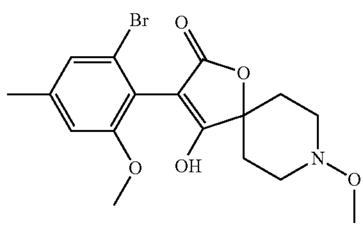 | solid | LC/MS: 397 (M + H)+<br>R$_t$ = 0.87 min |
| P2.32 | 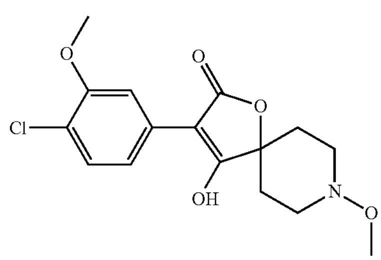 [SMILES: COc1cc(C2=C(O)C3(CCN(OC)CC3)OC2=O)ccc1Cl] | solid | LC/MS: 340 (M + H)+<br>R$_t$ = 0.81 min |
| P2.33 | 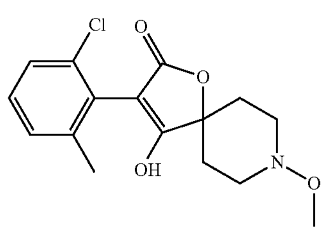 | solid | LC/MS: 324 (M + H)+<br>R$_t$ = 0.82 min |
| P2.34 | 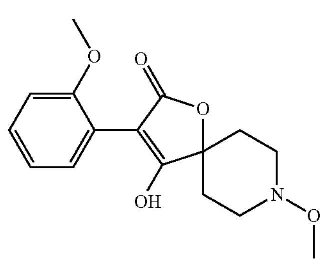 [SMILES: COc1ccccc1C1=C(O)C2(CCN(OC)CC2)OC1=O] | solid | LC/MS: 306 (M + H)+<br>R$_t$ = 0.81 min |

TABLE P2-continued
Physical data of compounds of formula II:
| Compound No. | Structures | Melting Point | MS/NMR |
|---|---|---|---|
| P2.35 | 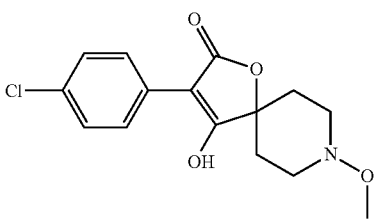 [SMILES: CON1CCC2(CC1)OC(=O)C(c1ccc(Cl)cc1)=C2O] | solid | LC/MS: 310 (M + H)+<br>R_t = 0.84 min |
| P2.36 | 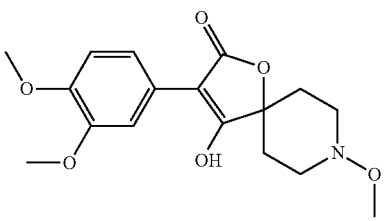 | solid | LC/MS: 336 (M + H)+<br>R_t = 0.73 min |
| P2.37 | 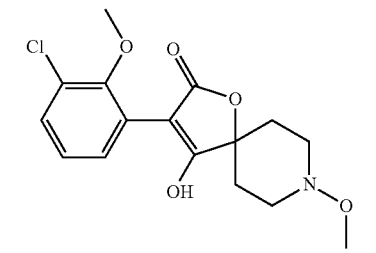 [SMILES: COc1c(Cl)cccc1C1=C(O)C2(CCN(OC)CC2)OC1=O] | solid | LC/MS: 340 (M + H)+<br>R_t = 0.89 min |
| P2.38 | 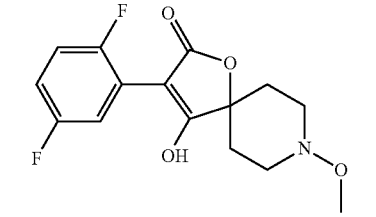 [SMILES: CON1CCC2(CC1)OC(=O)C(c1cc(F)ccc1F)=C2O] | solid | LC/MS: 312 (M + H)+<br>R_t = 0.70 min |
| P2.39 | 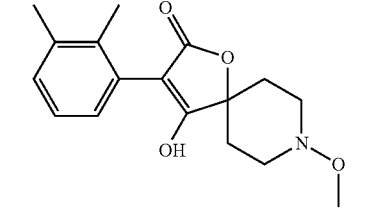 [SMILES: CON1CCC2(CC1)OC(=O)C(c1cccc(C)c1C)=C2O] | solid | LC/MS: 304 (M + H)+<br>R_t = 0.86 min |
| P2.40 | 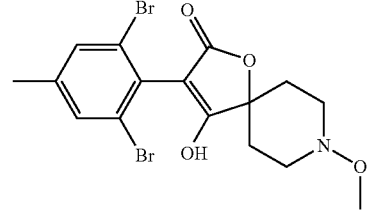 | solid | LC/MS: 446 (M + H)+<br>R_t = 0.89 min |

TABLE P2-continued

Physical data of compounds of formula II:

| Compound No. | Structures | Melting Point | MS/NMR |
|---|---|---|---|
| P2.41 | 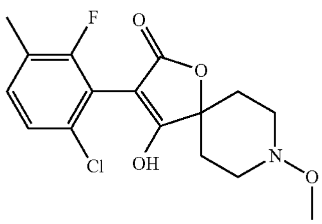 [SMILES: CON1CCC2(CC1)OC(=O)C(c1c(Cl)ccc(C)c1F)=C2O] | solid | LC/MS: 342 (M + H)$^+$<br>$R_t$ = 0.81 min |
| P2.42 | 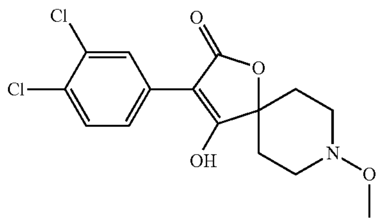 [SMILES: CON1CCC2(CC1)OC(=O)C(c1ccc(Cl)c(Cl)c1)=C2O] | solid | LC/MS: 344 (M + H)$^+$<br>$R_t$ = 0.89 min |
| P2.43 | 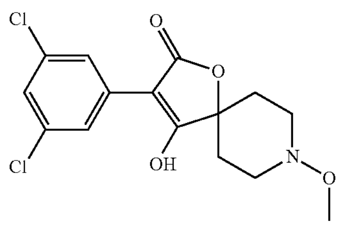 [SMILES: CON1CCC2(CC1)OC(=O)C(c1cc(Cl)cc(Cl)c1)=C2O] | solid | LC/MS: 344 (M + H)$^+$<br>$R_t$ = 0.89 min |
| P2.44 | 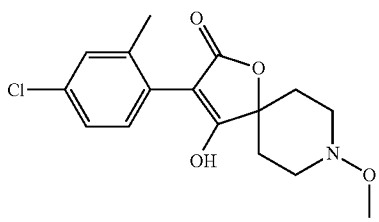 [SMILES: CON1CCC2(CC1)OC(=O)C(c1ccc(Cl)cc1C)=C2O] | solid | LC/MS: 324 (M + H)$^+$<br>$R_t$ = 0.88 min |
| P2.45 | 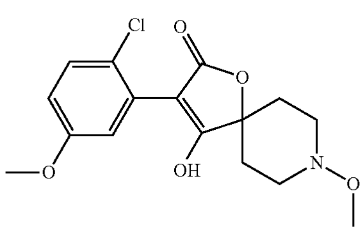 | solid | LC/MS: 340 (M + H)$^+$<br>$R_t$ = 0.88 min |
| P2.46 | 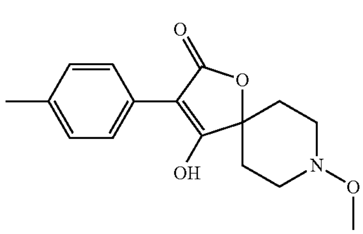 | solid | LC/MS: 290 (M + H)$^+$<br>$R_t$ = 0.85 min |

TABLE P2-continued

Physical data of compounds of formula II:

| Compound No. | Structures | Melting Point | MS/NMR |
|---|---|---|---|
| P2.47 | 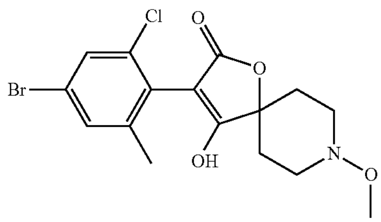 [SMILES: CON1CCC2(CC1)OC(=O)C(c1c(C)cc(Br)cc1Cl)=C2O] | 150-151° C. | LC/MS: 403 (M + H)$^+$<br>$R_t$ = 1.90 min |
| P2.48 | 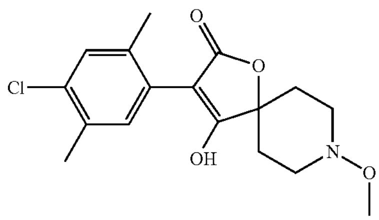 [SMILES: CON1CCC2(CC1)OC(=O)C(c1cc(C)c(Cl)cc1C)=C2O] | 193-196° C. | LC/MS: 338 (M + H)$^+$<br>$R_t$ = 1.84 min |
| P2.49 | 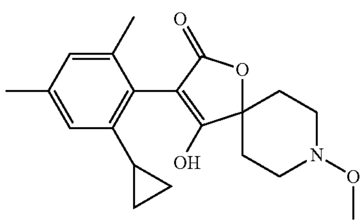 | gum | LC/MS: 344 (M + H)$^+$<br>$R_t$ = 1.70 min |
| P2.50 | 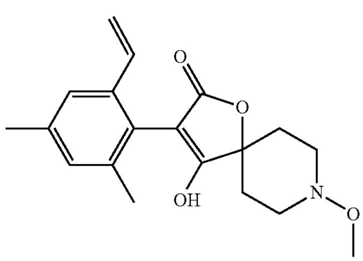 | 107-109° C. | LC/MS: 330 (M + H)$^+$<br>$R_t$ = 1.66 min |
| P2.51 | 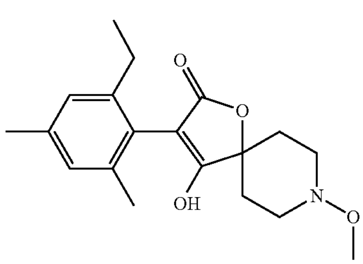 | 210-211° C. | LC/MS: 332 (M + H)$^+$<br>$R_t$ = 1.70 min |
| P2.52 | 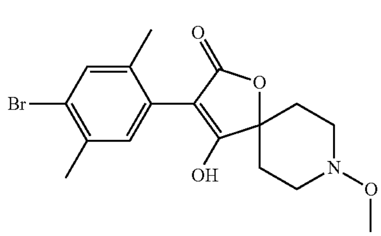 | 198-200° C. | LC/MS: 383 (M + H)$^+$<br>$R_t$ = 1.76 min |

TABLE P2-continued

Physical data of compounds of formula II:

| Compound No. | Structures | Melting Point | MS/NMR |
|---|---|---|---|
| P2.53 | 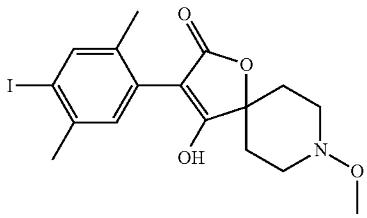 [SMILES: CON1CCC2(CC1)OC(=O)C(c1cc(C)c(I)cc1C)=C2O] | 222-223° C. | LC/MS: 430 (M + H)+<br>R$_t$ = 1.84 min |
| P2.54 | 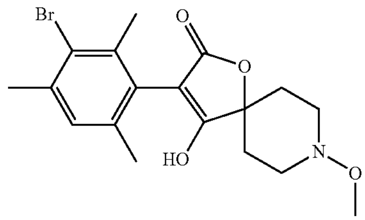 | 185-186° C. | ESI-MS: 450/452<br>(M + Na + CH$_3$OH)+ |
| P2.55 | 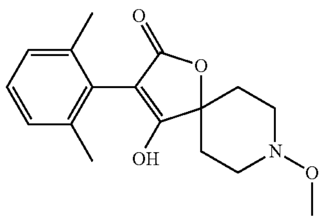 [SMILES: CON1CCC2(CC1)OC(=O)C(c1c(C)cccc1C)=C2O] | 96-99° C. | ESI-MS: 304 (M + H)+,<br>326 (M + Na)+, 358<br>(M + Na + CH$_3$OH)+ |
| P2.56 | 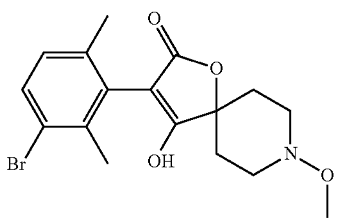 [SMILES: CON1CCC2(CC1)OC(=O)C(c1c(C)ccc(Br)c1C)=C2O] | 121-123° C. | ESI-MS(−): 380/382<br>(M − H)+ |
| P2.57 | 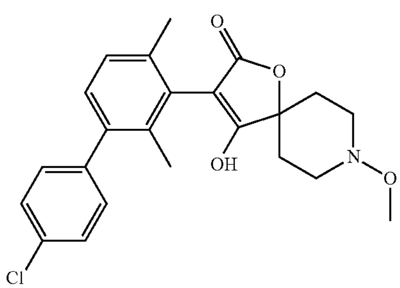 [SMILES: CON1CCC2(CC1)OC(=O)C(c1c(C)ccc(-c3ccc(Cl)cc3)c1C)=C2O] | 230-232° C. | ESI-MS(−): 412 (M − H)+ |
| P2.58 | 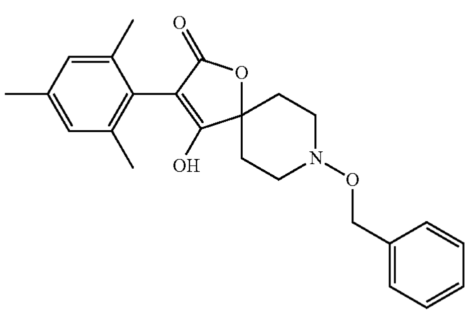 [SMILES: Cc1cc(C)c(C2=C(O)C3(CCN(OCc4ccccc4)CC3)OC2=O)c(C)c1] | 166-168° C. | ESI-MS: 394 (M + H)+,<br>416 (M + Na)+ |

TABLE P2-continued

Physical data of compounds of formula II:

| Compound No. | Structures | Melting Point | MS/NMR |
|---|---|---|---|
| P2.59 | 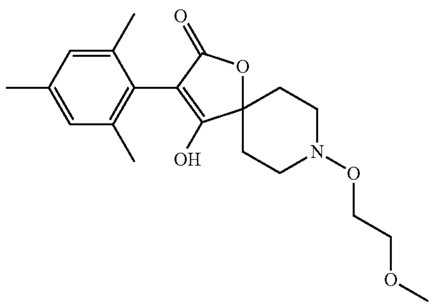 | 76-78° C. | ESI-MS: 362 (M + H)+, 384 (M + Na)+ |
| P2.60 | 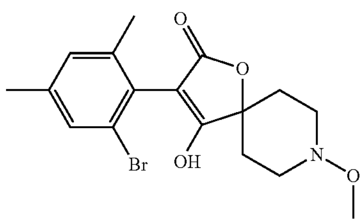 | 130-133° C. | ESI-MS: 380/382 (M + H)+ |
| P2.61 | 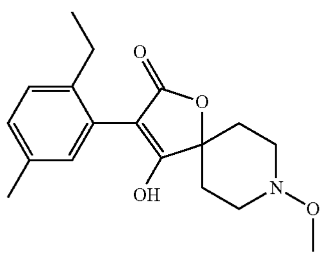 [SMILES: CCc1ccc(C)cc1C1=C(O)C2(CCN(OC)CC2)OC1=O] | 166-168° C. | ESI-MS: 318 (M + H)+ |
| P2.62 | 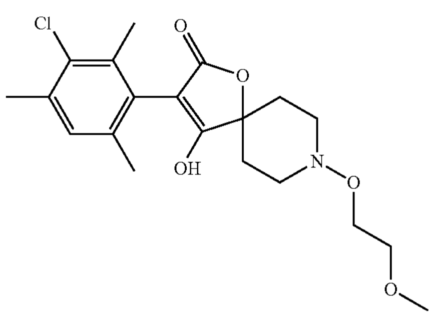 | 159-160° C. | ESI-MS: 418 (M + Na)+ |
| P2.63 | 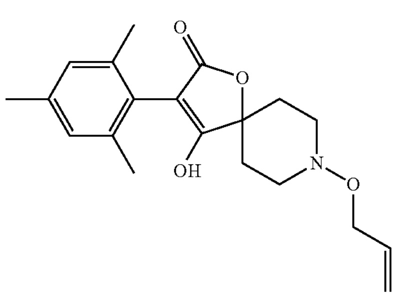 [SMILES: C=CCON1CCC2(CC1)OC(=O)C(c1c(C)cc(C)cc1C)=C2O] | solid | ESI-MS: 344 (M + H)+ |

TABLE P2-continued

Physical data of compounds of formula II:

| Compound No. | Structures | Melting Point | MS/NMR |
|---|---|---|---|
| P2.64 | 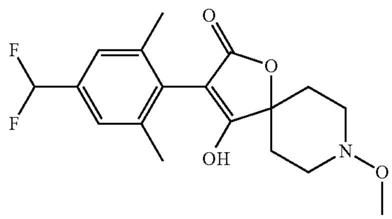 [SMILES: CON1CCC2(CC1)OC(=O)C(c1c(C)cc(C(F)F)cc1C)=C2O] | solid | ¹H-NMR (MeOD, selected peaks): 2.25 (s, 6H), 3.58 (s, 3H), 6.71 (brt, 1H), 7.30 (s, 2H) |
| P2.65 | 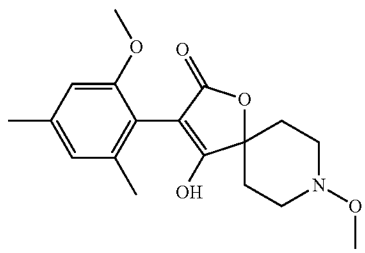 | 195-198° C. | LC/MS: 334 (M + H)$^+$ $R_t$ = 1.50 min |

Intermediates of the formula IV or XI from Table P3 can be prepared by analogous procedures.

TABLE P3

Physical data of intermediates of formula IV or XI:

| Compound No. | Structures | Melting Point | MS/NMR |
|---|---|---|---|
| P3.1 | 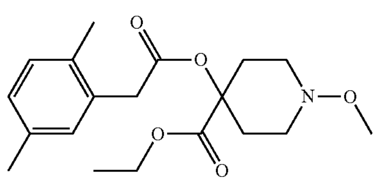 [SMILES: CCOC(=O)C1(OC(=O)Cc2cc(C)ccc2C)CCN(OC)CC1] | oil | LC/MS: 350 (M + H)$^+$ $R_t$ = 1.95 min |
| P3.2 | 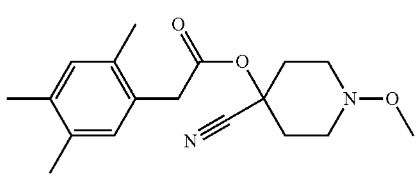 | gum | LC/MS: 317 (M + H)$^+$ $R_t$ = 1.99 min |
| P3.3 | 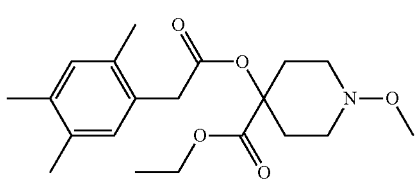 | | LC/MS: 304 (M + H)$^+$ $R_t$ = 1.63 min |
| P3.4 | 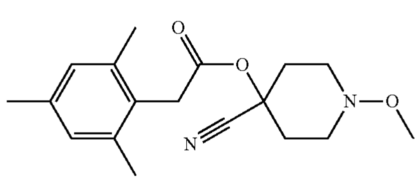 | 75-78° C. | LC/MS: 317 (M + H)$^+$ $R_t$ = 1.94 min |

TABLE P3-continued

Physical data of intermediates of formula IV or XI:

| Compound No. | Structures | Melting Point | MS/NMR |
|---|---|---|---|
| P3.5 | 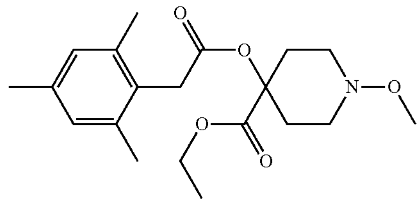 | oil | LC/MS: 364 (M + H)+<br>R$_t$ = 2.03 min |
| P3.6 | 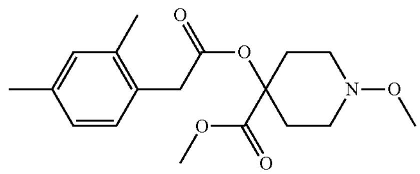 | solid | $^1$H-NMR (CDCl$_3$): 1.58-2.41 (m, 4H), 2.29 (s, 3H), 2.30 (s, 3H), 2.50-3.19 (m, 4H), 3.53 (s, 3H), 3.65 (s, 2H), 3.69 (s, 3H), 6.96-7.11 (m, 3H).<br>ESI-MS: 336 (M + H)+ |
| P3.7 | 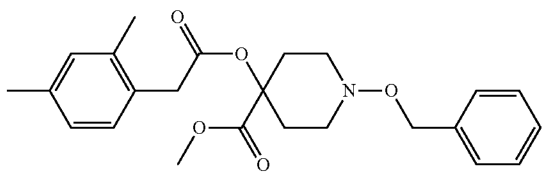 | oil | $^1$H-NMR (CDCl$_3$): 1.89-2.55 (m, 4H), 2.25 (s, 3H), 2.28 (s, 6H), 2.59-3.14 (m, 4H), 3.67 (s, 3H), 3.69 (s, 2H), 4.69 (s, 2H), 6.86 (s, 2H), 7.35 (m, 5H).<br>ESI-MS: 426 (M + H)+ |
| P3.8 | 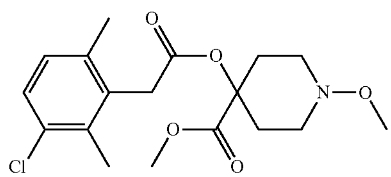 [SMILES: COC(=O)C1(OC(=O)Cc2c(C)ccc(Cl)c2C)CCN(OC)CC1] | oil | $^1$H-NMR (CDCl$_3$): 1.80-2.53 (m, 4H), 2.34 (s, 3H), 2.40 (s, 3H), 2.85-3.24 (m, 4H), 3.54 (s, 3H), 3.70 (s, 3H), 3.79 (s, 2H), 6.99 (d, 1H), 7.22 (d, 1H).<br>ESI-MS: 370 (M + H)+ |
| P3.9 | 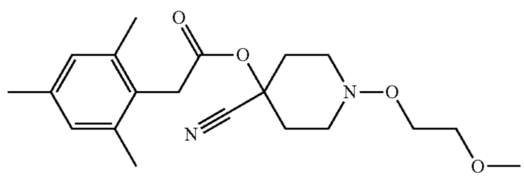 | oil | $^1$H-NMR (CDCl$_3$): 1.91-2.55 (m, 4H), 2.25 (s, 3H), 2.27 (s, 6H), 2.75-3.16 (m, 4H), 3.36 (s, 3H), 3.52 (t, 2H), 3.70 (s, 2H), 3.79 (t, 2H), 6.85 (s, 2H).<br>ESI-MS: 361 (M + H)+ |
| P3.10 | 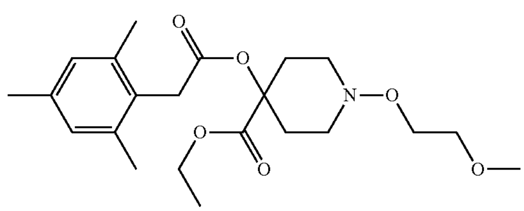 | oil | $^1$H-NMR (CDCl$_3$): 1.17 (t, 3H), 2.07-2.17 (m, 4H), 2.24 (s, 3H), 2.28 (s, 6H), 2.40-3.21 (m, 4H), 3.37 (s, 3H), 3.52 (t, 2H), 3.68 (s, 2H), 3.84 (t, 2H), 4.10 (q, 2H), 6.84 (s, 2H).<br>ESI-MS: 408 (M + H)+ |
| P3.11 | 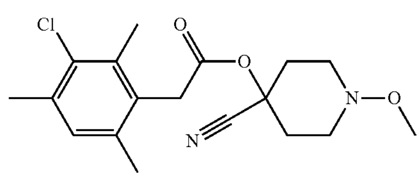 | oil | $^1$H-NMR (DMSO-d$_6$): 1.89-2.40 (m, 4H), 2.23 (s, 3H), 2.28 (s, 3H), 2.31 (s, 3H), 2.55-3.25 (m, 4H), 3.41 (s, 3H), 3.89 (s, 2H), 7.07 (s, 1H).<br>ESI-MS: 351 (M + H)+ |
| P3.12 | 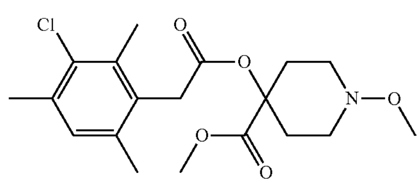 | oil | $^1$H-NMR (DMSO-d$_6$): 1.61-2.08 (m, 4H), 2.22 (s, 3H), 2.28 (s, 3H), 2.31 (s, 3H), 2.31-3.15 (m, 4H), 3.40 (s, 3H), 3.60 (s, 3H), 3.82 (s, 2H), 7.06 (s, 1H).<br>ESI-MS: 384 (M + H)+ |

TABLE P3-continued

Physical data of intermediates of formula IV or XI:

| Compound No. | Structures | Melting Point | MS/NMR |
|---|---|---|---|
| P3.13 | 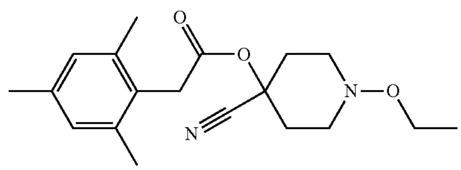 [SMILES: CCON1CCC(C#N)(OC(=O)Cc2c(C)cc(C)cc2C)CC1] | oil | $^1$H-NMR (CDCl$_3$): 1.17 (t, 3H), 1.81-2.62 (m, 4H), 2.28 (s, 3H), 2.31 (s, 6H), 2.78-3.11 (m, 4H), 3.67 (q, 2H), 3.75 (s, 2H), 6.89 (s, 2H). ESI-MS: 331 (M + H)$^+$ |
| P3.14 | 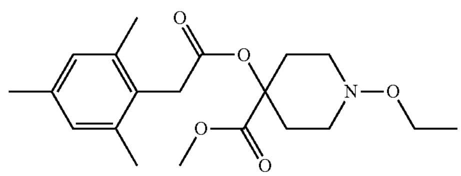 | oil | $^1$H-NMR (DMSO-d$_6$): 1.14 (t, 3H), 2.01-2.61 (m, 4H), 2.26 (s, 3H), 2.31 (s, 6H), 2.78-3.18 (m, 4H), 3.71 (s, 2H), 3.73 (s, 3H), 4.14 (q, 2H), 6.87 (s, 2H). ESI-MS: 378 (M + H)$^+$ |
| P3.15 | 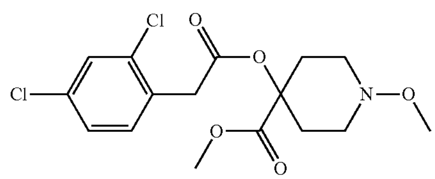 [SMILES: COC(=O)C1(OC(=O)Cc2ccc(Cl)cc2Cl)CCN(OC)CC1] | solid | $^1$H-NMR (DMSO-d$_6$): 1.80-2.41 (m, 4H), 2.51-3.23 (m, 4H), 3.53 (s, 3H), 3.71 (s, 3H), 3.80 (s, 2H), 7.24-7.27 (m, 2H), 7.42 (s, 1H). ESI-MS: 376 (M + H)$^+$ |
| P3.16 | 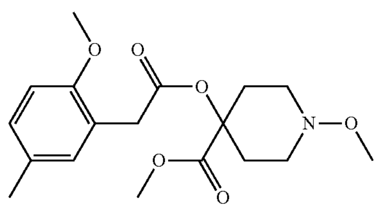 [SMILES: COC(=O)C1(OC(=O)Cc2cc(C)ccc2OC)CCN(OC)CC1] | gum | $^1$H-NMR (DMSO-d$_6$): 1.81-2.28 (m, 4H), 2.29 (s, 3H), 2.56-3.32 (m, 4H), 3.51 (s, 3H), 3.65 (s, 2H), 3.72 (s, 3H), 3.79 (s, 3H), 6.77 (d, 1H), 7.02 (s, 1H), 7.06 (d, 1H). ESI-MS: 352 (M + H)$^+$ |
| P3.17 | 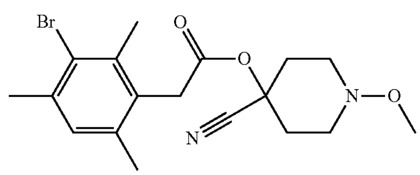 | solid | $^1$H-NMR (300 Mz, DMSO-d$_6$): 1.89-2.43 (m, 4H), 2.21 (s, 3H), 2.31 (s, 3H), 2.36 (s, 3H), 2.55-3.28 (m, 4H), 3.41 (s, 3H), 3.92 (s, 2H), 7.09 (s, 1H). ESI-MS: 395/397 (M + 1)$^+$, 417/419 (M + Na)$^+$. |
| P3.18 | 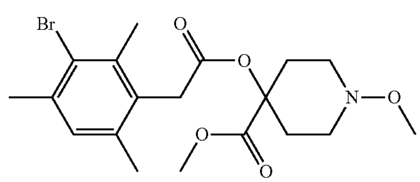 | oil | $^1$H-NMR (300 Mz, DMSO-d$_6$): 1.65-2.06 (m, 4H), 2.19 (s, 3H), 2.29 (s, 3H), 2.34 (s, 3H), 2.81-3.13 (m, 4H), 3.38 (s, 3H), 3.57 (s, 3H), 3.82 (s, 2H), 7.04 (s, 1H). ESI-MS: 428/430 (M + 1)$^+$, 450/452 (M + Na)$^+$. |
| P3.19 | 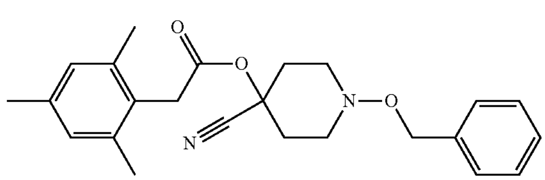 [SMILES: Cc1cc(C)c(CC(=O)OC2(C#N)CCN(OCc3ccccc3)CC2)c(C)c1] | gum | $^1$H-NMR (CDCl$_3$): 1.95-2.50 (m, 4H), 2.26 (s, 3H), 2.29 (s, 6H), 2.82-3.07 (m, 4H), 3.70 (s, 2H), 4.67 (s, 2H), 6.87 (s, 2H), 7.31-7.36 (m, 5H). ESI-MS: 393 (M + H)$^+$ |
| P3.20 | 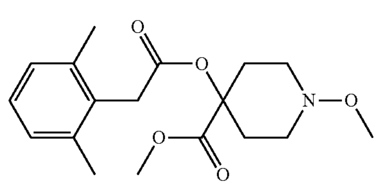 [SMILES: COC(=O)C1(OC(=O)Cc2c(C)cccc2C)CCN(OC)CC1] | oil | $^1$H-NMR (CDCl$_3$): 2.06-2.40 (m, 4H), 2.33 (s, 6H), 2.47-3.18 (m, 4H), 3.48 (s, 3H), 3.68 (s, 3H), 3.74 (s, 2H), 7.05-7.09 (m, 3H). ESI-MS: 336 (M + H)$^+$, 358 (M + Na)$^+$, 390 (M + MeOH + Na)$^+$ |

TABLE P3-continued

Physical data of intermediates of formula IV or XI:

| Compound No. | Structures | Melting Point | MS/NMR |
|---|---|---|---|
| P3.21 | 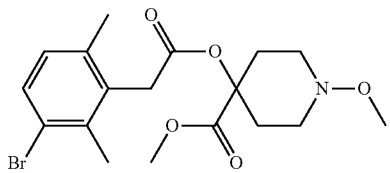 | oil | ESI-MS: 414/416 (M + H)+, 436/438 (M + Na)+ |
| P3.22 | 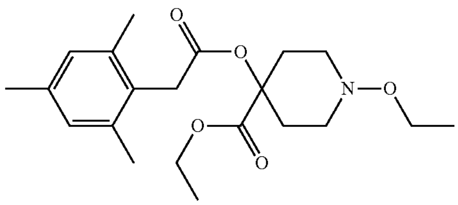 [SMILES: CCOC(=O)C1(OC(=O)Cc2c(C)cc(C)cc2C)CCN(OCC)CC1] | oil | ¹H-NMR (CDCl₃): 1.17-1.21 (m, 6H), 2.06-2.40 (m, 4H), 2.26 (s, 3H), 2.31 (s, 6H), 2.47-3.18 (m, 4H), 3.68 (s, 2H), 3.72 (q, 2H), 4.12 (q, 2H), 6.87 (s, 2H). ESI-MS: 378 (M + 1), 400 (M + Na+), 432 (M + MeOH + Na+) |
| P3.23 | 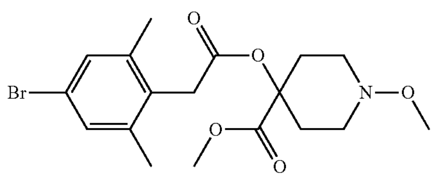 | oil | ¹H NMR (CDCl₃): 1.85-2.06 (m, 4H), 2.24 (s, 3H), 2.30 (s, 3H), 2.53-3.16 (m, 4H), 3.50 (s, 3H), 3.67 (s, 3H), 3.88 (s, 2H), 6.92 (s, 1H), 7.24 (s, 1H) ESI-MS (+): 414/416 (M + 1), 436/438 (M + Na+), 468/470 (M + MeOH + Na+) |
| P3.24 | 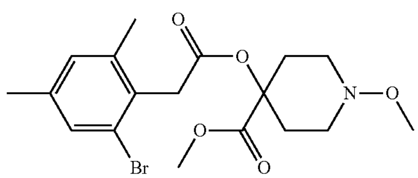 | oil | ¹H NMR (CDCl₃): 1.81-2.18 (m, 4H), 2.21 (s, 3H), 2.32 (s, 3H), 2.53-3.26 (m, 4H), 3.51 (s, 3H), 3.60 (s, 3H), 3.68 (s, 2H), 7.04 (s, 1H), 7.35 (s, 1H) ESI-MS (+): 414/416 (M + 1), 436/438 (M + Na+), 468/470 (M + MeOH + Na+) |
| P3.25 | 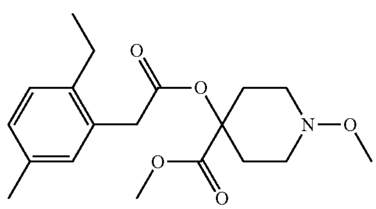 [SMILES: CCc1ccc(C)cc1CC(=O)OC1(C(=O)OC)CCN(OC)CC1] | oil | ¹H-NMR (300 Mz, DMSO-d₆): 1.18 (t, 3H), 1.70-2.20 (m, 4H), 2.27 (s, 3H), 2.58 (q, 2H), 2.52-3.18 (m, 4H), 3.51 (s, 3H), 3.66 (s, 2H), 3.68 (s, 3H), 7.03-7.08 (m, 3H). ESI-MS: 350 (M + H)+, 372 (M + Na)+ |
| P3.26 | 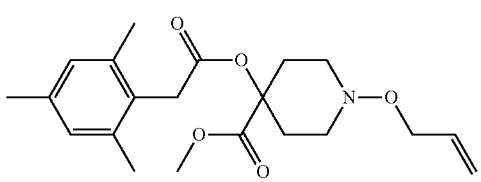 [SMILES: C=CCON1CCC(OC(=O)Cc2c(C)cc(C)cc2C)(C(=O)OC)CC1] | oil | ¹H-NMR (300 Mz, DMSO-d₆): 1.70-2.18 (m, 4H), 2.25 (s, 3H), 2.29 (s, 6H), 2.52-3.16 (m, 4H), 3.67 (s, 3H), 3.69 (s, 2H), 4.17 (d, 2H), 5.16-5.29 (m, 2H), 5.89-5.96 (m, 1H), 6.86 (s, 2H). ESI-MS: 376 (M + H)+, 398 (M + Na)+ |
| P3.27 | 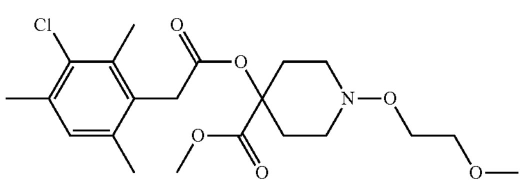 | oil | ¹H-NMR (300 Mz, DMSO-d₆): 1.68-2.08 (m, 4H), 2.22 (s, 3H), 2.27 (s, 3H), 2.31 (s, 3H), 2.21-3.11 (m, 4H), 3.23 (s, 3H), 3.42 (t, 2H), 3.59 (s, 3H), 3.69 (t, 2H), 3.82 (s, 2H), 7.05 (s, 1H). ESI-MS: 428 (M + H)+, 450 (M + Na)+ |
| P3.28 | 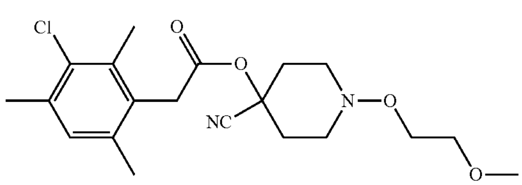 | oil | ¹H-NMR (300 Mz, DMSO-d₆): 1.93-2.39 (m, 4H), 2.23 (s, 3H), 2.28 (s, 3H), 2.31 (s, 3H), 2.65-3.04 (m, 4H), 3.24 (s, 3H), 3.43 (t, 2H), 3.71 (t, 2H), 3.90 (s, 2H), 7.07 (s, 1H). ESI-MS: 395 (M + H)+, 417 (M + Na)+. |

Intermediates of the formula V, VII or VIII from Table P4 can be prepared by analogous procedures.

TABLE P4

Physical data of intermediates of formula V, VII or VIII:

| Compound No. | Structures | Melting Point | MS/NMR/IR |
|---|---|---|---|
| P4.1 | 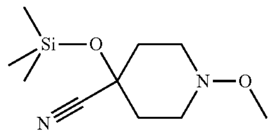 | liquid | $^1$H-NMR (CDCl$_3$): 0.25 (s, 9H), 1.76-2.30 (m, 4H), 2.70-3.34 (m, 4H), 3.51 (s, 3H). |
| P4.2 | 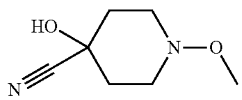 | solid | $^1$H-NMR (CDCl$_3$): 1.80-2.34 (br m, 4H), 2.73-3.20 (m, 2H), 3.51 (s, 3H). |
| P4.3 | 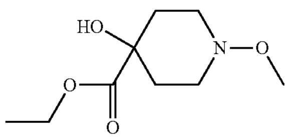 | oil | $^1$H-NMR (CDCl$_3$): 1.25 (t, 3H), 1.25-1.75 (m, 2H), 2.03-2.2.40 (m, 2H), 2.65-3.27 (m, 4H + OH), 3.52 (br s, 3H), 4.19 (q, 2H). LC/MS (ES+): 204 (M + H)$^+$; R$_t$ = 0.87 min |
| P4.4 | 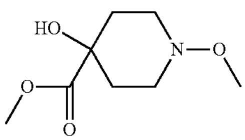 | oil | $^1$H-NMR (CDCl$_3$): 1.30-3.30 (very br m, 8H, mixture of conformers), 3.54 (s, 3H), 3.78 (s, 3H). LC/MS (ES+): 190 (M + H)$^+$; R$_t$ = 0.52 min |
| P4.5 | 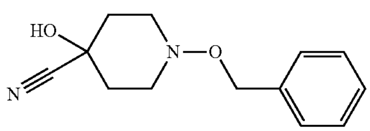 [SMILES: N#CC1(O)CCN(OCc2ccccc2)CC1] | 78-80° C. | $^1$H-NMR (DMSO-d$_6$): 1.67-2.08 (m, 4H), 2.59-3.23 (m, 4H), 4.63 (s, 2H), 6.55 (d, 1H), 7.26-7.36 (m, 5H). ESI-MS: 233 (M + H)$^+$ |
| P4.6 | 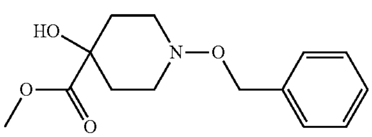 [SMILES: COC(=O)C1(O)CCN(OCc2ccccc2)CC1] | 67-69° C. | $^1$H-NMR (DMSO-d$_6$): 1.38-2.16 (m, 4H), 2.61-3.01 (m, 4H), 3.62 (s, 3H), 4.61 (s, 2H), 5.35 (s, 1H), 7.24-7.36 (m, 5H). ESI-MS: 266 (M + H)$^+$ |
| P4.7 | 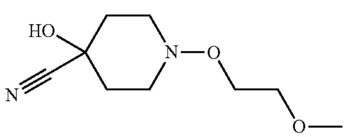 | oil | $^1$H-NMR (DMSO-d$_6$): 1.69-2.12 (m, 4H), 2.56-3.20 (m, 4H), 3.23 (s, 3H), 3.43 (t, 2H), 3.69 (t, 2H), 6.53 (d, 1H). |
| P4.8 | 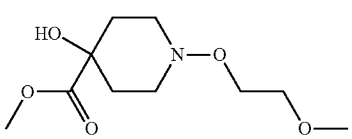 | oil | $^1$H-NMR (DMSO-d$_6$): 1.36-2.14 (m, 4H), 2.57-3.02 (m, 4H), 3.23 (s, 3H), 3.43 (t, 2H), 3.63 (s, 3H), 3.67 (t, 2H), 5.36 (s, 1H). ESI-MS: 234 (M + H)$^+$ |
| P4.9 | 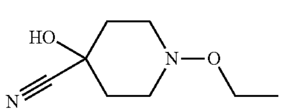 | oil | $^1$H-NMR (DMSO-d$_6$): 1.09 (t, 3H), 1.68-2.06 (m, 4H), 2.49-3.17 (m, 4H), 3.63 (q, 2H), 6.51 (br d, 1H). ESI-MS: 171 (M + H)$^+$ |
| P4.10 | 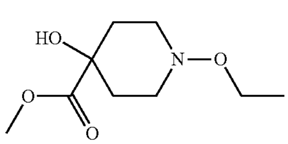 | oil | $^1$H-NMR (DMSO-d$_6$): 1.07 (t, 3H), 1.66-1.88 (m, 4H), 2.56-2.73 (m, 4H), 3.6 (m, 5H), 5.34 (s, 1H). ESI-MS: 204 (M + H)$^+$ |

TABLE P4-continued

Physical data of intermediates of formula V, VII or VIII:

| Compound No. | Structures | Melting Point | MS/NMR/IR |
|---|---|---|---|
| P4.11 | HO, N≡C-[piperidine]-N—O—CH$_2$—CH=CH$_2$ | oil | $^1$H-NMR (DMSO-d$_6$): 1.70-2.10 (m, 4H), 2.59-3.10 (m, 4H), 4.21 (d, 2H), 5.12-5.26 (m, 2H), 5.85-6.03 (m, 1H), 6.56 (d, 1H) ESI-MS: 183 (M + H)$^+$ |
| P4.12 | HO, CH$_3$O-C(=O)-[piperidine]-N—O—CH$_2$—CH=CH$_2$ | oil | $^1$H-NMR (DMSO-d$_6$): 1.68-1.72 (m, 2H), 2.07-2.15 (m, 2H), 2.76-2.83 (m, 2H), 3.14-3.20 (m, 2H), 3.77 (s, 3H), 4.18 (d, 2H), 5.14-5.29 (m, 2H), 5.88-6.01 (m, 1H). ESI-MS: 216 (M + H)$^+$ |

FORMULATION EXAMPLES

%=Percent by Weight

Example F1

Emulsion Concentrates

|  | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2

Solutions

|  | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3

Granules

|  | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4

Dusts

|  | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5

Wettable Powders

|  | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |

-continued

|  | a) | b) | c) |
|---|---|---|---|
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

Extruder Granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

Coated Granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8a

Suspension Concentrate

| Active ingredient | 40% |
|---|---|
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

Example F8b

Suspension Concentrate

| Active ingredient | 10% |
|---|---|
| Naphthalenesulfonic acid, sodium salt condensed with formaldehyde | 2% |
| Solution of an acrylic graft copolymer in water and propyleneglycole | 8% |
| Silicone antifoam emulsion | 0.5% |
| DL-propanediol-(1,2) | 3% |
| Heteropolysaccharide | 0.5% |
| 1,2-Benzisothiazol-3-one | 0.2% |
| Water | 75.8% |

The finely ground active ingredient is mixed intimately with the additives. Suspensions of any desired concentration can be prepared from the thus resulting suspension concentrate by dilution with water.

Example F9

Powders for Dry Seed Treatment

|  | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

Example F10

Flowable Concentrate for Seed Treatment

| active ingredient | 40% |
|---|---|
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Example F11a

Oil-Based Suspension Concentrate (Based on a Vegetable Oil)

| | |
|---|---|
| Active ingredient | 10% |
| Tristyrylphenole with 16 moles EO | 10% |
| Block copolymer of polyhydroxystearic acid and polyalkylene glycols | 2% |
| AEROSIL 200 | 1% |
| Rape seed oil methyl ester | 12% |
| Oleic acid | 65% |

Example F11b

Oil-Based Suspension Concentrate (Based on a Mineral Oil)

| | |
|---|---|
| Active ingredient | 10% |
| Ethoxylated alcohols, C16-18 and C18-unsatd | 5% |
| Dodecyl-benzene sulfonic acid Ca-salt linear | 2.5% |
| 2-Pyrrolidinone, 1-ethenylhexadecyl-, homopolymer | 1% |
| Organophilic clay | 1% |
| Mixture of petroleum | 80.5% |

The finely ground active ingredient is mixed intimately with the additives. Suspensions of any desired concentration can be prepared from the thus resulting suspension concentrate by dilution with water.

Preferably, the term "active ingredient" used above refers to one of the compounds selected from Tables 1 to 28 shown above. It also refers to mixtures of the compound of formula I, in particular a compound selected from said Tables 1 to 28, with other insecticides, fungicides, herbicides, safeners, adjuvants and the like, which mixtures are specifically disclosed above.

BIOLOGICAL EXAMPLES

These examples illustrate the pesticidal/insecticidal properties of compounds of formula I.

Example B1

Activity Against *Myzus persicae* (Green Peach Aphid)

(Mixed Population, Feeding/Residual Contact Activity, Preventive)

Sunflower leaf discs are placed on agar in a 24-well microtiter plate and sprayed with test solutions. After drying, the leaf discs are infested with an aphid population of mixed ages. After an incubation period of 6 days, samples are checked for mortality and special effects (e.g. phytotoxicity).

In this test, compounds listed in the tables above show good activity. In particular compounds P1.2, P1.3, P1.4, P1.5, P1.6, P1.7, P1.9, P1.10, P1.11, P1.13, P1.14, P1.17, P1.35, P2.1, P2.2, P2.3, P2.4, P2.5, P2.6, P2.7, P2.8 P2.12, P2.34, P2.37, P2.49, P2.50 and P.2.51 show an activity of over 80% at a concentration of 400 ppm.

Example B2

Activity Against *Myzus persicae* (Green Peach Aphid)

(Mixed Population, Systemic/Feeding Activity, Curative)

Roots of pea seedlings, infested with an aphid population of mixed ages, are placed directly in the test solutions. 6 days after introduction, samples are checked for mortality and special effects on the plant.

In this test, compounds listed in the tables above show good activity. In particular compounds P1.1, P1.2, P1.3, P1.4, P1.5, P1.6, P1.8, P1.9, P1.10, P1.11, P1.12, P1.13, P1.14, P1.17, P1.18, P1.19, P1.33, P1.34, P1.35, P2.1, P2.2, P2.3, P2.5, P2.7, P2.8, P2.12, P2.13, P2.49, P2.50 and P2.51 show an activity of over 80% at a concentration of 400 ppm.

Example B3

Activity Against *Thrips tabaci* (Onion *Thrips*)

(Mixed Population, Feeding/Residual Contact Activity, Preventive)

Sunflower leaf discs are placed on agar in a 24-well microtiter plate and sprayed with test solutions. After drying, the leaf discs are infested with a thrips population of mixed ages. After an incubation period of 6 days, samples are checked for mortality and special effects (e.g. phytotoxicity).

In this test, compounds listed in the tables above show good activity. In particular compound P1.13, P1.17, P2.2, P2.12, and P2.14 shows an activity of over 80% at a concentration of 400 ppm.

Example B4

Activity Against *Tetranychus urticae* (Two-Spotted Spider Mite)

(Mixed Population, Feeding/Residual Contact Activity, Preventive)

Bean leaf discs on agar in 24-well microtiter plates are sprayed with test solutions. After drying, the leaf discs are infested with mite populations of mixed ages. 8 days later, discs are checked for egg mortality, larval mortality, and adult mortality.

In this test, compounds listed in the tables above show good activity. In particular compounds P1.10, P1.11, P1.15, P1.17, P1.19, P1.29, P1.34, P2.3, P2.4, P2.6, P2.9, P2.12, P2.13, P2.14, P2.20, P2.35, P2.40, P2.49 and P2.51 show an activity of over 80% at a concentration of 400 ppm.

Example B5

Activity Against *Bemisia tabaci* (Tobacco White Fly)

(Larvicide, Contact/Feeding)

Bean plants are infested with 20-30 adults that were removed after a 4 day egg-laying period. After another 7 days, bean plants with hatched nymphs (N–2) are treated (2 replicates) with the test solutions in a spray chamber. Three weeks later, samples are checked for number of emerged adults. Efficacy was calculated by comparing number of emerged adults in treated and non treated samples.

In this test, compounds listed in the tables above show good activity. For example compounds P1.11 and P2.3 show an activity of over 80% at a concentration of 200 ppm.

Example B6

Activity Against *Nilaparvata lugens* (Brown Rice Planthopper)

(Larvicide, Feeding/Contact)

Rice seedlings are treated with the diluted test solutions in a spray chamber. After drying, they are infested with 20 $N_3$ nymphs (2 replicates). 6-12 days after the treatment samples are checked for mortality, growth regulation, and effects on the $F_1$ generation.

In this test, compounds listed in the tables above show good activity. For example compounds P1.11 and P2.3 show an activity of over 80% at a concentration of 400 ppm.

Example B7

Activity Against *Aphis craccivora* (Cowpea Aphid)

(Mixed Population, Contact/Feeding)

Pea seedlings, infested with an aphid population of mixed ages, are treated (2 replicates) with diluted test solutions in a spray chamber. 6 days after treatment, samples are checked for mortality.

In this test, compounds listed in the tables above show good activity. For example compounds P2.3 show an activity of over 80% at a concentration of 400 ppm.

Example B8

Activity Against *Aphis craccivora* (Cowpea Aphid)

(Mixed Population, Systemic/Feeding)

Roots of pea seedlings, infested with an aphid population of mixed ages, are placed (2 replicates) directly in the test solution. 6 days later, samples are checked for mortality.

In this test, compounds listed in the tables above show good activity. For example compounds P1.11 and P2.3 show an activity of over 80% at a concentration of 25 ppm.

Example B9

Translaminar Activity Against *Aphis craccivora* (Cowpea Aphid)

French bean leaves (*Phaseolus vulgaris*) are infested with about 20 mixed age individuals on the lower leaf side using clip cages. 1 day after the infestation, the upper side of the leaves is treated with the test solution by painting. 5 days later, samples are checked for mortality.

In this test, compounds listed in the tables above show good activity. For example compounds P2.3 show an activity of over 80% at a concentration of 400 ppm.

Example B10

Drench Activity Against *Myzus persicae* (Green Peach Aphid)

Pea seedlings cultivated in field soil are treated as drench application and infested with a mixed population of *M. persicae*. 7 days after infestation, samples are checked for mortality.

In this test, compounds listed in the tables above show good activity. For example compounds P1.11, P2.3 show an activity of over 80% at a concentration of 25 ppm.

Example B11

Activity Against *Myzus persicae* (Green Peach Aphid)

(Mixed Population, Feeding/Residual Contact Activity, Plant Damage Evaluation)

Pepper plants infested with a mixed population of *Myzus persicae* are treated with diluted test solutions of the compounds in a spray chamber. 6 days after treatment, samples are checked for mortality and for plant damage (phytotoxicity), visual assessment being made using a 0-100% rating scale (100%=total damage to plant; 0%=no damage to plant).

In this test, compounds listed in the tables above show good activity against *Myzus persicae* and acceptable plant compatibility. For example compounds P1.1, P1.3, P1.4, P1.6, P1.11, P1.13, P2.1, P2.2, P2.8, P2.47 and P2.48 show an activity of greater or equal to 80% against *Myzus persicae* and damage to pepper plants less or equal to 10% at a concentration of 200 ppm.

The invention claimed is:
1. Compounds of the formula I

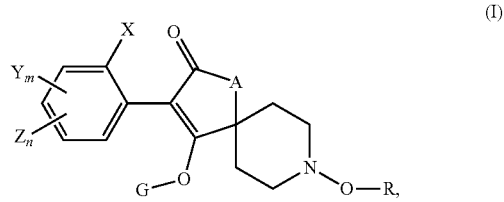

wherein
X, Y and Z independently of each other are $C_{1-4}$alkyl, $C_{3-6}$cycloalkyl, $C_{1-4}$haloalkyl, $C_{1-4}$alkoxy, $C_2$-$C_6$alkenyl, $C_2$-$C_6$alkynyl, halogen, phenyl or phenyl substituted by $C_{1-4}$alkyl, $C_{1-4}$haloalkyl, halogen or cyano;
m and n, independently of each other, are 0, 1, 2 or 3 and m+n is 0, 1, 2 or 3;
G is hydrogen, a metal, ammonium, sulfonium or a latentiating group;
A is sulfur; and
R is hydrogen, $C_{1-6}$alkyl, $C_{1-6}$haloalkyl, $C_{1-6}$cyanoalkyl, $C_2$-$C_6$alkenyl, $C_3$-$C_6$alkynyl, benzyl, $C_{1-4}$alkoxy($C_{1-4}$)alkyl or $C_{1-4}$alkoxy($C_{1-4}$)alkoxy($C_{1-4}$)alkyl; or
an agrochemically acceptable salt or an N-oxide thereof.
2. A process for the preparation of the compounds of the formula I according to claim 1, wherein G is hydrogen, which comprises cyclisation of the compound of formula IV

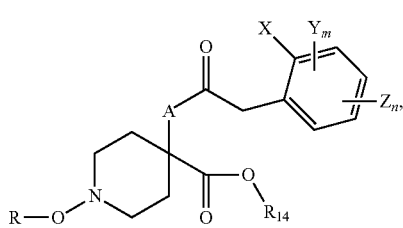

wherein A, X, Y, Z, m, n and R have the meanings assigned to them in claim 1, and $R_{14}$ is $C_{1-6}$alkyl, under basic conditions.

3. A pesticidal composition comprising a pesticidal effective amount of at least one compound of formula I according to claim 1.

4. A pesticidal composition according to claim 3, which, in addition to comprising the compound of formula I, comprises formulation adjuvants.

5. A pesticidal composition according to claim 3, wherein the formulation adjuvant is an oil of vegetable or animal origin, a mineral oil, alkyl esters of these oils or mixtures of these oils and oil derivatives, or is a fertilizer or an ammonium- or phosphonium salt, optionally in a mixture with the above oils and oil derivatives.

6. A pesticidal composition according to claim 3, which, in addition to comprising the compound of formula I, comprises at least one additional insecticide, acaricide, nemacitide or molluscicide.

7. A pesticidal composition according to claim 3, which, in addition to comprising the compound of formula I, comprises at least one additional fungicide, herbicide, safener or plant growth regulator.

8. A method of combating and controlling pests which comprises applying to a pest, to a locus of a pest, or to a plant susceptible to attack by a pest a pesticidally effective amount of a compound of formula I.

9. A method of combating and controlling pests which comprises applying to a pest, to a locus of a pest, or to a plant susceptible to attack by a pest a pesticidal composition according to claim 3.

10. Compounds of the formula IV

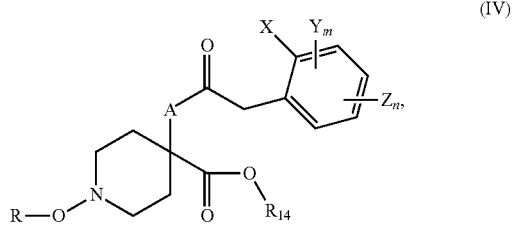

or salts thereof, wherein A, X, Y, Z, m, n and R have the meanings assigned to them in claim 1, and $R_{14}$ is $C_{1-6}$alkyl.

* * * * *